(12) United States Patent
Hebeisen et al.

(10) Patent No.: US 7,973,051 B2
(45) Date of Patent: Jul. 5, 2011

(54) AMINOTHIAZOLES AS FBPASE INHIBITORS FOR DIABETES

(75) Inventors: Paul Hebeisen, Basel (CH); Eric A. Kitas, Aesch BL (CH); Rudolf E. Minder, Aesch BL (CH); Peter Mohr, Basel (CH); Hans Peter Wessel, Schliengen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/267,661

(22) Filed: Nov. 10, 2008

(65) Prior Publication Data

US 2009/0143448 A1 Jun. 4, 2009

(30) Foreign Application Priority Data

Nov. 30, 2007 (EP) .................... 07122019

(51) Int. Cl.
*A61K 31/4365* (2006.01)
*A61K 31/427* (2006.01)
*A61K 31/428* (2006.01)

(52) U.S. Cl. ........ 514/301; 514/367; 514/369; 514/371; 546/114; 548/163; 548/185; 548/196

(58) Field of Classification Search .................. None
See application file for complete search history.

(56) References Cited

FOREIGN PATENT DOCUMENTS

| DK | 2006 00313 | | 3/2006 |
| EP | 0 337 819 | A | 10/1989 |
| WO | WO 01/57037 | A1 | 8/2001 |
| WO | WO 03/039451 | A2 | 5/2003 |
| WO | WO 2005/103022 | A1 | 11/2005 |
| WO | WO 2007/137962 | * | 12/2007 |
| WO | WO 2007/137962 | A1 | 12/2007 |

OTHER PUBLICATIONS

Bouillon et al. J Comb Chem. 2007; 9(6). Author Manuscript, pp. 1-13.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Wolff et al. Burger's Medicinal Chemistry and Drug Discovery. 5th ed. vol. 1: Principles and Practice (1995). pp. 975-977.*
Arzneimittel Forschung, Drug Research, ECV, vol. 8, No. 7a, Jan. 1, 1958, pp. 448-454—XP009088824.
Imtiaz Husain, M, The Indian Journal of Pharmacy, CC, CC, vol. 38, No. 2, Mar. 1, 1976, pp. 47-49, XP008036020.
Yousef, Medicinal Chemistry Research, vol. 10, No. 6, XP008020857, 2001.
Zee-Cheung, Journal of Medicinal Chemistry, 22 (1), 28-32, XP002520027, 1978.
Hof, H.,Antimicrobial Chemotherapy 14 (1) 31-9—XP002520028, 1984.
Husain, M.I. et al; Indian Drugs, (1986) 24:1 p. 21.
About Out A.A. et al, J. Drugs. Res. Egypt (1974) 6:2 p. 123.
Holland, G.F.; J. Org. Chem. (1961) 26, p. 1662.
Howbert, J.J. et al: J. Med. Chem. (1990) 33:9 p. 2393.

* cited by examiner

*Primary Examiner* — Rebecca L Anderson
*Assistant Examiner* — Alicia L Otton
(74) *Attorney, Agent, or Firm* — George W. Johnston; Dennis P. Tramaloni; Samuel H. Megerditchian

(57) ABSTRACT

Compounds of formula (I)

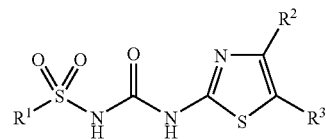

as well as pharmaceutically acceptable salts and esters thereof, wherein $R^1$ to $R^3$ have the significance given in claim 1 and which can be used in the form of pharmaceutical compositions.

6 Claims, No Drawings

AMINOTHIAZOLES AS FBPASE INHIBITORS FOR DIABETES

PRIORITY TO RELATED APPLICATION(S)

This application claims the benefit of European Patent Application No. 07122019.8, filed Nov. 30, 2007, which is hereby incorporated by reference in its entirety.

FIELD OF THE INVENTION

The present invention relates to novel compounds useful as FBPase inhibitors.

The invention is concerned particularly with compounds of formula (I)

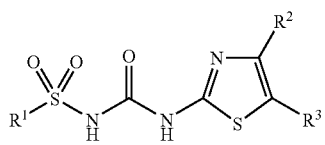

and pharmaceutically acceptable salts and esters thereof.

All documents cited to below are expressly incorporated herein by reference.

BACKGROUND OF THE INVENTION

Fructose-1,6-bisphosphatase (FBPase) is a rate-limiting enzyme of gluconeogenesis that is allosterically regulated by AMP and responsible for the hydrolysis of Fructose-1,6-bisphosphate to Fructose-6-phosphate. FBPase AMP site inhibitors have valuable pharmacological properties suitable in both human and veterinary medicine.

As inhibitors of FBPase and of the production of Fructose-6-phosphate that is reversibly converted to Glucose-6-phosphate, a metabolite which represents a common precursor for diverse essential metabolic pathways generating glucose, glycogen, ATP, amino acids, nucleotides, NADPH and so forth, have a large variety of indications related to the management of body homeostasis and the prevention of metabolic dysfunctions.

SUMMARY OF THE INVENTION

The invention provides for a compound of formula (I)

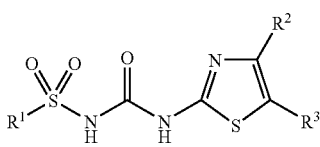

wherein
$R^1$ is

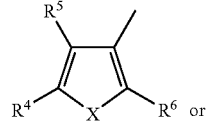

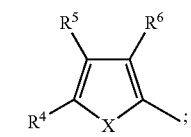

X is S, N—$R^7$ or O;
$R^2$ and $R^3$ are in each case independently selected from hydrogen, alkyl, alkoxy, cycloalkyl, haloalkyl, haloalkoxy, aryl, aryloxy, alkoxyalkyl, alkoxycarbonyl, alkoxyalkoxy, hydroxyalkoxy, heterocyclyl, heterocycloalkyl, halogen, aralkyl, hydroxyl, —S—$R^8$, —O—$R^8$, —N($R^8$)$_2$, —$R^{10}$—S—$R^8$, —$R^{10}$—O—$R^8$, —$R^{10}$—N($R^8$)$_2$, nitro, cyano and —C(O)$R^7$, —$R^8$—C(O)$R^7$; or
$R^2$ and $R^3$ together with the carbon atoms to which they are attached form a 5- or 6-membered unsaturated ring, which may contain 1 or 2 heteroatoms selected from N, O and S, wherein the ring is optionally substituted with one to three substituents independently selected from $R^9$, —O—$R^9$, —O—CO—$R^9$, —N$R^9$—CO—$R^9$, —S—$R^9$, —SO—$R^9$, —SO$_2$—$R^9$, —CO$_2$—$R^9$, —CON($R^9$)$_2$, —$R^{10}$—O—$R^9$, —$R^{10}$—O—CO$R^9$, —$R^{10}$—N$R^9$—CO$R^9$, —$R^{10}$—S—$R^9$, —$R^{10}$—SO—$R^9$, —$R^{10}$—SO$_2$—$R^9$, —$R^{10}$—CO$_2$—$R^9$, —$R^{10}$—CON($R^9$)$_2$ and N($R^9$)$_2$;
with the proviso that $R^2$ is not hydrogen and $R^3$ is not halogen, when X is S and $R^4$ and $R^5$ do not form a ring;
$R^4$ and $R^5$ are independently selected from hydrogen, alkyl, alkoxy, cycloalkyl, haloalkyl, haloalkoxy, hydroxyalkyl, aryl, aryloxy, alkoxyalkyl, alkoxycarbonyl, alkoxyalkoxy, hydroxyalkoxy, heterocyclyl, heterocycloalkyl, halogen, aralkyl, hydroxyl, amino, nitro, cyano or —C(O)$R^7$, —$R^8$—C(O)$R^7$ and $R^{10}$—O—C(O)$R^7$; or
$R^4$ and $R^5$ together with the carbon atoms to which they are attached form a 5- or 6-membered unsaturated or saturated ring which may contain 1 or 2 heteroatoms selected from N, O and S,
wherein the ring is optionally substituted with one to three substituents independently selected from $R^9$, —O—$R^9$, —O—CO—$R^9$, —N$R^9$—CO—$R^9$, —S—$R^9$, —SO—$R^9$, —SO$_2$—$R^9$, —CO$_2$—$R^9$, —CON($R^9$)$_2$, —$R^{10}$—O—$R^9$, —$R^{10}$—O—CO$R^9$, —$R^{10}$—N$R^9$—CO$R^9$, —$R^{10}$—S—$R^9$, —$R^{10}$—SO—$R^9$, —$R^{10}$—SO$_2$—$R^9$; —$R^{10}$—CO$_2$—$R^9$; —$R^{10}$—CON($R^9$)$_2$, N($R^9$)$_2$, cyano, nitro and halogen;
$R^6$ is hydrogen, alkyl, alkoxy, halogen, haloalkyl, haloalkoxy, alkoxyalkyl or alkoxyalkoxy;
$R^7$ is hydrogen, alkyl, alkoxy, haloalkoxy, alkoxyalkyl, alkoxyalkoxy, hydroxyalkoxy, hydroxyalkyl, cycloalkyl, heterocycloalkyl, aralkyl, hydroxyl or haloalkyl;
$R^8$ is in each case independently selected from hydrogen, alkyl, cycloalkyl, heterocycloalkyl, aralkyl or haloalkyl;
$R^9$ is in each case independently selected from hydrogen or an saturated and/or unsaturated, acyclic and/or cyclic organic residue with up to 20 carbon atoms which may comprise up to 5 heteroatoms selected from N, S and/or O, which may be substituted by halogen, hydroxy, alkoxy, —C(O)$R^7$, —$R^8$—C(O)$R^7$, $R^{10}$—O—C(O)$R^7$, carboxyester or carboxyamide; and $R^{10}$ is alkylene, arylene, aralkylene, alkarylene;
and pharmaceutically acceptable salts and esters thereof.

The invention also provides for is a process for the preparation of a compound of formula I

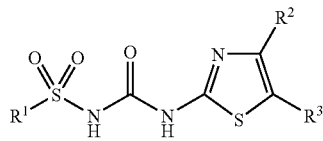

comprising the step of reacting a compound according to formula IIa or IIb

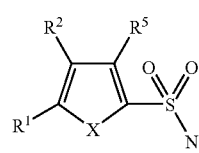

IIa

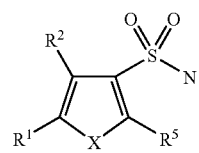

IIb in the presence of a base, phenyl chloroformate and a compound according to formula III

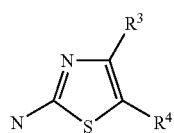

III wherein $R^1$ to $R^6$ are defined above.

Further provided is a pharmaceutical composition, comprising a therapeutically effective amount of a compound according to formula (I) and a therapeutically inert carrier.

DETAILED DESCRIPTION

As inhibitors of FBPase and of gluconeogenesis in the liver, or in other organs capable of producing glucose like kidney or intestine, compounds of the present invention are hypoglycemic agents and are indicated for the treatment and/or the prophylaxis of disorders of glucose homeostasis, such as Diabetes Mellitus, in particular Type II and Type I Diabetes Mellitus (NIDDM and IDDM), Impaired Fasting Glucose (IFG), Impaired Glucose Tolerance (IGT), and for the prevention of the progression of disorders of the Metabolic Syndrome (MetS, also described as Syndrome X or Insulin Resistance Syndrome) which most important components are insulin resistance (with or without IGT), obesity, dyslipidemia, hypertension, prothrombic and proinflammatory states. As such, compounds of the present invention are also indicated for the prevention and/or the treatment of diabetic complications or diabetic-associated diseases such as cardiomyopathy, macrovascular atherosclerotic disorders, including coronary, cerebrovascular and peripheral artery diseases, microvascular diseases including retinopathy, cataracts, blindness and nephropathy, neuropathy (peripheral neuropathy and sympathetic nerve disorders), diabetic necrosis, infection or depression, and so forth.

In addition, as inhibitors of FBPase that cause the accumulation of Fructose-1,6-bisphosphate capable for increasing the glycolytic production of ATP, compounds of the present invention have cytoprotective effects as anti-ischemic agents and are useful for preventing ischemia-induced tissue damage. Therefore, compounds of the present invention can be used in a variety of ischemic and inflammatory conditions where acute management of tissue injury could be beneficial such as surgical trauma, myocardial infarction, congestive heart failure, stroke, sickle cell disease, and so forth, and have further utility in cardioprotection, in improving cardiac function and tolerance to exercise, in improving red-blood cells and pulmonary endothelial functions, in organ preservation in transplants, and so forth. As such, compounds of the present invention can also be used to treat asthma attacks, hypertension, atherosclerosis and so forth, and in the management of certain excess glycogen storage diseases such as McArdle disease (GSD-Type V) and others.

Also as inhibitors of FBPase, and thereby of the production from the gluconeogenic pathway of Fructose-6-phosphate and Glucose-6-phosphate that serve as precursors for other pathways of hexose metabolism (e.g. synthesis of aminosugars/hexosamines that are used for the biosynthesis of glycoproteins, glycosphingolipids or glycosaminoglycans, and uronic acid pathway that leads to glucuronate, a precursor of proteoglycans and conjugated glucuronides, and so forth), or for the pentose phosphate pathway (PPP, also called phosphogluconate pathway) which provides the carbon source for common aromatic biosynthetic pathways (nucleotides and amino-acids synthesis) and generates NADPH for reductive biosynthesis (lipogenesis, steroidogenesis), compounds of the present invention can have further utility in the prevention and/or the management of a large set of diseases including obesity, atherosclerosis, inflammation, Alzheimer disease, cancer or respiratory disorders such as excess mucus production and allergic asthma, excess surfactant synthesis, cystic fibrosis, and so forth.

Furthermore, compounds of the present invention can be used in any disease, syndrome, symptom or organ malfunction found associated with increased expression and/or activity of one or another FBPase isoform, at the obvious exception of certain deficiencies where FBPase upregulation might be beneficial for ensuring normal body function, e.g. certain glycogen storage diseases, such as GSD-Type 0 (glycogen synthase deficiency).

The compounds of formula I and their pharmaceutically acceptable salts and esters are novel and have valuable pharmacological properties. In particular they are FBPase inhibitors and can be used in the prophylaxis and/or treatment of Diabetes Mellitus such as Type I, Type II and Type III Diabetes, Impaired Fasting Glucose (IFG), Impaired Glucose Tolerance (IGT), Metabolic Syndrome, insulin resistance, dyslipidemia, obesity, hypertension, atherosclerosis, diabetic complications, inflammation, respiratory diseases or ischemia. Preferred is the prophylaxis and/or prevention of progression and/or treatment of Diabetes Mellitus Type II, Diabetes Mellitus Type I, Diabetes Mellitus Type III, Impaired Fasting Glucose (IFG), Impaired Glucose Tolerance (IGT), Metabolic Syndrome, diabetic complications and ischemia. Particularly preferred is the prophylaxis and/or treatment of Diabetes Mellitus Type II and Diabetes Mellitus Type I.

Provided herein are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischemia, particularly Diabetes Mellitus Type II and Diabetes Mellitus Type I.

The compounds of the present invention can be combined with one or more additional active substances indicated for the management of human and veterinary homeostasis in any suitable ratio. Such substances may be insulin sensitizers such as peroxisome proliferator-activated receptor modulators (PPAR alpha, gamma, delta agonists, particularly with thiazolinediones such as rosiglitazone and pioglitazone), insulin secretagogues (sulfonylureas such as glyburide, glimepiride and glipizide, and non-sulfonylurea secretagogues such as the meglitinides repaglinide and nateglinide), insulin, metformin, alpha-glucosidase inhibitors (e.g. acarbose, miglitol), glucagon-like peptide (GLP-1) analogues (e.g. exenatide), dipeptidyl peptidase-IV (DPP-IV) inhibitors, glycogen phosphorylase inhibitors, glycogen synthase kinase-3 inhibitors, 11β-hydroxysteroid dehydrogenase-1 inhibitors, carnitine palmitoyltranferase-1 inhibitors, glucocorticoid receptor antagonists, glucagon receptor antagonists, Adenosine ($A_{2B}$) receptor agonists, amylin agonists (e.g. pramlintide), lipase inhibitor (e.g. orlistat), or any other synthetic or natural substance presenting valuable pharmacological properties useful for the treatment and/or the prevention of metabolic dysfunctions.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 3 carbon atoms Examples of straight-chain and branched $C_1$-$C_8$ alkyl groups are methyl, ethyl, propyl, isopropyl, butyl, isobutyl, tert. butyl, the isomeric pentyls, the isomeric hexyls, the isomeric heptyls and the isomeric octyls, preferably methyl, ethyl and isopropyl and most preferred methyl.

The term "cycloalkyl", alone or in combination, signifies a cycloalkyl ring with 3 to 8 carbon atoms, preferably a cycloalkyl ring with 3 to 6 carbon atoms and most preferably a cycloalkyl ring with 5 or 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "haloalkyl", alone or in combination, signifies an alkyl group as previously defined, wherein one to five hydrogen atoms are substituted by halogen, preferably fluoro. Preferred examples are pentafluoroethyl, more preferably trifluoromethyl and difluoromethyl, and most preferably trifluoromethyl.

The term "haloalkoxy", alone or in combination, signifies a group of the formula haloalkyl-O— in which the term "haloalkyl" is defined as before.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl, and preferably hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, alkyl-$SO_2$—, amino-$SO_2$—, cycloalkyl, a saturated 5- or 6-membered ring containing one or two heteroatoms selected from N and O and the like. Examples are phenyl or naphthyl, particularly phenyl optionally substituted with one to three, preferably one or two substituents independently selected from alkyl, halogen, alkoxy, trifluoromethoxy, carboxyester, methylsulfonyl, alkoxyalkoxy, hydroxyalkoxy, cyano, dimethylisoxazolyl, pyridinyl and trifluoromethyl. Preferred examples are phenyl or phenyl substituted with one to three, preferably one or two substituents independently selected from alkyl, halogen and alkoxy.

The term "aralkyl", alone or in combination, signifies the aryl-alkyl group, wherein the terms "aryl" and "alkyl" are as previously defined. Preferred is benzyl.

The term "alkaryl", alone or in combination, signifies the alkyl-aryl group, wherein the terms alkyl" and "aryl" are as previously defined. Preferred is methylphenyl.

The term "aryloxy", alone or in combination, signifies an aryl-O— group in which the term "aryl" has the previously given significance.

The term "aralkyloxy", alone or in combination, signifies an aralkyl-O— group in which the term "aralkyl" has the previously given significance. Preferred is benzyloxy.

The term "alkoxyalkyl", alone or in combination, signifies an alkyl group as defined before, wherein one or more hydrogen atoms, preferably one hydrogen atom is replaced by an alkoxy group as defined before. Examples of alkoxyalkyl are methoxymethyl and methoxyethyl.

The term "alkoxycarbonyl", alone or in combination, signifies an alkoxy-CO— group in which the term "alkoxy" has the previously given significance.

The term "alkoxyalkoxy", alone or in combination, signifies an alkoxy group as defined before, wherein one or more hydrogen atoms, preferably one hydrogen atom is replaced by an alkoxy group as defined before. Examples of alkoxyalkoxy are methoxymethoxy and methoxyethoxy, preferably methoxyethoxy.

The term "hydroxyalkoxy", alone or in combination, signifies an alkoxy group as defined before, wherein one or more hydrogen atoms, preferably one hydrogen atom is replaced by an hydroxy group. A preferred example of hydroxyalkoxy is hydroxyethoxy.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e.=N—) by oxido, with halogen, alkyl, cycloalkyl and alkoxy being preferred. Examples of such heterocyclyl groups are pyrrolidinyl, piperidinyl, pyridinyl, pyranyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, pyrrolyl, thienyl, thiazolyl, oxazolyl, isoxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl, 1,2,3,4-tetrahydroisoquinolyl and quinoxalinyl. Preferred are isoxazolyl, thiazolyl, thienyl, furyl, pyrrolyl, pyridinyl and pyranyl, wherein thiazolyl, thienyl, furyl and pyrrolyl are preferably benzocondensed or thiazolyl, thienyl, furyl, pyrrolyl and isoxazolyl are optionally substituted with one to three substituents, preferably one or two substituents independently selected from straight-chain or branched-chain alkyl, alkylthio, alkoxy, alkoxyalkyl, hydroxyalkyl and alkylene-carboxyester, particularly alkyl.

The term "heterocyclylalkyl", alone or in combination, signifies the heterocyclyl-alkyl group, wherein the terms "heterocyclyl" and "alkyl" are as previously defined.

The term "amino", alone or in combination, signifies a primary, secondary or tertiary amino group bonded via the nitrogen atom, with the secondary amino group carrying an alkyl, alkoxyalkyl or cycloalkyl substituent and the tertiary amino group carrying two similar or different alkyl, alkoxyalkyl or cycloalkyl substituents or the two nitrogen substituents together forming a ring, such as, for example, —NH$_2$, methylamino, ethylamino, dimethylamino, diethylamino, methyl-ethylamino, pyrrolyl, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "oxy", alone or in combination, signifies the —O— group.

The term "hydroxy", alone or in combination signifies the group —OH.

The term "nitro", alone or in combination signifies the —NO$_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

The compound of formula I can also be present in the form of zwitterions. A preferred pharmaceutically acceptable salt of compounds of formula I is the sodium salt.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Further preferred are the compounds of formula I

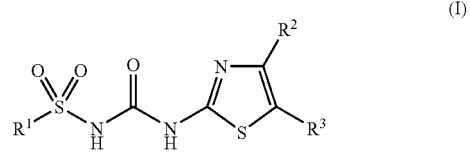

(I)

wherein

R$^1$ is

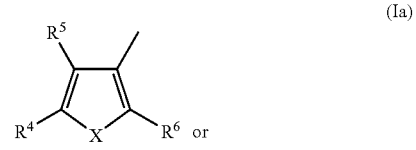

(Ia)

or (Ib)

X is S, N—R$^7$ or O;

R$^2$ and R$^3$ are in each case independently selected from hydrogen, alkyl, alkoxy, aryl, alkoxyalkyl, halogen and —S—R$^8$; or R$^2$ and R$^3$ together with the carbon atoms to which they are attached form a 6-membered unsaturated ring, which may contain 1 heteroatom N, wherein the ring is substituted with one or two substituents independently selected from halogen, $R^9$ and —O—$R^9$;
with the proviso that $R^2$ is not hydrogen and $R^3$ is not halogen, when X is S and $R^4$ and $R^5$ do not form a ring;
$R^4$ and $R^5$ are independently selected from hydrogen, alkyl, hydroxyalkyl, alkoxyalkyl and $R^{10}$—O—C(O)$R^7$; or
$R^4$ and $R^5$ together with the carbon atoms to which they are attached form a 6-membered unsaturated or saturated ring which may contain 1 heteroatom O,
wherein the ring is optionally substituted with one or two substituents independently selected from $R^9$, —O—$R^9$, —SO$_2$—$R^9$, —CO$_2$—$R^9$, cyano and halogen;
$R^6$ is hydrogen or alkyl;
$R^7$ is hydrogen, alkyl or alkoxyalkyl;
$R^8$ is in each case independently alkyl or haloalkyl;
$R^9$ is in each case independently selected from an saturated and/or unsaturated, acyclic and/or cyclic organic residue with up to 7 carbon atoms which may comprise one or two heteroatoms selected from N and O, which may be substituted by halogen, hydroxy, alkoxy, —O—C(O)$R^7$, carboxyester or carboxyamide;
$R^{10}$ is alkylene.

Further preferred are compounds of formula I, wherein $R^4$ and $R^5$ together with the carbon atoms to which they are attached form a 5- or 6-membered unsaturated or saturated ring which may contain 1 or 2 heteroatoms selected from N, O and S, wherein the ring is optionally substituted with one to three substituents independently selected from $R^9$, —O—$R^9$, —O—CO—$R^9$, —NR$^9$—CO—$R^9$, —S—$R^9$, —SO—$R^9$, —SO$_2$—$R^9$, —CO$_2$—$R^9$, —CON(R$^9$)$_2$, —R$^{10}$—O—$R^9$, —R$^{10}$—O—COR$^9$, —R$^{10}$—NR$^9$—COR$^9$, —R$^{10}$—S—$R^9$, —R$^{10}$—SO—$R^9$, —R$^{10}$—SO$_2$—$R^9$; —R$^{10}$—CO$_2$—$R^9$; —R$^{10}$—CON(R$^9$)$_2$, N(R$^9$)$_2$, cyano, nitro and halogen.

Other preferred compounds of formula I are those, wherein X is defined as N—$R^7$ or O in accordance with the above definition of $R^1$. Particularly preferred is $R^7$ in N—$R^7$ hydrogen, alkyl and alkoxyalkyl, and more preferably hydrogen, methyl and methoxyethyl.

Particularly preferred are compounds of formula I, wherein $R^4$ and $R^5$ together with the carbon atoms to which they are attached form a 5- or 6-membered unsaturated or saturated ring which may contain 1 or 2 heteroatoms selected from N, O and S, wherein the ring is optionally substituted with one to three substituents independently selected from $R^9$, —O—$R^9$, —O—CO—$R^9$, —NR$^9$—CO—$R^9$, —S—$R^9$, —SO—$R^9$, —SO$_2$—$R^9$, —CO$_2$—$R^9$, —CON(R$^9$)$_2$, —R$^{10}$—O—$R^9$, —R$^{10}$—O—COR$^9$, —R$^{10}$—NR$^9$—COR$^9$, —R$^{10}$—S—$R^9$, —R$^{10}$—SO—$R^9$, —R$^{10}$—SO$_2$—$R^9$; —R$^{10}$—CO$_2$—$R^9$; —R$^{10}$—CON(R$^9$)$_2$, N(R$^9$)$_2$, cyano, nitro and halogen.

Moreover, preferred are the compounds of formula I, wherein $R^2$ and $R^3$ are in each case independently selected from hydrogen, straight-chain or branched-chain $C_1$-$C_3$-alkyl, methoxy, phenyl, methoxymethyl, bromo and —S—$R^8$, wherein $R^8$ is alkyl or haloalkyl. More preferably, $R^2$ and $R^3$ are in each case independently selected from hydrogen, straight chain or branched-chain methyl, ethyl, isopropyl, methoxy, phenyl, methoxymethyl, bromo and —S—$R^8$, wherein $R^8$ is methyl or fluoroalkyl, wherein the fluoroalkyl is most preferably trifluoroalkyl, and still more preferably trifluoromethyl.

Further preferred are those compounds of formula I, wherein $R^2$ is hydrogen, methyl, ethyl, isopropyl, phenyl or methoxymethyl, and $R^3$ is methyl, ethyl, methoxy, bromo, methylthio or trifluoromethylthio.

Additionally preferred are the compounds of formula I, wherein $R^2$ and $R^3$ together with the carbon atoms to which they are attached form a 6-membered unsaturated ring, which may contain 1 heteroatom N, wherein the ring is substituted with one or two substituents independently selected from chloro, $R^9$ and —O—$R^9$, wherein $R^9$ is alkyl.

A more preferred aspect of the present invention are compounds according to formula I, wherein $R^2$ and $R^3$ together with the carbon atoms to which they are attached form a 6-membered unsaturated hydrocarbon ring, which may contain 1 heteroatom N, wherein the ring is substituted with one or two substituents independently selected from chloro, $R^9$ and —O—$R^9$, wherein $R^9$ is methyl.

Still more preferably, $R^2$ and $R^3$ together with the carbon atoms to which they are attached form a phenyl ring which is monosubstituted with methoxy or methyl or disubstituted with methoxy and chloro or they form a pyridinyl ring which is monosubstituted with methoxy.

Further preferred are those compounds according to formula I, wherein wherein $R^4$ and $R^5$ are independently selected from hydrogen, methyl, hydroxyethyl, methoxymethyl, methoxyethyl and $R^{10}$—O—C(O)$R^7$, wherein $R^{10}$ is alkylene and $R^7$ is alkyl. More preferred are those compounds, wherein $R^4$ and $R^5$ are independently selected from hydrogen, methyl, hydroxyethyl, methoxymethyl, methoxyethyl and $R^{10}$—O—C(O)$R^7$, wherein $R^{10}$ is ethylene and $R^7$ is methyl.

Further preferred are those compounds of formula I, wherein $R^4$ is methyl, hydroxyethyl, methoxyethyl, methoxymethyl or $R^{10}$—O—C(O)$R^7$, wherein $R^{10}$ is ethylene and $R^7$ is methyl. Further preferred are those compounds of formula I, wherein $R^5$ is hydrogen, methyl, methoxyethyl, hydroxyethyl or $R^{10}$—O—C(O)$R^7$, wherein $R^{10}$ is ethylene and $R^7$ is methyl.

Further preferred are those compounds according to formula I, wherein $R^4$ and $R^5$ together with the carbon atoms to which they are attached form a 6-membered unsaturated or saturated ring which may contain 1 heteroatom O, wherein the ring is optionally substituted with one or two substituents independently selected from $R^9$, —O—$R^9$, —SO$_2$—$R^9$, —CO$_2$—$R^9$, wherein $R^9$ is alkyl, alkoxy or aralkyl, wherein the alkyl is optionally substituted with hydroxy, carboxyester, carboxyamide or —O—C(O)$R^7$; cyano, chloro, fluoro and bromo.

Still further preferred are those compounds according to formula I, wherein $R^4$ and $R^5$ together with the carbon atoms to which they are attached form a 6-membered unsaturated or saturated ring which may contain 1 heteroatom O, wherein the ring is optionally substituted with one or two substituents independently selected from $R^9$, —O—$R^9$, —SO$_2$—$R^9$, —CO$_2$—$R^9$, wherein $R^9$ is methyl, ethyl, methoxy or benzyl, wherein methyl is optionally substituted with carboxyester, carboxyamide or —O—C(O)$R^7$ and ethyl is substituted with hydroxy; cyano, chloro, fluoro and bromo. More preferably, the carboxyester is carboxyethylester and the carboxyamide is acetamide.

Most preferably, $R^4$ and $R^5$ together with the carbon atoms to which they are attached form an unsubstituted dihydropyran ring or a phenyl ring, wherein the phenyl ring is unsubstituted or substituted with methoxy, methyl, chloro, benzyloxy, methoxyethoxy, hydroxyethoxy, oxyethylacetate, ethyloxyacetate, oxyacetamide, —CO$_2$— methyl, fluoro, bromo, chloro, cyano, —SO$_2$-methyl, dimethylisoxazolyl ring or pyridinyl ring.

Further preferred are those compounds according to formula I, wherein $R^6$ is hydrogen or methyl.

Further preferred are compounds of formula I, wherein $R^7$ is hydrogen, methyl or methoxyethyl.

Further preferred are compounds of formula I, wherein $R^8$ is in each case independently methyl or fluoroalkyl, more preferably trifluoroalkyl.

Another preferred aspect of the present invention are the compounds of formula I, wherein $R^9$ is in each case independently selected from methyl which is optionally substituted with chloro, carboxyamide or carboxyester; ethyl which is substituted with hydroxy, methoxy —O—C(O)$R^7$, wherein $R^7$ is alkyl; dimethylisoxazolyl; pyridinyl; and aralkyl. Still more preferably, the carboxyamide is acetamide, the carboxyester is carboxyethylester, the alkyl is methyl and the aralkyl is benzyl.

Another preferred aspect of the present invention are the compounds of formula I, wherein $R^{10}$ is ethylene.

Examples of preferred compounds of formula I are:
1. N-[(5-Bromo-1,3-thiazol-2-yl)carbamoyl]-5-methyl-1-benzothiophene-2-sulfonamide;
2. N-[(5-Bromo-1,3-thiazol-2-yl)carbamoyl]-1-benzothiophene-2-sulfonamide;
3. N-[(5-Bromo-1,3-thiazol-2-yl)carbamoyl]-5-fluoro-3-methyl-1-benzothiophene-2-sulfonamide;
4. N-[(5-Bromo-1,3-thiazol-2-yl)carbamoyl]-1-benzothiophene-3-sulfonamide;
5. 5-Bromo-N-[(5-bromo-1,3-thiazol-2-yl)carbamoyl]-3-methyl-1-benzothiophene-2-sulfonamide;
6. N-[(5-Bromo-1,3-thiazol-2-yl)carbamoyl]-6,7-dihydro-4H-thieno[3,2-c]pyran-2-sulfonamide;
7. N-[(5-Bromo-1,3-thiazol-2-yl)carbamoyl]-5-methoxy-1-benzothiophene-3-sulfonamide;
8. N-[(5-Bromo-1,3-thiazol-2-yl)carbamoyl]-1-methyl-1H-indole-2-sulfonamide;
9. N-[(5-Bromo-1,3-thiazol-2-yl)carbamoyl]-6-methoxy-1-benzothiophene-2-sulfonamide;
10. Methyl 3-({[(5-bromo-1,3-thiazol-2-yl)carbamoyl]amino}sulfonyl)-1-benzothiophene-5-carboxylate;
11. N-[(5-Bromo-1,3-thiazol-2-yl)carbamoyl]-5-methyl-1-benzothiophene-3-sulfonamide;
12. N-[(5-Bromo-1,3-thiazol-2-yl)carbamoyl]-5-chloro-1-benzothiophene-3-sulfonamide;
13. N-[(5-Bromo-1,3-thiazol-2-yl)carbamoyl]-5-chloro-1-benzothiophene-2-sulfonamide;
14. N-[(5-Bromo-1,3-thiazol-2-yl)carbamoyl]-7-methyl-1-benzothiophene-2-sulfonamide;
15. 7-Bromo-N-[(5-bromo-1,3-thiazol-2-yl)carbamoyl]-6-methoxy-1-benzothiophene-2-sulfonamide;
16. N-[(5-bromo-1,3-thiazol-2-yl)carbamoyl]-5-(3,5-dimethylisoxazol-4-yl)-1-benzothiophene-2-sulfonamide;
17. N-[(5-Bromo-1,3-thiazol-2-yl)carbamoyl]-5-methoxy-1-benzothiophene-2-sulfonamide;
18. N-[(5-Bromo-1,3-thiazol-2-yl)carbamoyl]-7-chloro-1-benzothiophene-3-sulfonamide;
19. N-[(5-Bromo-1,3-thiazol-2-yl)carbamoyl]-7-chloro-1-benzothiophene-2-sulfonamide;
20. N-[(5-Bromo-1,3-thiazol-2-yl)carbamoyl]-1H-indole-2-sulfonamide;
21. N-[(5-Bromo-1,3-thiazol-2-yl)carbamoyl]-7-(3,5-dimethylisoxazol-4-yl)-1-benzothiophene-2-sulfonamide;
22. N-[(5-Bromo-1,3-thiazol-2-yl)carbamoyl]-7-pyridin-4-yl-1-benzothiophene-2-sulfonamide;
23. N-[(5-Bromo-1,3-thiazol-2-yl)carbamoyl]-1-methyl-1H-indole-3-sulfonamide;
24. 5-(Benzyloxy)-N-[(5-bromo-1,3-thiazol-2-yl)carbamoyl]-1-methyl-1H-indole-3-sulfonamide;
25. Methyl 3-({[(5-bromo-1,3-thiazol-2-yl)carbamoyl]amino}sulfonyl)-1-methyl-1H-indole-5-carboxylate;
26. N-[(5-Bromo-1,3-thiazol-2-yl)carbamoyl]-5-fluoro-1-methyl-1H-indole-3-sulfonamide;
27. Methyl 3-({[(5-bromo-1,3-thiazol-2-yl)carbamoyl]amino}sulfonyl)-1-methyl-1H-indole-6-carboxylate;
28. 6-(Benzyloxy)-N-[(5-bromo-1,3-thiazol-2-yl)carbamoyl]-1-methyl-1H-indole-3-sulfonamide;
29. N-[(5-Bromo-1,3-thiazol-2-yl)carbamoyl]-6-cyano-1-methyl-1H-indole-3-sulfonamide;
30. N-[(5-Bromo-1,3-thiazol-2-yl)carbamoyl]-1-methyl-6-(methylsulfonyl)-1H-indole-3-sulfonamide;
31. N-[(5-Bromo-1,3-thiazol-2-yl)carbamoyl]-1-(2-methoxyethyl)-1H-indole-3-sulfonamide;
32. Methyl 3-({[(5-bromo-1,3-thiazol-2-yl)carbamoyl]amino}sulfonyl)-1-methyl-1H-indole-7-carboxylate;
33. N-[(5-Bromo-1,3-thiazol-2-yl)carbamoyl]-7-methoxy-1-methyl-1H-indole-3-sulfonamide;
34. 7-Bromo-N-[(5-bromo-1,3-thiazol-2-yl)carbamoyl]-1-methyl-1H-indole-3-sulfonamide;
35. N-[(5-Bromo-4-methyl-1,3-thiazol-2-yl)carbamoyl]-5-(methoxymethyl)-4-methylfuran-2-sulfonamide;
36. N-[(5-Bromo-1,3-thiazol-2-yl)carbamoyl]-5-(methoxymethyl)-4-methylfuran-2-sulfonamide;
37. 7-(Benzyloxy)-N-[(5-bromo-1,3-thiazol-2-yl)carbamoyl]-1-benzothiophene-2-sulfonamide;
38. N-[(5-bromo-1,3-thiazol-2-yl)carbamoyl]-7-(2-methoxyethoxy)-1-benzothiophene-2-sulfonamide;
39. N-[(5-bromo-1,3-thiazol-2-yl)carbamoyl]-7-methoxy-1-benzothiophene-2-sulfonamide;
40. N-[(5-bromo-1,3-thiazol-2-yl)carbamoyl]-7-methoxy-1-methyl-1H-indole-2-sulfonamide;
41. 7-(Benzyloxy)-N-[(5-bromo-1,3-thiazol-2-yl)carbamoyl]-1-methyl-1H-indole-3-sulfonamide;
42. N-[(5-bromo-1,3-thiazol-2-yl)carbamoyl]-7-(2-methoxyethoxy)-1-methyl-1H-indole-3-sulfonamide;
43. N-[(5-bromo-1,3-thiazol-2-yl)carbamoyl]-7-methoxy-1H-indole-3-sulfonamide;
44. 7-Methoxy-N-[(5-methoxy-1,3-thiazol-2-yl)carbamoyl]-1-methyl-1H-indole-3-sulfonamide;
45. N-[(5-Methoxy-1,3-benzothiazol-2-yl)carbamoyl]-5-(2-methoxyethyl)-4-methylthiophene-2-sulfonamide;
46. 2-{[3-({[(5-Methoxy-1,3-thiazol-2-yl)carbamoyl]amino}sulfonyl)-1-methyl-1H-indol-7-yl]oxy}ethyl acetate;
47. 7-(2-Hydroxyethoxy)-N-[(5-methoxy-1,3-thiazol-2-yl)carbamoyl]-1-methyl-1H-indole-3-sulfonamide;
48. 2-{[3-({[(5-Bromo-1,3-thiazol-2-yl)carbamoyl]amino}sulfonyl)-1-methyl-1H-indol-7-yl]oxy}ethyl acetate;
49. N-[(5-Bromo-1,3-thiazol-2-yl)carbamoyl]-7-(2-hydroxyethoxy)-1-methyl-1H-indole-3-sulfonamide;
50. Ethyl {[3-({[(5-bromo-1,3-thiazol-2-yl)carbamoyl]amino}sulfonyl)-1-methyl-1H-indol-7-yl]oxy}acetate;
51. 2-{[3-({[(5-Bromo-1,3-thiazol-2-yl)carbamoyl]amino}sulfonyl)-1-methyl-1H-indol-7-yl]oxy}acetamide;
52. 7-Methoxy-N-[(5-methoxy-4-methyl-1,3-thiazol-2-yl)carbamoyl]-1-methyl-1H-indole-3-sulfonamide;
53. 2-{[3-({[(5-Methoxy-4-methyl-1,3-thiazol-2-yl)carbamoyl]amino}sulfonyl)-1-methyl-1H-indol-7-yl]oxy}acetamide;
54. 5-Methoxy-N-[(5-methoxy-1,3-thiazol-2-yl)carbamoyl]-1-benzothiophene-2-sulfonamide;
55. 2-[5-({[(5-methoxy[1,3]thiazolo[5,4-b]pyridin-2-yl)carbamoyl]amino}sulfonyl)-3-methyl-2-thienyl]ethyl acetate;
56. 5-(2-Hydroxyethyl)-N-[(5-methoxy[1,3]thiazolo[5,4-b]pyridin-2-yl)carbamoyl]-4-methylthiophene-2-sulfonamide;
57. N-[(5-Bromo-4-ethyl-1,3-thiazol-2-yl)carbamoyl]-5-methylthiophene-3-sulfonamide;

58. N-[(5-Bromo-4-ethyl-1,3-thiazol-2-yl)carbamoyl]-5-(2-methoxyethyl)-4-methylthiophene-2-sulfonamide;
59. N-[(5-Bromo-4-ethyl-1,3-thiazol-2-yl)carbamoyl]-4-(2-methoxyethyl)-5-methylthiophene-2-sulfonamide;
60. N-[(5-Ethyl-4-methyl-1,3-thiazol-2-yl)carbamoyl]-5-(2-methoxyethyl)-4-methylthiophene-2-sulfonamide;
61. N-[(4-Ethyl-5-methoxy-1,3-thiazol-2-yl)carbamoyl]-5-methylthiophene-3-sulfonamide;
62. N-[(4,5-Diethyl-1,3-thiazol-2-yl)carbamoyl]-5-methylthiophene-3-sulfonamide;
63. N-[(4,5-Diethyl-1,3-thiazol-2-yl)carbamoyl]-5-(2-methoxyethyl)-4-methylthiophene-2-sulfonamide;
64. 2-[5-({[(5-Bromo-4-methyl-1,3-thiazol-2-yl)carbamoyl]amino}sulfonyl)-3-methyl-2-thienyl]ethyl acetate;
65. 5-Methyl-N-[(5-methyl-4-phenyl-1,3-thiazol-2-yl)carbamoyl]thiophene-3-sulfonamide;
66. 5-(2-Methoxyethyl)-4-methyl-N-[(5-methyl-4-phenyl-1,3-thiazol-2-)carbamoyl]thiophene-2-sulfonamide;
67. 2-[5-({[(4,5-Diethyl-1,3-thiazol-2-yl)carbamoyl]amino}sulfonyl)-3-methyl-2-thienyl]ethyl acetate;
68. 2-[5-({[(5-Ethyl-4-methyl-1,3-thiazol-2-yl)carbamoyl]amino}sulfonyl)-3-methyl-2-thienyl]ethyl acetate;
69. N-[(4,5-Diethyl-1,3-thiazol-2-yl)carbamoyl]-5-(2-hydroxyethyl)-4-methylthiophene-2-sulfonamide;
70. N-[(5-Ethyl-4-methyl-1,3-thiazol-2-yl)carbamoyl]-5-(2-hydroxyethyl)-4-methylthiophene-2-sulfonamide;
71. N-[(5-Ethyl-4-phenyl-1,3-thiazol-2-yl)carbamoyl-5-methylthiophene-3-sulfonamide;
72. N-[(5-Ethyl-4-phenyl-1,3-thiazol-2-yl)carbamoyl]-5-(2-methoxyethyl)-4-methylthiophene-2-sulfonamide;
73. 2-[3-Methyl-5-({[(5-methyl-4-phenyl-1,3-thiazol-2-yl)carbamoyl]amino}sulfonyl)-2-thienyl]ethyl acetate;
74. 2-[5-({[(5-Methoxy-4-methyl-1,3-thiazol-2-yl)carbamoyl]amino}sulfonyl)-3-methyl-2-thienyl]ethyl acetate;
75. 2-[5-({[(5-Ethyl-4-isopropyl-1,3-thiazol-2-yl)carbamoyl]amino}sulfonyl)-3-methyl-2-thienyl]ethyl acetate;
76. 5-(2-Hydroxyethyl)-4-methyl-N-[(5-methyl-4-phenyl-1,3-thiazol-2-yl)carbamoyl]thiophene-2-sulfonamide;
77. N-[(5-Ethyl-4-isopropyl-1,3-thiazol-2-yl)carbamoyl]-5-(2-methoxyethyl)-4-methylthiophene-2-sulfonamide;
78. N-[(5-Ethyl-4-isopropyl-1,3-thiazol-2-yl)carbamoyl]-5-methylthiophene-3-sulfonamide;
79. N-[(5-Ethyl-4-isopropyl-1,3-thiazol-2-yl)carbamoyl]-5-(2-hydroxyethyl)-4-methylthiophene-2-sulfonamide;
80. 2-[5-({[(5-Ethyl-4-phenyl-1,3-thiazol-2-yl)carbamoyl]amino}sulfonyl)-3-methyl-2-thienyl]ethyl acetate;
81. N-[(5-Ethyl-4-phenyl-1,3-thiazol-2-yl)carbamoyl]-5-(2-hydroxyethyl)-4-methylthiophene-2-sulfonamide;
82. N-{[4-Ethyl-5-(methylthio)-1,3-thiazol-2-yl]carbamoyl}-5-(2-methoxyethyl)4-methylthiophene-2-sulfonamide;
83. 2-{5-[({[4-Ethyl-5-(methylthio)-1,3-thiazol-2-yl]carbamoyl}amino)sulfonyl]-3-methyl-2-thienyl}ethyl acetate;
84. N-{[4-Ethyl-5-(methylthio)-1,3-thiazol-2-yl]carbamoyl}-5-(2-hydroxyethyl)-4-methylthiophene-2-sulfonamide;
85. 2-{3-Methyl-5-[({[4-methyl-5-(methylthio)-1,3-thiazol-2-yl]carbamoyl}amino)sulfonyl]-2-thienyl}ethyl acetate;
86. 5-(2-Hydroxyethyl)-4-methyl-N-{[4-methyl-5-(methylthio)-1,3-thiazol-2-yl]carbamoyl}thiophene-2-sulfonamide;
87. 2-{5-[({[4-(Methoxymethyl)-5-(methylthio)-1,3-thiazol-2-yl]carbamoyl}amino)sulfonyl]-3-methyl-2-thienyl}ethyl acetate;
88. 5-(2-Hydroxyethyl)-N-{[4-(methoxymethyl)-5-(methylthio)-1,3-thiazol-2-yl]carbamoyl}-4-methylthiophene-2-sulfonamide;
89. N-[(4-Methoxy-1,3-benzothiazol-2-yl)carbamoyl]-5-(2-methoxyethyl)-4-methylthiophene-2-sulfonamide;
90. 5-(2-Methoxyethyl)-N-[(5-methoxy[1,3]thiazolo[5,4-b]pyridin-2-yl)carbamoyl]-4-methylthiophene-2-sulfonamide;
91. 5-(2-Methoxyethyl)-4-methyl-N-[(4-methyl-1,3-benzothiazol-2-yl)carbamoyl]thiophene-2-sulfonamide;
92. N-[(7-Chloro-4-methoxy-1,3-benzothiazol-2-yl)carbamoyl]-5-(2-hydroxyethyl)-4-methylthiophene-2-sulfonamide;
93. 5-(2-Hydroxyethyl)-N-[(4-methoxy-1,3-benzothiazol-2-yl)carbamoyl]-4-methylthiophene-2-sulfonamide;
94. 5-(2-Hydroxyethyl)-4-methyl-N-[(4-methyl-1,3-benzothiazol-2-yl)carbamoyl]thiophene-2-sulfonamide;
95. N-[(5-Methoxy-4-methyl-1,3-thiazol-2-yl)carbamoyl]-5-methylthiophene-3-sulfonamide;
96. 5-(2-Methoxyethyl)-N-[(5-methoxy-4-methyl-1,3-thiazol-2-yl)carbamoyl]-4-methylthiophene-2-sulfonamide;
97. 5-(2-Methoxyethyl)-N-[(5-methoxy-1,3-thiazol-2-yl)carbamoyl]-4-methylthiophene-2-sulfonamide; and
98. 5-(2-Hydroxyethyl)-4-methyl-N-({4-methyl-5-[(trifluoromethyl)thio]-1,3-thiazol-2-yl}carbamoyl)thiophene-2-sulfonamide.

Particularly preferred examples of formula I are:
N-[(5-bromo-1,3-thiazol-2-yl)carbamoyl]-7-methoxy-1-methyl-1H-indole-3-sulfonamide;
N-[(5-bromo-1,3-thiazol-2-yl)carbamoyl]-5-(methoxymethyl)-4-methylfuran-2-sulfonamide;
N-[(5-bromo-1,3-thiazol-2-yl)carbamoyl]-7-methoxy-1-benzothiophene-2-sulfonamide;
7-methoxy-N-[(5-methoxy-1,3-thiazol-2-yl)carbamoyl]-1-methyl-1H-indole-3-sulfonamide;
2-{[3-({[(5-Bromo-1,3-thiazol-2-yl)carbamoyl]amino}sulfonyl)-1-methyl-1H-indol-7-yl]oxy}acetamide;
7-methoxy-N-[(5-methoxy-4-methyl-1,3-thiazol-2-yl)carbamoyl]-1-methyl-1H-indole-3-sulfonamide;
2-{[3-({[(5-methoxy-4-methyl-1,3-thiazol-2-yl)carbamoyl]amino}sulfonyl)-1-methyl-1H-indol-7-yl]oxy}acetamide;
5-(2-Hydroxyethyl)-N-[(5-methoxy[1,3]thiazolo[5,4-b]pyridin-2-yl)carbamoyl]-4-methylthiophene-2-sulfonamide;
N-[(5-ethyl-4-methyl-1,3-thiazol-2-yl)carbamoyl]-5-(2-methoxyethyl)-4-methylthiophene-2-sulfonamide;
N-[(4,5-diethyl-1,3-thiazol-2-yl)carbamoyl]-5-methylthiophene-3-sulfonamide;
N-[(5-ethyl-4-methyl-1,3-thiazol-2-yl)carbamoyl]-5-(2-hydroxyethyl)-4-methylthiophene-2-sulfonamide;
N-[(5-ethyl-4-isopropyl-1,3-thiazol-2-yl)carbamoyl]-5-methylthiophene-3-sulfonamide;
N-[(5-ethyl-4-phenyl-1,3-thiazol-2-yl)carbamoyl]-5-(2-hydroxyethyl)-4-methylthiophene-2-sulfonamide;
N-{[4-ethyl-5-(methylthio)-1,3-thiazol-2-yl]carbamoyl}-5-(2-hydroxyethyl)-4-methylthiophene-2-sulfonamide;
5-(2-hydroxyethyl)-4-methyl-N-{[4-methyl-5-(methylthio)-1,3-thiazol-2-yl]carbamoyl}thiophene-2-sulfonamide;
5-(2-hydroxyethyl)-N-{[4-(methoxymethyl)-5-(methylthio)-1,3-thiazol-2-yl]carbamoyl}-4-methylthiophene-2-sulfonamide;
5-(2-Methoxyethyl)-N-[(5-methoxy[1,3]thiazolo[5,4-b]pyridin-2-yl)carbamoyl]-4-methylthiophene-2-sulfonamide;
N-[(7-Chloro-4-methoxy-1,3-benzothiazol-2-yl)carbamoyl]-5-(2-hydroxyethyl)-4-methylthiophene-2-sulfonamide;

5-(2-Hydroxyethyl)-4-methyl-N-[(4-methyl-1,3-benzothiazol-2-yl)carbamoyl]thiophene-2-sulfonamide;

N-[(5-Methoxy-4-methyl-1,3-thiazol-2-yl)carbamoyl]-5-methylthiophene-3-sulfonamide; and 5-(2-hydroxyethyl)-4-methyl-N-({4-methyl-5-[(trifluoromethyl)thio]-1,3-thiazol-2-yl}carbamoyl)thiophene-2-sulfonamide.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

Compounds of formula I can be prepared as shown in in Schemes 1-7 and in the preparative examples 1-98. The starting material of formula II are known compounds or may be prepared by methods well known in the art. The process for the manufacture of compounds of formula Ia and Ib as defined above comprises reacting a compound of the formula IIa and IIb

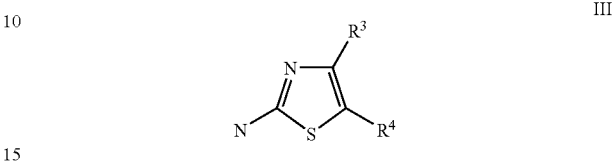

wherein $R^4$, $R^5$, and $R^6$ are as defined herein before with a phosgene derivative like diphosgene or triphosgene or, preferably, phenyl chloroformate, in the presence of a base like triethylamine or Hünig's base in a solvent like acetonitrile, and then reacting the thereby obtained intermediate without isolating it in the same pot at elevated temperature with an amine of general structure III

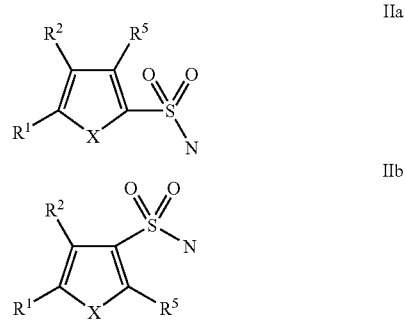

wherein $R^2$ and $R^3$ are as defined herein before. If desired, the compound obtained can be transformed into a pharmaceutically acceptable salt.

In more detail, the compounds of formula Ia and Ib can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure Ia and Ib and their respective intermediates is described in schemes 1 to 8.

Thiourea 1 is condensed with an α-bromo-ketone 2 (α-chloro-ketones are equally well suited) in an alcoholic solvent like ethanol at a temperature range of RT to reflux to furnish the 2-amino-thiazole III (scheme 1, step a). The latter are then combined with the intermediates 3a or 3b, generated from the primary sulfonamides IIa or IIb by treatment with phenyl chloroformate and a base like triethylamine in an inert solvent like acetonitrile at ambient temperature (scheme 1, step b) by allowing them to react together at slightly elevated temperature (50° C.—reflux) and for a prolonged period of time (2-24 h).

Scheme 1

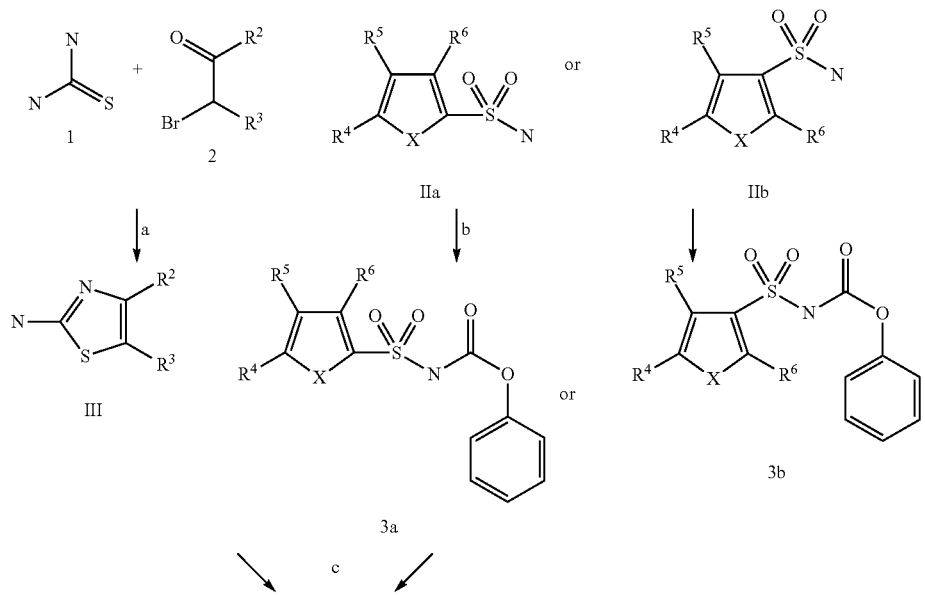

-continued

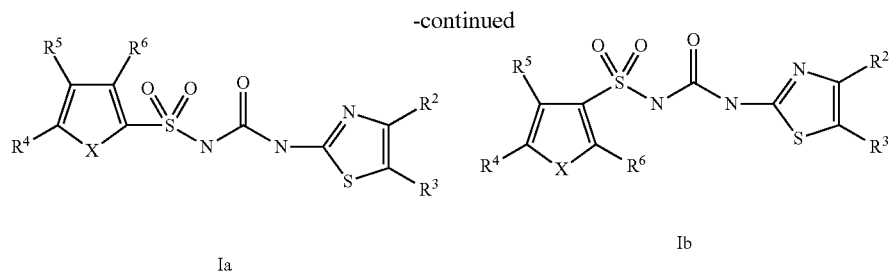

Ia

Ib

The α-bromo-ketones 3 can be prepared (for $R^3$=H) by regioselective kinetic deprotonation of ketone 1 and ensuing silylation of the resultant enolate (scheme 2, step a). The thereby obtained silyl-enolethers 2 can then be brominated to yield the necessary building blocks 3 (cf. *Eur. J. Org. Chem.* 2005, 4141, scheme 2, step b).

Scheme 2

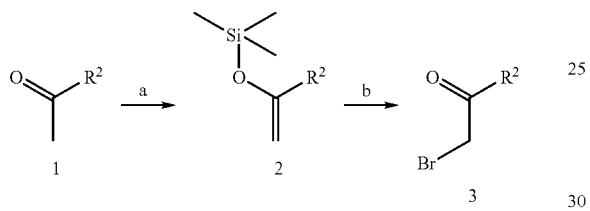

Aminothiazoles III ($R^3$=H) can be brominated, e.g., by treatment with bromine in aqueous sulfuric acid (cf. *Chem. Ber.* 1939, 72, 1470), or iodinated, e.g., by reacting them with chloroiodide in dichloromethane (cf. *Bull. Soc. Chim. Fr.* 1954, 1048) to yield compounds 1a or 1b (scheme 3, step a).

Scheme 3

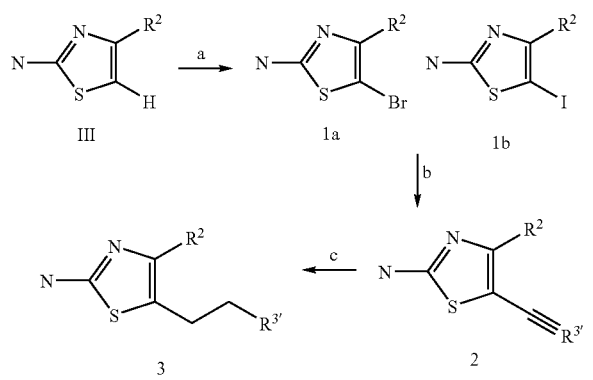

These intermediates are then used as such or are further elaborated, e.g., via palladium catalyzed coupling with acetylenes according to *Chem. Pharm. Bull.* 35, 823 (1987) to furnish derivatives 2. This reaction can be performed with free amine 1b or, optionally, after protection, e.g., as BOC-(benzyloxycarbonyl)-derivative (cf. *J. Med. Chem.* 2005, 48, 1886). Additional manipulation, e.g. hydrogenation over Pd on charcoal in an inert solvent like ethyl acetate at atmospheric pressure, and, if necessary, deprotection, e.g., by treatment with anhydrous HCl in dioxane or trifluoroacetic acid in $CH_2Cl_2$, delivers finally key building block 3 (scheme 3, step c).

5-Alkoxy-substituted aminothiazoles III ($R^3$=alkoxy) are best synthesized from the corresponding 5-bromo-analogues III ($R^3$=Br) by reacting them with freshly prepared sodium alkoxide in the corresponding alcohol as solvent between −20° C. and RT; interestingly enough, the presence of the 2-amino-group dramatically increases the rate of this reaction compared to the parent compound (cf. *J. C. S. Perkin II* 1976, 398, scheme 4).

Scheme 4

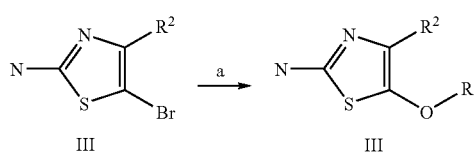

The analogous 5-thioalkoxy-aminothiazoles III ($R^3$=$SR^8$) can be obtained similarly. More convenient, however, is the procedure which involves first protection of the 4-monosubstituted 2-aminothiazole III ($R^3$=H), e.g., as BOC-derivative by treatment with $BOC_2O$ and 4-dimethylaminopyridine as catalyst (cf. *J. Med. Chem.* 2005, 48, 1886, scheme 5, step a), followed by double deprotonation with a strong base like nBuLi in THF/hexane between −78° and 0° C., and ensuing quenching of the dianion with a dialkyl- or diaryl-disulfide, to yield intermediate 2 (scheme 5, step b) which is eventually converted, albeit slowly, via standard acidic treatment to the envisaged target III ($R^3$=$SR^8$, cf. *J. Heterocyclic Chem.* 28, 1017 (1991), scheme 5, step c).

Scheme 5

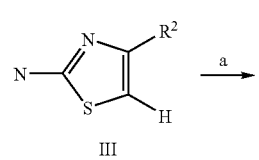

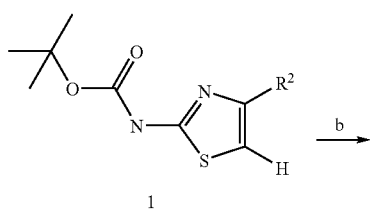

-continued

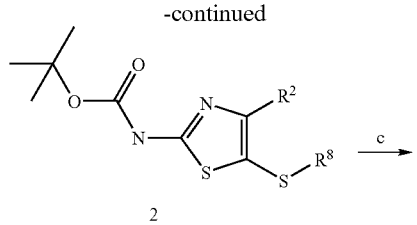
2

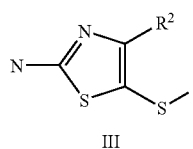
III

The building blocks IIa can be synthesized from the precursors 1, dependent upon the different residues $R^4$, $R^5$, and $R^6$, either by deprotonation with a strong base, e.g., nBuLi or tBuLi in an inert solvent like diethyl ether or tetrahydrofuran, followed by quenching of the intermediate organolithium species with sulfur dioxide to form compound 2 (scheme 6, step a) and transforming this compound via chlorination, e.g., with oxalyl chloride or thionyl chloride, into the corresponding sulfonyl chloride 3 (scheme 6, step b) and reacting the latter, finally, with ammonia into IIa (scheme 6, step c). Alternatively, compound 2 can be transformed directly into IIa by reacting it with hydroxylamine-O-sulfonic acid (scheme 6, step d, cf. *Synthesis* 1986 (12), 1031). In a third variant, aromatic bromide 4 can be subjected to a metal/halogen exchange, e.g., by treatment with an alkyl lithium compound like nBuLi or tBuLi, and proceeding as described above by quenching the aryl-Li intermediate with $SO_2$ (scheme 6, step e).

Scheme 6

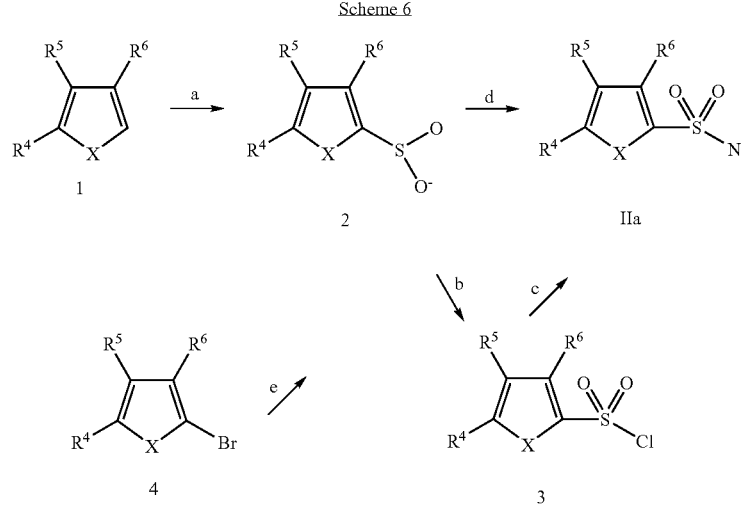

The building blocks IIb can be obtained from the bromide 1 in perfect analogy as described above (scheme 7, step a-d) or, often more convenient, by direct sulfonation with sulfur trioxide N,N-dimethylformamide complex (cf. *J. Org. Chem.* 47, 179 (1982)), followed by chlorination and reaction with ammonia (scheme 7, step e).

Scheme 7

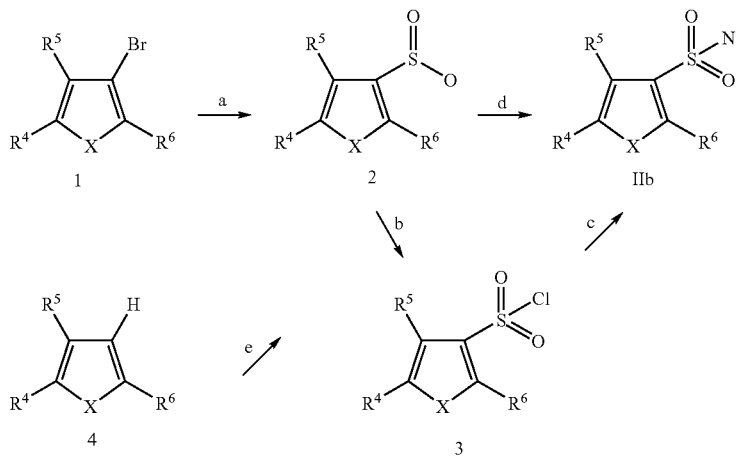

Substituted aminobenzothiazoles and their aza anlaogues such as pyrido-thiazoles pyrimido-thiazoles, pyrazino-thiazoles etc, are also useful intermediates towards the synthesis of desired compounds of formula I. To date, numerous methods have been described for the preparation of such fused ring systems and examples of their syntheses are shown in scheme 8. The cyclization of an aryl thiourea by the action of molecular bromine is a versatile method (cf. *J. Org. Chem.* 49, 497 (1984)). Similarly, the reaction of a substituted 3-aminopyridine 1 with potassium thiocyanate in acetic acid is known to yield the thiourea 2 (scheme 8, step a) which upon treatment with bromine affects the cyclization to amine III (scheme 8, step b). Further bicyclic systems can be prepared by using functionalized pyrazines and pyrimidines (cf. *Heterocycles* 26, 689 (1987) and patent application WO2007007886). Amino-bromopyrimidine 3 and amino-bromopyrazine 5 are reacted with isothiocyanates EW-NCS (e.g., EW=benzoyl or CO$_2$Et) in acetone or methanol as solvents under refluxing conditions resulting in direct cyclization to 4 and 6 without isolation of the corresponding thiourea intermediates (scheme 8, step c and e, respectively). Subsequent removal of benzoyl or carbamates groups under basic conditions (e.g., NaOMe or NaOH, scheme 8, step d and f, respectively) produces the requisite amine intermediates for the preparation of compounds of formula I. Alternatively, a two step process can be followed transforming amino-pyrazine 7 into the corresponding thiourea derivative 8 (scheme 8, step g), followed by acid catalyzed, preferably aqueous HCl, cyclisation (scheme 8, step h).

Scheme 8

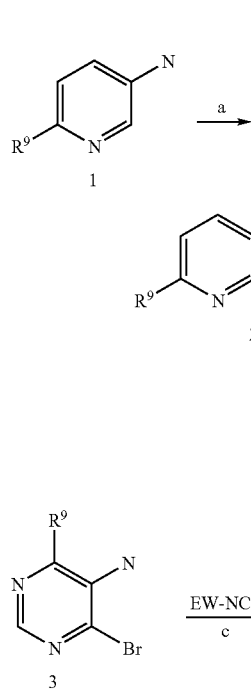

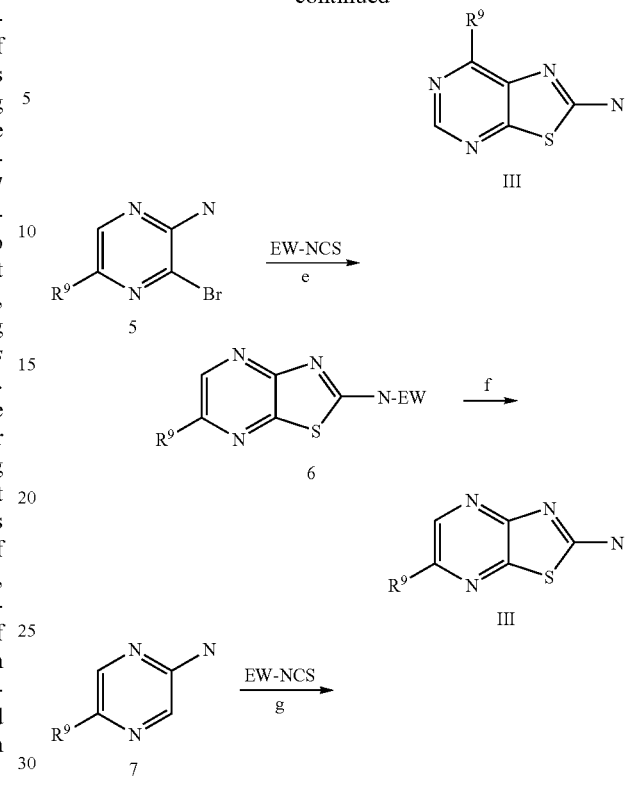

A preferred process for the preparation of a compound of formula I

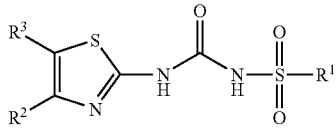
(I)

as described before comprises one of the following reactions, wherein $R^1$ to $R^6$ are defined as before:

a) reaction of a compound according to formula IIa or IIb

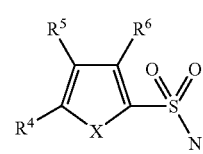
IIa

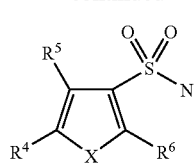

in the presence of a base, phenyl chloroformate and a compound according to formula III

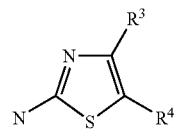

Preferred intermediates are:
1) 5-Methyl-benzo[b]thiophene-2-sulfonic acid amide
2) 6-Methoxy-benzo[b]thiophene-2-sulfonic acid amide
3) 7-Methyl-benzo[b]thiophene-2-sulfonic acid amide
4) 7-Methoxy-1-methyl-1H-indole-3-sulfonic acid amide
5) 5-(2-Methoxy-ethyl)-4-methyl-thiophene-2-sulfonic acid amide
6) Acetic acid 2-(3-methyl-5-sulfamoyl-thiophen-2-yl)-ethyl ester
7) 5-Methyl-thiophene-3-sulfonic acid amide
8) 5-Methoxy-4-methyl-2,3-dihydro-thiazol-2-ylamine
9) 4-Ethyl-5-methoxy-2,3-dihydro-thiazol-2-ylamine
10) 4-Methyl-5-methylsulfanyl-2,3-dihydro-thiazol-2-ylamine
11) 4-Ethyl-5-methylsulfanyl-2,3-dihydro-thiazol-2-ylamine
12) 4,5-Diethyl-2,3-dihydro-thiazol-2-ylamine
13) 5-Ethyl-4-methyl-2,3-dihydro-thiazol-2-ylamine
14) 5-Ethyl-4-phenyl-2,3-dihydro-thiazol-2-ylamine
15) 5-Methyl-4-phenyl-2,3-dihydro-thiazol-2-ylamine
16) 5-Ethyl-4-isopropyl-2,3-dihydro-thiazol-2-ylamine
17) 5-Bromo-4-ethyl-2,3-dihydro-thiazol-2-ylamine
18) 4-Methyl-5-trifluoromethylsulfanyl-2,3-dihydro-thiazol-2-ylamine
19) 4-Methoxymethyl-5-methylsulfanyl-2,3-dihydro-thiazol-2-ylamine
20) 4-Methoxy-2,3-dihydro-benzothiazol-2-ylamine
21) 4-Methyl-2,3-dihydro-benzothiazol-2-ylamine
22) 7-Chloro-4-methoxy-2,3-dihydro-benzothiazol-2-ylamine
23) Acetic acid 2-(1-methyl-3-sulfamoyl-1H-indol-7-yloxy)-ethyl ester
24) 7-(2-Methoxy-ethoxy)-1-methyl-1H-indole-3-sulfonic acid amide
25) 7-(2-Methoxy-ethoxy)-benzo[b]thiophene-2-sulfonic acid amide and
26) 5-Methoxy-thiazolo[5,4-b]pyridin-2-ylamine The compounds of formula I as described above for use as therapeutically active substance are a further object of the invention.

A further object of the invention are the compounds according to formula I for the preparation of medicaments for the prophylaxis and/or therapy of illnesses which are caused by disorders associated with the enzyme Fructose-1,6-bisphosphatase, preferably Diabetes Mellitus Type II, Diabetes Mellitus Type I, Diabetes Mellitus Type III, Impaired Fasting Glucose (IFG), Impaired Glucose Tolerance (IGT), diabetic complications or ischemia.

Likewise preferred is a pharmaceutical composition comprising a compound of formula I as described and a therapeutically inert carrier.

A further preferred embodiment of the invention is the use of a compound according to formula I as described for the preparation of medicaments for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischemia and particularly preferred for the treatment and/or prophylaxis of Diabetes Mellitus Type II or Diabetes Mellitus Type I.

A further object of the present invention is a compound according to formula I, when manufactured according to any one of the described processes.

Likewise preferred is a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischemia, which method comprises administering an effective amount of a compound of formula I as described. Preferred is this method for the treatment and/or prophylaxis of Diabetes Mellitus Type II or Diabetes Mellitus Type I.

Assay Procedures
FBPase Assay Description:
The following tests were carried out for evaluating the inhibitory activity of the compounds of the present invention against human liver FBPase (Swissprot Data base reference P09467, entry F16P_HUMAN).

Enzyme Preparation:
Human liver FBPase cDNA (NM_000507) was purchased from Origene Technologies, Inc, subcloned in a vector for expression in $E.\ Coli.$, and sequenced. Recombinant human liver FBPase (hlFBPase) was purified according to the following protocol that uses heat denaturation similarly to that described by El-Maghrabi et. al. [El-Maghrabi, M. R. et al. "Isolation of a human liver fructose-1,6-bisphosphatase cDNA and expression of the protein in $Escherichia\ coli$." J Biol Chem 268:9466-9472, 1993.]. Briefly, $E.\ coli$ cells, transiently expressing very high levels of soluble and active human liver FBPase, were suspended in 20 mM Tris-HCl pH 7.5, 1 mM EDTA, 1 mM DTT and were lysed by French press. The soluble extract was heat denatured at 65° C. for 5 min, and insoluble, denatured proteins were removed by centrifugation. The extract was then applied to a BioRad Macro-Prep High Q column equilibrated with 20 mM Tris-HCl pH 7.5, 1 mM EDTA, 1 mM DTT and the flow-through (containing FBPase activity) was collected and applied to a BioRad Macro-Prep HS column equilibrated with 20 mM HEPES pH 7.2, 1 mM DTT. A gradient of increasing NaCl concentration was then applied to the HS column and fractions were collected. Fractions containing active FBPase were pooled and further purified by size exclusion chromatography on a Sephacryl S200 column equilibrated in 20 mM Tris-HCl pH 7.5, 150 mM NaCl, 1 mM EDTA, 1 mM DTT. Purity of the enzyme preparation was >90% as assessed by Mass spectrometry.

In Vitro Activity:
Recombinant human liver FBPase (hlFBPase) activity was assayed through measuring the inorganic phosphate release that results from the hydrolysis of Fructose-1,6-bisphosphate by the enzyme. As described by Baykov A. A. et al. in [Baykov A. A et al., "Malachite Green procedure for orthophosphate determination and its use in alkaline phosphatase-based enzyme immunoassays". Anal. Biochem., 171:266-270, 1988], inorganic phosphate can be readily quantified by spectrophotometry at 620 nm after complexation with ammonium molybdate/malachite green reagent. Enzymatic reaction was carried out with modifications of the procedure described by Wright S. W. et al. [Wright S. W. et al., "Anilinoquinazoline inhibitors of Fructose-1,6-bisphosphatase bind to a novel allosteric site: synthesis, in vitro characterization, and X-ray crystallography". J. Med. Chem. 45:3865-3877, 2002]. Specifically, the reaction was carried out in 96 well plates in a final volume of 100 µl in the presence or in the absence of allosteric inhibitors. Reaction was started adding 25 ng of hlFBPase to the reaction mixture containing 50 mM HEPES-KOH buffer pH 7.2, 2 mM $MgCl_2$, 2 mM EDTA, 1 mM DTT, 50 µM fructose-1,6-bisphosphate and 1% DMSO. After 50 minutes incubation at room temperature, the phosphate released was allowed to form a colored complex for 10 min by adding 150 µl of ammonium molybdate/malachite green reagent containing 0.03% malachite green, 0.2% ammonium molybdate, 0.05% Triton X-100 and 0.7 M $H_2SO_4$ in water that was stirred for 30 min at room temperature and filtered through 0.2 µm filter. Under these conditions, the assay was linear with time and able to detect FBPase inhibition after spectrophotometric read-out at 620 nm.

Results obtained in the assay above using representative compounds of the invention as the test compounds are shown in the following table:

| Compound: Example | FBPase assay $IC_{50}$ (uM) |
|---|---|
| 1 | 0.089 |
| 2 | 0.434 |
| 3 | 2.732 |
| 4 | 0.212 |
| 5 | 1.465 |
| 6 | 0.528 |
| 7 | 0.122 |
| 8 | 1.105 |
| 9 | 0.088 |
| 10 | 0.446 |
| 11 | 0.624 |
| 12 | 0.37 |
| 13 | 0.111 |
| 14 | 0.161 |
| 15 | 0.141 |
| 16 | 0.83 |
| 17 | 0.167 |
| 18 | 0.208 |
| 19 | 0.268 |
| 20 | 0.134 |
| 21 | 0.447 |
| 22 | 0.44 |
| 23 | 0.385 |
| 24 | 0.683 |
| 25 | 0.731 |
| 26 | 0.341 |
| 27 | 0.45 |
| 28 | 0.363 |
| 29 | 0.74 |
| 30 | 0.523 |
| 31 | 2.253 |
| 32 | 0.653 |
| 33 | 0.071 |
| 34 | 0.296 |
| 35 | 0.258 |
| 36 | 0.315 |
| 37 | 0.972 |
| 38 | 0.179 |
| 39 | 0.105 |
| 40 | 0.329 |
| 41 | 0.124 |
| 42 | 0.375 |
| 43 | 4.06 |
| 44 | 1.316 |
| 45 | 0.402 |
| 46 | 3.501 |
| 47 | 0.734 |
| 48 | 0.429 |
| 49 | 0.104 |
| 50 | 0.212 |
| 51 | 0.137 |
| 52 | 0.771 |
| 53 | 0.764 |
| 54 | 1.283 |
| 55 | 0.616 |
| 56 | 0.534 |
| 57 | 0.188 |
| 58 | 0.155 |
| 59 | 0.434 |
| 60 | 0.341 |
| 61 | 0.466 |
| 62 | 0.214 |
| 63 | 0.393 |
| 64 | 0.188 |
| 65 | 0.3 |
| 66 | 0.16 |
| 67 | 0.215 |
| 68 | 0.149 |
| 69 | 0.34 |
| 70 | 0.417 |
| 71 | 0.159 |
| 72 | 0.224 |
| 73 | 0.128 |
| 74 | 0.454 |
| 75 | 0.256 |
| 76 | 0.28 |
| 77 | 0.366 |
| 78 | 0.168 |
| 79 | 0.188 |
| 80 | 0.161 |
| 81 | 0.102 |
| 82 | 0.144 |
| 83 | 0.134 |
| 84 | 0.078 |
| 85 | 0.16 |
| 86 | 0.071 |
| 87 | 0.501 |
| 88 | 0.369 |
| 89 | 0.263 |
| 90 | 0.842 |
| 91 | 0.375 |
| 92 | 0.038 |
| 93 | 0.141 |
| 94 | 0.064 |
| 95 | 0.594 |
| 96 | 0.637 |
| 97 | 0.652 |
| 98 | 0.177 |

Compounds as described above have $IC_{50}$ values of 1.0 µM to 10 nM; preferred compounds have $IC_{50}$ values of 500 to 10 nM. More preferred compounds have $IC_{50}$ values of 200 to 10 nM. These results have been obtained by using the foregoing test.

In Vivo Activity:

Glucose lowering activity of representative compounds of the present invention was demonstrated after acute treatment in male adult and diabetic db/db mice. db/db mice (12-20 weeks of age) were purchased from Jackson laboratories and time-course effect of compounds on blood glucose levels was measured from tail vein samplings using fluorometric method (Glucotrend systems (Roche AG)).

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), as aerosol formulations or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used e.g. for the prophylaxis and/or treatment of Diabetes Mellitus Type II, Diabetes Mellitus Type I, Diabetes Mellitus Type III, Impaired Fasting Glucose (IFG), Impaired Glucose Tolerance (IGT), diabetic complications or ischemia. The dosage can vary in wide limits and will, of course, be fitted to the individual requirements in each particular case. In general, in the case of oral administration a daily dosage of about 0.1 mg to 100 mg per kg body weight, preferably about 0.5 mg to 10 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

N-[(5-Bromo-1,3-thiazol-2-yl)carbamoyl]-5-methyl-1-benzothiophene-2-sulfonamide

To a suspension of 5-methyl-benzo[b]thiophenesulfonyl chloride (Maybridge, CAS: 90273-30-6, 0.37 g) in acetonitrile (5.0 mL) were added sodium cyanate (0.163 g) in one portion and pyridine (0.60 mL). The reaction mixture was stirred at rt for 3 h, then 2-amino-5-bromothiazole hydrobromide (0.286 g) was added in one portion. The mixture was stirred at rt for 4 h and quenched with 70% acetic acid (2.4 mL) and water (4.0 mL). The suspension was filtered, washed with waterlethanol and water, dried over $P_2O_5$ under high vacuum to obtain the desired compound (0.372 g) as a creamy solid. MS (ISN): m/e 430.1, 432.0 (M–H)$^-$

Example 2

N-[(5-Bromo-1,3-thiazol-2-yl)carbamoyl]-1-benzothiophene-2-sulfonamide

The title compound was prepared in analogy to the procedure described in Example 1 starting from benzo[b]thiophene-2-sulfonyl chloride (Maybridge, CAS: 90001-64-2) to obtain the desired compound as a creamy solid. MS (ISN): m/e 416.1, 418.0 (M–H)$^-$

Example 3

N-[(5-Bromo-1,3-thiazol-2-yl)carbamoyl]-5-fluoro-3-methyl-1-benzothiophene-2-sulfonamide The title compound was prepared in analogy to the procedure described for Example 1 starting from 5-fluoro-3-methyl-benzo[b]thiophene-2-sulfonyl chloride (Apollo, CAS: 404964-34-7) to obtain the desired compound as a brownish solid. MS (ISN): m/e 447.8, 449.9 (M–H)$^-$

Example 4

N-[(5-Bromo-1,3-thiazol-2-yl)carbamoyl]-1-benzothiophene-3-sulfonamide

The title compound was prepared in analogy to the procedure described for Example 1 starting from benzo[b]thiophene-3-sulfonyl chloride (Maybridge, CAS: 18494-87-6) to obtain the desired compound as a colourless solid. MS (ISN): m/e 416.1, 418.0 (M–H)$^-$

Example 5

5-Bromo-N-[(5-bromo-1,3-thiazol-2-yl)carbamoyl]-3-methyl-1-benzothiophene-2-sulfonamide The title compound was prepared in analogy to the procedure described for Example 1 starting from 5-bromo-3-methyl-benzo[b]thiophene-2-sulfonyl chloride (Buttpark, CAS: 338797-11-8) to obtain the desired compound as a brownish solid. MS (ISN): m/e 510.0, 512.0 (M–H)$^-$

Example 6

N-[(5-Bromo-1,3-thiazol-2-yl)carbamoyl]-6,7-dihydro-4H-thieno[3,2-c]pyran-2-sulfonamide i) 6,7-Dihydro-4H-thieno[3,2-c]pyran-2-sulfonyl chloride To a suspension of sulfur trioxide dimethylformamide complex (1.84 g, 12 mmol) in 1,2-dichloroethane (10 mL) was added 6,7-dihydro-4H-thieno[3,2-c]pyran (Yun, Sangmin; Kim, Eun Sook; Kim, Hee Seock; Ha, Tae Hee; Suh, Kwee-Hyun; Lee, Gwan Sun, WO 2005087779, 1.4 g, 10 mmol). The reaction mixture was stirred at rt for 1 h, thionyl chloride (1.55 g, 12 mmol) was added, and the mixture was stirred at 55-60° C. for 3-4 h and chromatographed directly on silica gel using heptane/ethyl acetate or dichloromethane/ethyl acetate as eluents to obtain 6,7-dihydro-4H-thieno[3,2-c]pyran-2-sulfonyl chloride (2.17 g) a light yellow solid.

MS (EI): m/e 238.1 (H)

ii) N-[(5-Bromo-1,3-thiazol-2-yl)carbamoyl]-6,7-dihydro-4H-thieno[3,2-c]pyran-2-sulfonamide amide.

The title compound was prepared in analogy to the procedure described for Example 1 starting from 6,7-dihydro-4H-thieno[3,2-c]pyran-2-sulfonyl chloride to obtain the desired compound as a yellowish solid. MS (ISN): m/e 423.9, 425.9 (M+H)⁻

Example 7

N-[(5-Bromo-1,3-thiazol-2-yl)carbamoyl]-5-methoxy-1-benzothiophene-3-sulfonamide i) 5-Methoxy-benzo[b]thiophene-3-sulfonyl chloride This compound was prepared in analogy to the procedure described for Example 6a starting from 5-methoxy-benzo[b]thiophene (Marez-Silanes, S., Journal of Heterocyclic Chemistry (2001), 38(6), 1469) to obtain 5-methoxy-benzo[b]thiophene-3-sulfonyl chloride as a yellow solid. MS (ISP) m/e 263.1 (M+H)⁺ ii) N-[(5-bromo-1,3-thiazol-2-yl)carbamoyl]-5-methoxy-1-benzothiophene-3-sulfonamide The title compound was prepared in analogy to the procedure described for Example 1 starting from 5-methoxy-benzo[b]thiophene-3-sulfonyl chloride to obtain the desired compound as a creamy solid. MS (ISN): m/e 445.9, 447.7 (M–H)⁻

Example 8

N-[(5-Bromo-1,3-thiazol-2-yl)carbamoyl]-1-methyl-1H-indole-2-sulfonamide

The title compound was prepared in analogy to the procedure described for Example 1 starting from 1-methyl-1H-indole-2-sulfonyl chloride (Chan, Ming F.; Raju, Bore G., US5594021) to obtain the desired compound as a creamy solid. MS (ISN): m/e 413.0, 415.1, (M–H)⁻

Example 9

N-[(5-Bromo-1,3-thiazol-2-yl)carbamoyl]-6-methoxy-1-benzothiophene-2-sulfonamide The title compound was prepared in analogy to the procedure described for Example 1 starting from 6-methoxy-benzo[b]thiophene-2-sulfonyl chloride (Graham, Samuel L.; Shepard, Kenneth L., J. Med. Chem. (1989), 32(12), 2548-54) to obtain the desired compound as a creamy solid. MS (ISN): m/e 446.0, 447.8, (M–H)⁻

Example 10

Methyl-3-({[(5-bromo-1,3-thiazol-2-yl)carbamoyl]amino}sulfonyl)-1-benzothiophene-5-carboxylate i) 3-Chlorosulfonyl-benzo[b]thiophene-5-carboxylic acid methyl ester To a solution of benzo[b]thiophene-5-carboxylic acid methyl ester (Hideki, T., Tamai, Y. WO2002100850, 0.39 g, 2 mmol) in 1,2-dichloroethane (5 mL) was added sulfur trioxide dimethylformamide complex (0.375 g, 2.4 mmol). The reaction mixture was stirred at 70° C. for 3 h, and thionyl chloride (0.31 g, 2.6 mmol) was added. The mixture was stirred at 80° C. for 3 h, cooled down and chromatographed on silica gel using dichloromethane/ethyl acetate as eluent to obtain 3-chlorosulfonyl-benzo[b]thiophene-5-carboxylic acid methyl ester (0.20 g) as a colourless solid. MS (ISP): m/e 308.0 (M+NH₄)⁺ ii) Methyl-3-({[(5-bromo-1,3-thiazol-2-yl)carbamoyl]amino}sulfonyl)-1-benzothiophene-5-carboxylate The title compound was prepared in analogy to the procedure described for Example 1 starting from 3-chlorosulfonyl-benzo[b]thiophene-5-carboxylic acid methyl ester to obtain the desired compound as a brownish solid. MS (ISN): m/e 474.1, 476.2 (M–H)⁻

Example 11

N-[(5-Bromo-1,3-thiazol-2-yl)carbamoyl]-5-methyl-1-benzothiophene-3-sulfonamide

The title compound was prepared in analogy to the procedure described in Example 1 starting from 5-methyl-benzo[b]thiophene-3-sulfonyl chloride (Pailer, M., Romberger, E., Monatshefte für Chemie, 92, 677-683, (1961)) to obtain the desired compound as a colourless solid. MS (ISN): m/e 430.2, 432.3 (M–H)⁻

Example 12

N-[(5-Bromo-1,3-thiazol-2-yl)carbamoyl]-5-chloro-1-benzothiophene-3-sulfonamide i) 5-Chloro-benzo[b]thiophene-3-sulfonyl chloride To a solution of 5-chloro-benzo[b]thiophene (Synchem, 1.0 g, 6 mmol) in 1,2-dichloroethane (10 mL) was added sulfur trioxide dimethylformamide complex (1.1 g, 7.2 mmol). The reaction mixture was stirred at 85° C. for 3 h, cooled down to about 50° C., and thionyl chloride (0.92 g, 7.8 mmol) was added. The mixture was further stirred at 80° C. for 1 h, cooled down and chromatographed on silica gel using heptane/ethyl acetate as eluent to obtain 5-chloro-benzo[b]thiophene-3-sulfonyl chloride (1.25 g) as colorless crystals. MS (EI) m/e 265.8 (M)

ii) N-[(5-Bromo-1,3-thiazol-2-yl)carbamoyl]-5-chloro-1-benzothiophene-3-sulfonamide The title compound was prepared in analogy to the procedure described in Example 1 starting from 5-chloro-benzo[b]thiophene-3-sulfonyl chloride to obtain the desired compound as a creamy solid. MS (ISN): m/e 449.9, 451.8 (M–H)⁻

Example 13

N-[(5-Bromo-1,3-thiazol-2-yl)carbamoyl]-5-chloro-1-benzothiophene-2-sulfonamide

The title compound was prepared in analogy to the procedure described in Example 1, starting from 5-chloro-benzo[b]thiophene-2-sulfonyl chloride (Komoriya, Satoshi; Haginoya, Noriyasu, Bioorganic & Medicinal Chemistry (2005), 13(12), 3927-3954) to obtain the desired compound as a brownish solid. MS (ISN): m/e 450.2, 452.1 (M−H)⁻

Example 14

N-[(5-Bromo-1,3-thiazol-2-yl)carbamoyl]-7-methyl-1-benzothiophene-2-sulfonamide i) 7-Methyl-benzo[b]thiophene-2-sulfonyl chloride This compound was prepared in analogy to the procedure described in Example 15ii) starting from 7-methyl-benzo[b]thiophene (CAS: 14315-15-2) to obtain the desired compound as a yellowish solid. MS (EI) m/e 246.0 (M)

ii) N-[(5-Bromo-1,3-thiazol-2-yl)carbamoyl]-7-methyl-1-benzothiophene-2-sulfonamide The title compound was prepared in analogy to the procedure described in Example 1 starting from 7-methyl-benzo[b]thiophene-2-sulfonyl chloride to obtain the desired compound as a brownish solid. MS (ISN): m/e 430.0, 431.9 (M−H)⁻

Example 15

7-Bromo-N-[(5-bromo-1,3-thiazol-2-yl)carbamoyl]-6-methoxy-1-benzothiophene-2-sulfonamide i) 2,7-Dibromo-6-methoxy-benzo[b]thiophene To a suspension of 6-methoxy-benzo[b]thiophene (Hideki, T., Tamai, Y. WO2002100850; 2.0 g, 12.2 mmol), and sodium acetate (1.51, 18.5 mmol) in dichloromethane (30 mL) was added dropwise bromine (2.02 g, 25.5 mmol) over 5 minutes at 5° C. The reaction mixture was stirred at rt for 5 h, quenched with ice/water, and extracted with dichloromethane. The organics were washed with brine, dried and concentrated. The residue was chromatographed over silica gel using heptane/ethyl acetate as eluent to obtain 2,7-dibromo-6-methoxy-benzo[b]thiophene (1.3 g) as an off-white solid. MS (EI): m/e 321.7 (M).

ii) 7-Bromo-6-methoxy-benzo[b]thiophene-2-sulfonyl chloride

To a solution of 2,7-dibromo-6-methoxy-benzo[b]thiophene (1.1 g, 3.4 mmol) in diethyl ether (40 mL) was added dropwise at −75° C. n-BuLi (1.6N, 2.35 mL, 3.75 mmol). The reaction mixture was stirred at −75° C. for 1 h, then a stream of sulfur dioxide was passed over the surface of the solvent until the reaction was no more exothermic. The suspension was then stirred at rt for 1 h and concentrated under vacuum. The residue was quenched with sat. sodium bicarbonate-solution (30 mL), and at 0-5° C. N-chlorosuccinimide (0.525 g, 3.95 mmol) was added. The mixture was stirred at rt for 1 h, quenched with water, and extracted with ethyl acetate. The organic phases were dried and concentrated. The residue was chromatographed on silica gel using heptane/ethyl acetate as eluent to obtain 7-bromo-6-methoxy-benzo[b]thiophene-2-sulfonyl chloride (0.57 g). MS (EI) m/e 339.9 (M)

iii) 7-Bromo-N-[(5-bromo-1,3-thiazol-2-yl)carbamoyl]-6-methoxy-1-benzothiophene-2-sulfonamide The title compound was prepared in analogy to the procedure described in Example 1 starting from 7-bromo-6-methoxy-benzo[b]thiophene-2-sulfonyl chloride to obtain the desired compound as a brownish solid. MS (ISN): m/e 526.2, 528.1 (M−H)⁻

Example 16

N-[(5-bromo-1,3-thiazol-2-yl)carbamoyl]-5-(3,5-dimethylisoxazol-4-yl)-1-benzothiophene-2-sulfonamide i) 4-Benzo[b]thiophen-5-yl-3,5-dimethyl-isoxazole To a solution of 5-bromo-1-benzothiophene (ABCR, CAS: 133150-64-8, 1.0 6 g, 5.0 mmol) in dimethoxyethane (60 mL) and ethanol (6.0 mL) was added 3,5-dimethyl-4-isoxazoylboronic acid (1.0 g, 7.5 mmol), and 2 m sodium carbonate (2.0 mL). The reaction mixture was degassed 2-3 times, tetrakis-(triphenylphosphine)palladium (0.813 g, 0.7 mmol) was added, and the mixture was stirred for 6 h at 80° C. and concentrated. The residue was taken up in water and extracted with ethyl acetate. The organics were washed, dried and concentrated. The crude product was chromatographed on silica gel using heptane/ethyl acetate as eluent to obtain 4-benzo[b]thiophen-5-yl-3,5-dimethyl-isoxazole (0.69 g) as a light yellow solid. MS (ISP): m/e 230.1 (M+H)⁺ ii) 5-(3,5-Dimethyl-isoxazol-4-yl)-benzo[b]thiophene-2-sulfonyl chloride

To a solution of 4-benzo[b]thiophen-5-yl-3,5-dimethyl-isoxazole (0.37 g, 1.6 mmol) in diethyl ether (30 mL) was added dropwise at −20° C. n-BuLi (1.6N, 1.05 mL, 1.65 mmol). The reaction mixture was stirred at −20° C. for 2 h, then a stream of sulfur dioxide was passed over the surface of the solvent until reaction was no more exothermic. The suspension was stirred at rt for 1 h and concentrated under vacuum. The residue was suspended in dichloromethane (50 mL) and N-chlorosuccinimide (0.235 g, 1.75 mmol) was added. The mixture was stirred at rt for 2 h, quenched with water and extracted with dichloromethane. The dried organic phases were concentrated, and the residue was chromatographed on silica gel using heptane/ethyl acetate as eluent to obtain (3,5-dimethyl-isoxazol-4-yl)-benzo[b]thiophene-2-sulfonyl chloride (0.065 g) as a yellowish solid. MS (EI): m/e 327.1 (M)

iii) N-[(5-bromo-1,3-thiazol-2-yl)carbamoyl]-5-(3,5-dimethylisoxazol-4-yl)-1-benzothiophene-2-sulfonamide The title compound was prepared in analogy to the procedure described in Example 1, starting from 5-(3,5-dimethyl-isoxazol-4-yl)-benzo[b]thiophene-2-sulfonyl chloride to obtain the desired compound as a creamy solid. MS (ISN): m/e 510.9, 512.8 (M−H)⁻

Example 17

N-[(5-Bromo-1,3-thiazol-2-yl)carbamoyl]-5-methoxy-1-benzothiophene-2-sulfonamide The title compound was prepared in analogy to the procedure described in Example 1 starting from 5-methoxy-1-benzothiophene-2-sulfonyl chloride (Shepard, K., Graham, S., EP129478 1984) to obtain the desired compound as a creamy solid. MS (ISN): m/e 446.2, 448.1 (M−H)⁻

Example 18

N-[(5-Bromo-1,3-thiazol-2-yl)carbamoyl]-7-chloro-1-benzothiophene-3-sulfonamide The title compound was prepared in analogy to the procedure described in Example 1, starting from 7-chloro-1-benzothiophene-3-sulfonyl chloride (Chapman, N., Hughes, C., J C S, Sec C Organic, 2431-2435, 1970) to obtain the desired compound as a creamy solid. MS (ISN): m/e 451.7, 453.8 (M−H)−

Example 19

N-[(5-Bromo-1,3-thiazol-2-yl)carbamoyl]-7-chloro-1-benzothiophene-2-sulfonamide The title compound was prepared in analogy to the procedure described in Example 1 starting from 7-chloro-1-benzothiophene-2-sulfonyl chloride (Mochida, E., Murakami, K., EP35827) to obtain the desired compound as a colourless solid. MS (ISN): m/e 452.1, 454.0 (M−H)−

Example 20

N-[(5-Bromo-1,3-thiazol-2-yl)carbamoyl]-1H-indole-2-sulfonamide

To a solution of 1H-indole-2-sulfonic acid amide (Graham, S., Hoffman, J. Med. Chem., 33(2), 749-754 (1990); 0.235 g, 1.2 mmol) in acetonitrile (15 mL) was added at 10° C. triethylamine (0.4 mL), followed dropwise over 5 minutes by a solution of chloroformic acid phenyl ester (0.22 g, 1.4 mmol) in acetonitrile (2 mL). The reaction mixture was stirred at rt for 1 h and 2-amino-5-bromothiazole (0.225 g, 1.3 mmol) was added. The reaction mixture was stirred at 55° C. for 2 h. The precipitate that was formed was filtered off, washed with acetonitrile and ether and dried to obtain the title compound (0.18 g) as a pink solid. MS (ISN) m/e 399.0, 400.9 (M−H)−

Example 21

N-[(5-Bromo-1,3-thiazol-2-yl)carbamoyl]-7-(3,5-dimethylisoxazol-4-yl)-1-benzothiophene-2-sulfonamide i) 4-Benzo[b]thiophen-7-yl-3,5-dimethyl-isoxazole

This compound was prepared in analogy to the procedure described in Example 16i) starting from 7-bromo-benzo[b]thiophene (Focus synthesis, CAS:1423-61-6) to obtain 4-benzo[b]thiophen-7-yl-3,5-dimethyl-isoxazole as a light grey solid. MS (ISP) m/e 230.1 (M+H)+ ii) 7-(3,5-Dimethyl-isoxazol-4-yl)-benzo[b]thiophene-2-sulfonyl chloride

This compound was prepared in analogy to the procedure described in Example 16ii) starting from 4-benzo[b]thiophen-7-yl-3,5-dimethyl-isoxazole to obtain the desired compound as a colourless solid. MS (ISP): m/e 328.1 (M+H)+ iii) N-[(5-bromo-1,3-thiazol-2-yl)carbamoyl]-7-(3,5-dimethylisoxazol-4-yl)-1-benzothiophene-2-sulfonamide The title compound was prepared in analogy to the procedure described in Example 1, starting from 7-(3,5-dimethyl-isoxazol-4-yl)-benzo[b]thiophene-2-sulfonyl chloride to obtain the desired compound as a creamy solid. MS (ISN) m/e 511.3, 513.3 (M−H)−

Example 22

N-[(5-Bromo-1,3-thiazol-2-yl)carbamoyl]-7-pyridin-4-yl-1-benzothiophene-2-sulfonamide i) 4-Benzo[b]thiophen-7-yl-pyridine

This compound was prepared in analogy to the procedure described in Example 16i) starting from 7-bromo-benzo[b]thiophene (Focus synthesis, CAS:1423-61-6) using 4-pyridineboronic acid as reagent to obtain 4-benzo[b]thiophen-7-yl-pyridine as a grey solid. MS (ISP): m/e 212.1 (M+H)+ ii) 7-Pyridin-4-yl-benzo[b]thiophene-2-sulfonic acid amide

To a solution of 4-benzo[b]thiophen-7-yl-pyridine (0.28 g), 1.32 mmol) in THF (5 mL) was added at −75° C. n-butyllithium over 10 minutes. The reaction mixture was stirred at that temperature for 1 h, $SO_2$ was passed over the surface of the mixture until the exothermic reaction ceased. The reaction mixture was stirred for 1 h without heating, the solvent was removed under vacuum. The residue suspended in dichloromethane (30 mL), NCS (0.204 g, 0.15 mmol) was added and stirred at rt for 2 h. Ammonia gas was introduced for 5-10 minutes. The mixture was stirred at rt overnight, quenched with water, and extracted with ethyl acetate. The organics were washed, dried and concentrated. The crude compound was treated with ether. The solid was filtered off, washed and dried to obtain 7-pyridin-4-yl-benzo[b]thiophene-2-sulfonic acid amide (0.125 g) as a light brown solid. MS (ISN) m/e 289.0 (M−H)− iii) N-[(5-Bromo-1,3-thiazol-2-yl)carbamoyl]-7-pyridin-4-yl-1-benzothiophene-2-sulfonamide To a suspension of 7-pyridin-4-yl-benzo[b]thiophene-2-sulfonic acid amide (0.10 g, 0.34 mmol) in acetonitrile (3 mL) were added triethylamine (0.11 mL, 0.8 mmol) and at 0-5° C. phenylchloroformate (0.065 g, 0.40 mmol). The mixture was stirred at rt for 2 h, and 5-bromo-thiazol-2-yl-amine (0.092 g, 0.50 mmol) was added. The reaction mixture was stirred at 55-60° C. for 3 h. After cooling down to rt, the solution was chromatographed over silica gel using dichloromethane/methanol as eluent to obtain the title compound (0.045 g) as a light brown solid. MS (ISN) m/e 492.8, 494.8 (M−H)−

Example 23

N-[(5-Bromo-1,3-thiazol-2-yl)carbamoyl]-1-methyl-1H-indole-3-sulfonamide i) 1-Methyl-1H-indole-3-sulfonyl chloride

This compound was prepared in analogy to the procedure described in Example 6i) starting from 1-methyl-1H-indole (Aldrich, CAS: 603-76-9) to obtain 1-methyl-1H-indole-3-sulfonyl chloride as a yellowish solid. MS (EI): m/e 229.1 (M)

ii) 1-Methyl-1H-indole-3-sulfonic acid amide

To a solution of 1-methyl-1H-indole-3-sulfonyl chloride (0.86 g, 3.75 mmol) in THF (40 mL) was added ammonia gas until saturation at ca. 10° C., then the flask was stoppered, and the reaction mixture was stirred at rt for 4 h. The reaction mixture was then quenched with water; the organic solvent was slowly evaporated under vacuum. The precipitate formed was filtered off, washed with water and dried over $P_2O_5$ under high vacuum to obtain 1-methyl-1H-indole-3-sulfonic acid amide (0.64 g) as a yellowish solid. MS (ISN): m/e 209.4 $(M–H)^-$ iii) N-[(5-Bromo-1,3-thiazol-2-yl)carbamoyl]-1-methyl-1H-indole-3-sulfonamide The title compound was prepared in analogy to the procedure described in Example 22iii) starting from 1-methyl-1H-indole-3-sulfonic acid amide to obtain the desired compound as a brownish solid. MS (ISN): m/e 412.9, 414.9 $(M–H)^-$ Example 24

5-(Benzyloxy)-N-[(5-bromo-1,3-thiazol-2-yl)carbamoyl]-1-methyl-1H-indole-3-sulfonamide i) 5-Benzyloxy-1-methyl-1H-indole-3-sulfonyl chloride This compound was prepared in analogy to the procedure described in Example 6i) starting from 5-benzyloxy-1-methyl-1H-indole (Salor, CAS:2439-68-1) to obtain the desired compound as a yellowish solid. MS (EI): m/e 335.0 (M)

ii) 5-Benzyloxy-1-methyl-1H-indole-3-sulfonic acid amide

This compound was prepared in analogy to the procedure described in Example 23ii) starting from 5-benzyloxy-1-methyl-1H-indole-3-sulfonyl chloride to obtain the desired compound as a pink solid. MS (ISN): m/e 315.4 $(M–H)^-$ iii) 5-(Benzyloxy)-N-[(5-bromo-1,3-thiazol-2-yl)carbamoyl]-1-methyl-1H-indole-3-sulfonamide The title compound was prepared in analogy to the procedure described in Example 22iii) starting from 5-benzyloxy-1-methyl-1H-indole-3-sulfonic acid amide to obtain the desired compound as a creamy solid. MS (ISN): m/e 519.2, 521.2 $(M–H)^-$ Example 25

Methyl 3-({[(5-bromo-1,3-thiazol-2-yl)carbamoyl]amino}sulfonyl)-1-methyl-1H-indole-5-carboxylate i) 3-Chlorosulfonyl-1-methyl-1H-indole-5-carboxylic acid methyl ester This compound was prepared in analogy to the procedure described in Example 6i) starting from 1-methyl-1H-indole-5-carboxylic acid methyl ester (Robert John; Failli, Amedeo Arturo, WO 2000046228) to obtain the desired compound as a yellow solid. MS (ISP): m/e 287.8 $(M+H)^+$ ii) 1-Methyl-3-sulfamoyl-1H-indole-5-carboxylic acid methyl ester This compound was prepared in analogy to the procedure described in Example 23ii) starting from 3-chlorosulfonyl-1-methyl-1H-indole-5-carboxylic acid methyl ester to obtain the desired compound as a creamy solid. MS (ISN): m/e 267.1 $(M–H)^-$ iii) Methyl 3-({[(5-bromo-1,3-thiazol-2-yl)carbamoyl]amino}sulfonyl)-1-methyl-1H-indole-5-carboxylate The title compound was prepared in analogy to the procedure described in Example 22iii) using 1-methyl-3-sulfamoyl-1H-indole-5-carboxylic acid methyl ester to obtain the desired compound as a colourless solid. MS (ISN): m/e 470.8, 472.8 $(M–H)^-$ Example 26

N-[(5-Bromo-1,3-thiazol-2-yl)carbamoyl]-5-fluoro-1-methyl-1H-indole-3-sulfonamide i) 5-Fluoro-1-methyl-1H-indole-3-sulfonyl chloride This compound was prepared in analogy to Example 6i) starting from 5-fluoro-1-methyl-1H-indole (Chemstep products, CAS: 116176-92-2) to obtain the desired compound as a colourless solid. MS (EI): m/e 247.1 (M)

ii) 5-Fluoro-1-methyl-1H-indole-3-sulfonic acid amide

This compound was prepared in analogy to the procedure described in Example 23ii) starting from 5-fluoro-1-methyl-1H-indole-3-sulfonyl chloride to obtain the desired compound as a white solid. MS (ISN): m/e 227.4 $(M–H)^-$ iii) N-[(5-Bromo-1,3-thiazol-2-yl)carbamoyl]-5-fluoro-1-methyl-1H-indole-3-sulfonamide The title compound was prepared in analogy to the procedure described in Example 22iii) using 5-fluoro-1-methyl-1H-indole-3-sulfonic acid amide to obtain the desired compound as a creamy solid. MS (ISN): m/e 430.9, 432.8 $(M–H)^-$ Example 27

Methyl 3-({[(5-bromo-1,3-thiazol-2-yl)carbamoyl]amino}sulfonyl)-1-methyl-1H-indole-6-carboxylate i) 3-Chlorosulfonyl-1-methyl-1H-indole-6-carboxylic acid methyl ester This compound was prepared in analogy to the procedure described in Example 6i) starting from 1-methyl-1H-indole-6-carboxylic acid methyl ester (Fluorochem, CAS: 1204-32-6) to obtain the desired compound as off-white crystals. MS (ISP): m/e 287.9 $(M+H)^+$ ii) 1-Methyl-3-sulfamoyl-1H-indole-6-carboxylic acid methyl ester This compound was prepared in analogy to the procedure described in Example 23ii) starting from 3-chlorosulfonyl-1-methyl-1H-indole-6-carboxylic acid methyl ester to obtain the desired compound as an off-white solid. MS: m/e 267.1 $(M–H)^-$ iii) Methyl 3-({[(5-bromo-1,3-thiazol-2-yl)carbamoyl]amino}sulfonyl)-1-methyl-1H-indole-6-carboxylate The title compound was prepared in analogy to the procedure described in Example 22iii) using 1-methyl-3-sulfamoyl-1H-indole-5-carboxylic acid methyl ester to obtain the desired compound as a creamy solid. MS (ISN): m/e 471.3, 473.2 (M−H)⁻

Example 28

6-(Benzyloxy)-N-[(5-bromo-1,3-thiazol-2-yl)carbamoyl]-1-methyl-1H-indole-3-sulfonamide i) 6-Benzyloxy-1-methyl-1H-indole-3-sulfonyl chloride

This compound was prepared in analogy to the procedure described in Example 6i) starting from 6-benzyloxy-1-methyl-1H-indole (Junino, Alex; Lang, Gerard; Vandenbossche, Jean Jacques, DE 3930473) to obtain the desired compound as light brown solid. MS (EI): m/e 335.1 (M)

ii) 6-Benzyloxy-1-methyl-1H-indole-3-sulfonic acid amide

This compound was prepared in analogy to the procedure described in Example 23ii) starting from 6-benzyloxy-1-methyl-1H-indole-3-sulfonyl chloride to obtain the desired compound as a creamy solid. MS (ISN): m/e 315.3 (M−H)⁻ iii) 6-(Benzyloxy)-N-[(5-bromo-1,3-thiazol-2-yl)carbamoyl]-1-methyl-1H-indole-3-sulfonamide The title compound was prepared in analogy to the procedure described in Example 22iii) using 6-benzyloxy-1-methyl-1H-indole-3-sulfonic acid amide to obtain the desired compound as a creamy solid. MS (ISN): m/e 519.2, 521.2 (M−H)⁻

Example 29

N-[(5-Bromo-1,3-thiazol-2-yl)carbamoyl]-6-cyano-1-methyl-1H-indole-3-sulfonamide i) 6-Cyano-1-methyl-1H-indole-3-sulfonyl chloride

This compound was prepared in analogy to the procedure described in Example 6i) starting from 1-methyl-1H-indole-6-carbonitrile (Maybridge, CAS: 20996-87-6) to obtain the desired compound as light yellow crystals. MS (ISP): m/e 272.3 (M+NH4)⁺ ii) 6-Cyano-1-methyl-1H-indole-3-sulfonic acid amide

This compound was prepared in analogy to the procedure described in Example 23ii) starting from 6-cyano-1-methyl-1H-indole-3-sulfonyl chloride to obtain the desired compound as a colourless solid. MS (ISN): m/e 234.3 (M−H)⁻ iii) N-[(5-Bromo-1,3-thiazol-2-yl)carbamoyl]-6-cyano-1-methyl-1H-indole-3-sulfonamide The title compound was prepared in analogy to the procedure described in Example 22iii) using 6-cyano-1-methyl-1H-indole-3-sulfonic acid amide to obtain the desired compound as a creamy solid. MS (ISN): m/e 438.1, 440.3 (M−H)⁻

Example 30

N-[(5-Bromo-1,3-thiazol-2-yl)carbamoyl]-1-methyl-6-(methylsulfonyl)-1H-indole-3-sulfonamide i) 6-Methanesulfonyl-1-methyl-1H-indole

To a slurry of sodium hydride (60% in mineral oil, 0.90 g, 23 mmol) was added in portions 6-(methylsulfonyl)-1H-indole (4.0 g, 20 mmol) over 5 minutes at 5-10° C. The reaction mixture was stirred at rt for 1 h until hydrogen evolution ceased, and methyl iodide was added dropwise over 5 minutes at 10-20° C. The mixture was stirred at rt for 1 h, quenched with ice/water, and extracted with tert-butylmethyl ether. The organics were washed, dried and concentrated. The residue was crystallized from ether/hexane to yield the desired compound (3.8 g) as a yellowish solid. MS (ISP): m/e 210.1 (M+H)⁺ i) 6-Methanesulfonyl-1-methyl-1H-indole-3-sulfonyl chloride

This compound was prepared in analogy to the procedure in Example 6i) starting from 6-methanesulfonyl-1-methyl-1H-indole to obtain the desired compound as a yellowish solid. M (EI): m/e 307.1 (M)

iii) 6-Methanesulfonyl-1-methyl-1H-indole-3-sulfonic acid amide

This compound was prepared in analogy to the procedure in Example 23ii) starting from 6-methanesulfonyl-1-methyl-1H-indole-3-sulfonyl chloride to obtain the desired compound as a creamy solid. MS (ISN): m/e 287.3 (M−H)⁻ iv) N-[(5-Bromo-1,3-thiazol-2-yl)carbamoyl]-1-methyl-6-(methylsulfonyl)-1H-indole-3-sulfonamide The title compound was prepared in analogy to the procedure described in Example 22iii) using 6-methanesulfonyl-1-methyl-1H-indole-3-sulfonic acid amide to obtain the desired compound as a creamy solid. MS (ISN): m/e 491.2, 493.2 (M−H)⁻

Example 31

N-[(5-Bromo-1,3-thiazol-2-yl)carbamoyl]-1-(2-methoxyethyl)-1H-indole-3-sulfonamide i) 1-(2-Methoxy-ethyl)-1H-indole

To a slurry of sodium hydride (0.932 g, 23.0 mmol) in DMF (30 mL) was added indole (2.52 g, 21 mmol) portionwise at 10-20° C. over 5 minutes. The reaction mixture was stirred at rt for 1.5 h, and 2-iodoethylmethylether (4.8 g, 26 mmol) in DMF (10 mL) was added over 5 minutes. The mixture was stirred at rt for 2 h, quenched with ice/water, and extracted with tert-butylmethylether. The organics were washed, dried, and concentrated. The residue was chromatographed on silica gel using heptane/ethyl acetate as eluent to obtain 1-(2-methoxy-ethyl)-1H-indole (3.40 g) as a yellowish liquid. MS (ISP): m/e 176.4 (M+H)⁺ ii) 1-(2-Methoxy-ethyl)-1H-indole-3-sulfonyl chloride

This compound was prepared in analogy to the procedure described in Example 6ii) starting from 1-(2-methoxy-ethyl)-1H-indole to obtain the desired compound as a yellowish solid. MS (EI): m/e 273.1 (M)

iii) 1-(2-Methoxy-ethyl)-1H-indole-3-sulfonic acid amide

This compound was prepared in analogy to the procedure described in Example 23ii) starting from 1-(2-methoxy-ethyl)-1H-indole-3-sulfonyl chloride to obtain the desired compound as a colourless solid. MS (ISN): m/e 253.1 (M−H)$^-$ iv) N-[(5-bromo-1,3-thiazol-2-yl)carbamoyl]-1-(2-methoxyethyl)-1H-indole-3-sulfonamide The title compound was prepared in analogy to the procedure described in Example 22iii) starting from 1-(2-methoxy-ethyl)-1H-indole-3-sulfonic acid amide to obtain the desired compound as brownish solid. MS: m/e 457.2, 459.4 (M−H)$^-$ Example 32

Methyl 3-({[(5-bromo-1,3-thiazol-2-yl)carbamoyl]amino}sulfonyl)-1-methyl-1H-indole-7-carboxylate i) 3-Chlorosulfonyl-1-methyl-1H-indole-7-carboxylic acid methyl ester This compound was prepared in analogy to the procedure described in Example 6i) starting from 1-methyl-1H-indole-7-carboxylic acid methyl ester (Burgess, Walter J.; Jakas, Dalia; Huffman, William F.; Miller, William H.; Newlander, Kenneth A.; Seefeld, Mark A.; Uzinskas, Irene N., WO2003088897) to obtain the desired compound as yellowish solid. MS (ISP): m/e 305.1 (M+NH$_4$)$^+$ ii) 1-Methyl-3-sulfamoyl-1H-indole-7-carboxylic acid methyl ester This compound was prepared in analogy to the procedure described in Example 23ii) starting from 3-chlorosulfonyl-1-methyl-1H-indole-7-carboxylic acid methyl ester to obtain the desired compound as a colourless solid. MS: m/e 267.1 (M−H)$^-$ iii) Methyl 3-({[(5-bromo-1,3-thiazol-2-yl)carbamoyl]amino}sulfonyl)-1-methyl-1H-indole-7-carboxylate The title compound was prepared in analogy to the procedure described in Example 22iii) starting from 1-methyl-3-sulfamoyl-1H-indole-7-carboxylic acid methyl ester to obtain the desired compound as a brownish solid. MS (ISN): m/e 471.1, 473.2 (M−H)$^-$ Example 33

N-[(5-Bromo-1,3-thiazol-2-yl)carbamoyl]-7-methoxy-1-methyl-1H-indole-3-sulfonamide i) 7-Methoxy-1-methyl-1H-indole-3-sulfonyl chloride This compound was prepared in analogy to the procedure described in Example 6i) starting from 7-methoxy-1-methyl-1H-indole, (Burgess, Walter J.; Jakas, Dalia; Huffman, William F.; Miller, William H.; Newlander, Kenneth A.; Seefeld, Mark A.; Uzinskas, Irene N., WO2003088897) to obtain the desired compound as a yellow solid. MS (EI): m/e 259.1 (M)

ii) 7-Methoxy-1-methyl-1H-indole-3-sulfonic acid amide

This compound was prepared in analogy to the procedure described in Example 23ii) starting from 7-methoxy-1-methyl-1H-indole-3-sulfonyl chloride to obtain the desired compound as a creamy solid. MS (ISN): m/e 239.3 (M−H)$^-$ iii) N-[(5-Bromo-1,3-thiazol-2-yl)carbamoyl]-7-methoxy-1-methyl-1H-indole-3-sulfonamide The title compound was prepared in analogy to the procedure described in Example 22iii) starting from 7-methoxy-1-methyl-1H-indole-3-sulfonic acid amide to obtain the desired compound as a brownish solid. MS: m/e 443.2, 445.3 (M−H)$^-$ Example 34

7-Bromo-N-[(5-bromo-1,3-thiazol-2-yl)carbamoyl]-1-methyl-1H-indole-3-sulfonamide i) 7-Bromo-1-methyl-1H-indole-3-sulfonyl chloride This compound is prepared in analogy to the procedure described in Example 6i) starting from 7-bromo-1-methyl-1H-indole (Stadlwieser, Josef F.; Dambaur, Markus E., Helv. Chim. Acta 2006, 89(5), 936-946) to obtain the desired compound as a yellowish solid. MS (EI): m/e 308.1 (M)

ii) 7-Bromo-1-methyl-1H-indole-3-sulfonic acid amide

This compound is prepared in analogy to the procedure described in Example 23ii) starting from 7-bromo-1-methyl-1H-indole-3-sulfonyl chloride to obtain the desired compound as a yellow solid. MS (ISN): m/e 287.1, 289.1 (M−H)$^-$ iii) 7-Bromo-N-[(5-bromo-1,3-thiazol-2-yl)carbamoyl]-1-methyl-1H-indole-3-sulfonamide The title compound was prepared in analogy to the procedure described in Example 22iii) starting from 7-bromo-1-methyl-1H-indole-3-sulfonic acid amide to obtain the desired compound as a brownish solid MS: m/e 443.2, 445.3 (M−H)$^-$ Example 35

N-[(5-Bromo-4-methyl-1,3-thiazol-2-yl)carbamoyl]-5-(methoxymethyl)-4-methylfuran-2-sulfonamide i) (3-Methyl-furan-2-yl)-methanol Under an inert atmosphere lithium aluminum hydride (6.77 g, 178.4 mmol, 2.5 equiv.) was suspended in dry tetrahydrofuran. The mixture was cooled with an ice-bath, then a solution of 3-methyl-furan-2-carboxylic acid methyl ester (10 g, 71.4 mmol, 1.0 equiv.) in dry tetrahydrofuran was added dropwise. The reaction was stirred overnight at room temp., then quenched with diluted acid, filtered and the filtrate was extracted with diethyl ether. The combined organic extracts were washed with brine, dried over magnesium sulfate dihydrate, filtered and evaporated to obtain 7.2 g of the title compound as colorless oil. GC-MS (EI): M=112.

ii) 2-Methoxymethyl-3-methyl-furan

Under an inert atmosphere sodium hydride (0.25 g ~60%, 6.2 mmol, 1.1 equiv.) was suspended in dry tetrahydrofuran. At 5° C. a solution of (3-methyl-furan-2-yl)-methanol (0.63 g, 5.6 mmol) in dry tetrahydrofuran was added dropwise. The mixture was stirred at room temp. for one hour, then iodomethane (0.9 g, 6.2 mmol, 1.1 equiv.) was added dropwise. The mixture was stirred overnight at room temp., quenched with diluted acid and extracted with diethyl ether. The combined, organic extracts were washed with brine, dried over magnesium sulfate dihydrate, filtered and concentrated under reduced pressure to give 0.8 g of the title compound as a light yellow oil. GC-MS (EI): M=126.

iii) 5-Methoxymethyl-4-methyl-furan-2-sulfonic acid amide

The title compound, MS: m/e 204.0 (M–H) was prepared analogously to the procedure described for Example 22ii), using 2-methoxymethyl-3-methyl-furan.

iv) N-[(5-Bromo-4-methyl-1,3-thiazol-2-yl)carbamoyl]-5-(methoxymethyl)-4-methylfuran-2-sulfonamide The title compound, MS: m/e 421.9 (M–H) was prepared analogously to the procedure described for Example 22iii), using 5-methoxymethyl-4-methyl-furan-2-sulfonic acid amide and 5-bromo-4-methyl-thiazol-2-ylamine.

Example 36

N-[(5-Bromo-1,3-thiazol-2-yl)carbamoyl]-5-(methoxymethyl)-4-methylfuran-2-sulfonamide The title compound, MS: m/e 409.9 (M–H) was prepared analogously to the procedure described for Example 22iii), using 5-methoxymethyl-4-methyl-furan-2-sulfonic acid amide.

Example 37

7-(Benzyloxy)-N-[(5-bromo-1,3-thiazol-2-yl)carbamoyl]-1-benzothiophene-2-sulfonamide i) 7-Benzyloxy-benzo[b]thiophene-2-sulfonyl chloride

This compound was prepared in analogy to the procedure described in example 16ii), starting from 7-benzyloxy-benzo[b]thiophene (Binggeli, Alfred; Boehringer, Markus; Grether, Uwe; Hilpert, Hans; Maerki, Hans-Peter; Meyer, Markus; Mohr, Peter; Ricklin, Fabienne, WO 2002092084) to obtain the desired compound as a slightly yellow solid. MS (EI): m/e 338.1 (M)

ii) 7-Benzyloxy-benzo[b]thiophene-2-sulfonic acid amide

This compound was prepared in analogy to the procedure described in example 23ii) starting from 7-benzyloxy-benzo[b]thiophene-2-sulfonyl chloride to obtain the desired compound as a slightly yellow solid. MS (ISN): m/e 318.3 (M–H)⁻ iii) 7-(Benzyloxy)-N-[(5-bromo-1,3-thiazol-2-yl)carbamoyl]-1-benzothiophene-2-sulfonamide The title compound was prepared in analogy to the procedure described in example 22iii) starting from 7-benzyloxy-benzo[b]thiophene-2-sulfonic acid amide to obtain the desired compound as a colourless solid. MS: m/e 523.8, 521.9 (M–H)⁻

Example 38

N-[(5-bromo-1,3-thiazol-2-yl)carbamoyl]-7-(2-methoxyethoxy)-1-benzothiophene-2-sulfonamide i) 7-(2-Methoxy-ethoxy)-benzo[b]thiophene

To a solution of 7-hydroxy-benzo[b]thiophene (Boot, J. R.; Brace, G.; Delatour, C. L.; Dezutter, N.; Fairhurst, J.; Findlay, J.; Gallagher, P. T.; Hoes, I.; Mahadevan, S.; Mitchell, S. N.; Rathmell, R. E.; Richards, S. J.; Simmonds, R. G.; Wallace, L.; Whatton, M. A.; Bioorganic & Medicinal Chemistry Letters (2004), 14(21), 5395-5399; 1.0 g, 6.6 mmol) in acetone (15 mL) was added 2-iodoethyl methylether (Ubichem, CAS: 4296-15-5, 2.47 g, 13.2 mmol) and potassium carbonate (1.84 g, 13.2 g). The reaction mixture was stirred at reflux for 16 h, quenched with ice/water, and extracted with ethyl acetate. The organics were washed, dried and concentrated. The residue was chromatographed on silica gel using heptane/ethyl acetate as eluent to obtain 7-(2-methoxy-ethoxy)-benzo[b]thiophene (1.29 g) as a colourless oil. MS (ISP): m/209.1 (M+H)⁺ ii) 7-(2-Methoxy-ethoxy)-benzo[b]thiophene-2-sulfonyl chloride

This compound was prepared in analogy to the procedure described in Example 16ii) starting from 7-(2-methoxy-ethoxy)-benzo[b]thiophene to obtain the desired compound as a yellow crystalline solid.

iii) 7-(2-Methoxy-ethoxy)-benzo[b]thiophene-2-sulfonic acid amide

This compound was prepared in analogy to the procedure described in Example 23ii) starting from 7-(2-methoxy-ethoxy)-benzo[b]thiophene-2-sulfonyl chloride to obtain the desired compound as a yellowish crystalline solid. MS (ISN): m/e 286.1 (M–H)⁻ iv) N-[(5-bromo-1,3-thiazol-2-yl)carbamoyl]-7-(2-methoxyethoxy)-1-benzothiophene-2-sulfonamide The title compound was prepared in analogy to the procedure described in Example 22iii) starting from 7-(2-methoxy-ethoxy)-benzo[b]thiophene-2-sulfonic acid amide to obtain the desired compound as a colourless solid. MS: m/e 489.7, 491.9 (M–H)⁻

Example 39

N-[(5-bromo-1,3-thiazol-2-yl)carbamoyl]-7-methoxy-1-benzothiophene-2-sulfonamide i) 7-Methoxy-benzo[b]thiophene-2-sulfonyl chloride

This compound was prepared in analogy to the procedure described in Example 16ii) starting from 7-methoxy-benzo[b]thiophene (FOCUS, CAS: 88791-08-6) to obtain the desired compound as a yellowish crystalline solid. MS (EI): m/e 262.2 (M)

ii) 7-Methoxy-benzo[b]thiophene-2-sulfonic acid amide

This compound was prepared in analogy to the procedure described in Example 23ii) starting from 7-methoxy-benzo[b]thiophene-2-sulfonyl chloride to obtain the desired compound as yellowish crystalline solid. MS: m/e 445.6, 447.6 (M–H)− iii) N-[(5-bromo-1,3-thiazol-2-yl)carbamoyl]-7-methoxy-1-benzothiophene-2-sulfonamide The title compound was prepared in analogy to the procedure described in Example 22iii) starting from 7-methoxy-benzo[b]thiophene-2-sulfonic acid amide to obtain the desired compound as a creamy solid. MS: m/e 445.6, 447.6 (M–H)−

Example 40

N-[(5-bromo-1,3-thiazol-2-yl)carbamoyl]-7-methoxy-1-methyl-1H-indole-2-sulfonamide i) 7-Methoxy-1-methyl-1H-indole-2-sulfonyl chloride

This compound was prepared in analogy to the procedure described in Example 16ii) starting from 7-methoxy-1-methyl-1H-indole (Burgess, Walter J.; Jakas, Dalia; Huffman, William F.; Miller, William H.; Newlander, Kenneth A.; Seefeld, Mark A.; Uzinskas, Irene N. WO 2003088897) to obtain the desired compound as a yellow crystalline solid. MS (EI): m/e 259.2 (M)

ii) 7-Methoxy-1-methyl-1H-indole-2-sulfonic acid amide

This compound was prepared in analogy to the procedure described in Example 23ii) starting from 7-methoxy-1-methyl-1H-indole-2-sulfonyl chloride to obtain the desired compound as a yellowish solid. MS (ISN): m/e 239.1 (M–H)− iii) N-[(5-bromo-1,3-thiazol-2-yl)carbamoyl]-7-methoxy-1-methyl-1H-indole-2-sulfonamide The title compound was prepared in analogy to the procedure described in Example 22iii) starting from 7-methoxy-1-methyl-1H-indole-2-sulfonic acid amide to obtain the desired compound as a creamy solid. MS: m/e 442.9, 444.8 (M–H)−

Example 41

7-(Benzyloxy)-N-[(5-bromo-1,3-thiazol-2-yl)carbamoyl]-1-methyl-1H-indole-3-sulfonamide i) 7-Benzyloxy-1-methyl-1H-indole-3-sulfonyl chloride

This compound was prepared in analogy to the procedure described in Example 6i) starting from 7-benzyloxy-1-methyl-1-H-indole (Kozikowski, Alan P.; Gaisina, Irina N.; Yuan, Hongbin; Petukhov, Pavel A.; Blond, Sylvie Y.; Fedolak, Allison; Caldarone, Barbara; McGonigle, Paul., Journal of the American Chemical Society 2007, 129(26), 8328-8332) to obtain the desired compound as yellow semisolid. MS (EI): m/e 335.1 (M)

ii) 7-Benzyloxy-1-methyl-1H-indole-3-sulfonic acid amide

This compound was prepared in analogy to the procedure described in Example 23ii) starting from 7-benzyloxy-1-methyl-1H-indole-3-sulfonyl chloride to obtain the desired compound as yellowish solid. MS: m/e 315.3 (M–H)− iii) 7-(Benzyloxy)-N-[(5-bromo-1,3-thiazol-2-yl)carbamoyl]-1-methyl-1H-indole-3-sulfonamide The title compound was prepared in analogy to the procedure described in Example 22iii) using 7-benzyloxy-1-methyl-1H-indole-3-sulfonic acid amide to obtain the desired compound as a brownish solid. MS: m/e 519.2, 521.2 (M–H)−

Example 42

N-[(5-bromo-1,3-thiazol-2-yl)carbamoyl]-7-(2-methoxyethoxy)-1-methyl-1H-indole-3-sulfonamide i) 7-(2-Methoxy-ethoxy)-1-methyl-1H-indole

This compound was prepared in analogy to the procedure described in Example 30i) starting from 7-(2-methoxy-ethoxy)-1H-indole (Cuny, Gregory D.; Yuan, Junying; Jagtap, Prakash; Degterev, Alexei; US 2005119260) to obtain the desired compound as a yellowish liquid. MS (ISP): m/e 206.3 (M+H)+ ii) 7-(2-Methoxy-ethoxy)-1-methyl-1H-indole-3-sulfonyl chloride

This compound was prepared in analogy to the procedure described in Example 6i) starting from 7-(2-methoxy-ethoxy)-1-methyl-1H-indole to obtain the desired compound as a yellowish solid. MS (EI): m/e 303.1 (M)

iii) 7-(2-Methoxy-ethoxy)-1-methyl-1H-indole-3-sulfonic acid amide

This compound was prepared in analogy to the procedure described in Example 23ii) starting from 7-(2-methoxy-ethoxy)-1-methyl-1H-indole-3-sulfonyl chloride to obtain the desired compound as an off-white solid. MS: (ISN) m/e 283.4 (M–H)− iv) N-[(5-bromo-1,3-thiazol-2-yl)carbamoyl]-7-(2-methoxyethoxy)-1-methyl-1H-indole-3-sulfonamide The title compound was prepared in analogy to the procedure described in Example 22iii) starting from 7-(2-methoxyethoxy)-1-methyl-1H-indole-3-sulfonic acid amide to obtain the desired compound as a brownish solid. MS (ISN): m/e 487.4, 489.2 (M−H)⁻

Example 43

N-[(5-bromo-1,3-thiazol-2-yl)carbamoyl]-7-methoxy-1H-indole-3-sulfonamide i) 1-Benzenesulfonyl-7-methoxy-1H-indole-3-sulfonyl chloride This compound was prepared in analogy to the procedure described in Example 6i) starting from 1-benzenesulfonyl-7-methoxy-1H-indole (Mahboobi, Siavosh; Uecker, Andrea; Selimer, Andreas; Cenac, Christophe; Hoecher, Heymo; Pongratz, Herwig; Eichhorn, Emerich; Hufsky, Harald; Truempler, Antje; Sicker, Marit; Heidel, Florian; Fischer, Thomas; Stocking, Carol; Elz, Sigurd; Boehmer, Frank-D.; Dove, Stefan.; Journal of Medicinal Chemistry 2006, 49(11), 3101-3115) to obtain the desired compound as a colourless solid. MS (EI): m/e 385.0 (M)

ii) 1-Benzenesulfonyl-7-methoxy-1H-indole-3-sulfonic acid amide

This compound was prepared in analogy to the procedure described in Example 23ii) starting from 1-benzenesulfonyl-7-methoxy-1H-indole-3-sulfonyl chloride to obtain the desired compound as an off-white solid. MS: (ISN) m/e 365.4 (M−H)⁻ iii) 1-(Benzenesulfonyl)-N-[(5-bromo-1,3-thiazol-2-yl)carbamoyl]-7-methoxy-1H-indole-3-sulfonamide This compound was prepared in analogy to the procedure described in Example 22iii) starting from 1-benzenesulfonyl-7-methoxy-1H-indole-3-sulfonic acid amide to obtain the desired compound as a light brown solid. MS (ISN): m/e 569.2, 571.3 (M−H)⁻ iv) N-[(5-bromo-1,3-thiazol-2-yl)carbamoyl]-7-methoxy-1H-indole-3-sulfonamide

A suspension of 1-(benzenesulfonyl)-N-[(5-bromo-1,3-thiazol-2-yl)carbamoyl]-7-methoxy-1H-indole-3-sulfonamide (cf. Ex. 43iii), 0.072 g) in 1 n sodium hydroxide (5 mL) was heated to 70° C. for 4 h. The reaction mixture was cooled down and acidified with 1N HCl to pH 4-5. The precipitate was filtered off, washed with water and dried to obtain the title compound as light brown solid. MS (ISN): m/e 429.3, 431.3 (M−H)⁻

Example 44

7-Methoxy-N-[(5-methoxy-1,3-thiazol-2-yl)carbamoyl]-1-methyl-1H-indole-3-sulfonamide The title compound was prepared in analogy to the procedure described in Example 22iii) starting from 7-methoxy-1-methyl-1H-indole-3-sulfonic acid amide (cf. example 33ii)) and 2-amino-5-methoxythiazole (Forlani, Luciano; Medici, Alessandro; Todesco, Paolo E., Tetrahedron Letters 1976, 3, 201-2. to obtain the desired compound. MS (ISN): m/e 395.3 (M−H)⁻

Example 45

N-[(5-Methoxy-1,3-benzothiazol-2-yl)carbamoyl]-5-(2-methoxyethyl)-4-methylthiophene-2-sulfonamide i) 2-(2-Methoxy-ethyl)-3-methyl-thiophene Some drops from a solution of 2-bromo-3-methylthiophene (1.5 g, 8.5 mmol) in dry diethyl ether was added to a suspension of magnesium (308 mg, 12.7 mmol, 1.5 equiv.) in dry diethyl ether until the Grignard reagent began to form and the mixture started to reflux. The remaining solution was added dropwise. A solution of toluene-4-sulfonic acid 2-methoxy-ethyl ester (2.9 g, 12.7 mmol, 1.5 equiv.) in dry diethyl ether was added dropwise at room temperature, and the mixture was refluxed for two hours. After cooling to room temperature, the mixture was quenched with saturated ammonium chloride solution and extracted with tert. butylmethyl ether. The combined organic extracts were washed with water, brine, dried over magnesiumsulfate-dihydrate, filtered and evaporated to give a yellow oil. After purification on silica gel, 490 mg of the title compound were obtained as a light yellow oil. GC-MS (EI): M=156 ii) 5-(2-Methoxy-ethyl)-4-methyl-thiophene-2-sulfonic acid amide

The title compound, MS: m/e 233.8 (M−H) was prepared analogously to the procedure described for 22ii), using 2-(2-methoxy-ethyl)-3-methyl-thiophene.

iii) N-[(5-Methoxy-1,3-benzothiazol-2-yl)carbamoyl]-5-(2-methoxyethyl)-4-methylthiophene-2-sulfonamide The title compound, MS: m/e 440.2 (M−H), was prepared analogously to the procedure described for 22iii), using 5-(2-methoxy-ethyl)-4-methyl-thiophene-2-sulfonic acid amide and 5-methoxy-benzo[b]thiophen-2-ylamine.

Example 46

2-{[3-({[(5-Methoxy-1,3-thiazol-2-yl)carbamoyl] amino}sulfonyl)-1-methyl-1H-indol-7-yl]oxy}ethyl acetate i) 2-(1-Methyl-1H-indol-7-yloxy)-ethanol To a solution of 1-methyl-1-H-indol-7-ol (Chemstep, CAS: 47577-33-4, 0.98 g, 6.8 mmol) and 2-iodoethanol (Fluka, 1.60 g, 8.6 mmol)) in DMF abs. (10 mL) was added potassium carbonate (1.84 g, 13 mmol). The reaction mixture at rt for 20 h, then at 70° C. for 24 h, quenched with ice/water, extracted with ethyl acetate. The organics were washed, dried and concentrated, the residue chromatographed on silica gel using heptane/ethyl acetate as eluent to obtain the desired compound (0.82 g) as a creamy solid. MS (ISP): m/e 192.3 (M+H)⁺ ii) Acetic acid 2-(1-methyl-1H-indol-7-yloxy)-ethyl ester

A solution of 2-(1-methyl-1H-indol-7-yloxy)-ethanol (0.78 g, 4 mmol) in pyridine (10 mL) was treated with acetic anhydride (5 mL). The reaction mixture was stirred at rt for 4 h and concentrated. The residue was quenched with ice/water and extracted with ethyl acetate. The organics were washed with 2N sulfuric acid, sat. sodium bicarbonate and brine, dried and concentrated. The residue was chromatographed on silica gel using heptane/ethyl acetate as eluent to produce the desired compound (0.90 g) as an off-white solid. MS (ISP): m/e 234.1 (M+H)+ iii) Acetic acid 2-(3-chlorosulfonyl-1-methyl-1H-indol-7-yloxy)-ethyl ester

This compound was prepared in analogy to the procedure described in Example 6i) starting from acetic acid 2-(1-methyl-1H-indol-7-yloxy)-ethyl ester to obtain the desired compound as brownish viscous oil. MS (ISP): m/e 332.0 (M+H)+ iv) Acetic acid 2-(1-methyl-3-sulfamoyl-1H-indol-7-yloxy)-ethyl ester

This compound was prepared in analogy to the procedure described in Example 23ii) starting from acetic acid 2-(3-chlorosulfonyl-1-methyl-1H-indol-7-yloxy)-ethyl ester to obtain the desired compound as a yellowish solid. MS (ISN): m/e 311.5 (M−H)− v) 2-{[3-({[(5-methoxy-1,3-thiazol-2-yl)carbamoyl]amino}sulfonyl)-1-methyl-1H-indol-7-yl]oxy}ethyl acetate The title compound was prepared in analogy to the procedure described in Example 22iii) starting from acetic acid 2-(1-methyl-3-sulfamoyl-1H-indol-7-yloxy)-ethyl ester to obtain the desired compound as a light brown solid. MS (ISN): m/e 467.4 (M−H)−

Example 47

7-(2-Hydroxyethoxy)-N-[(5-methoxy-1,3-thiazol-2-yl)carbamoyl]-1-methyl-1H-indole-3-sulfonamide A solution of 2-{[3-({[(5-methoxy-1,3-thiazol-2-yl)carbamoyl]amino}sulfonyl)-1-methyl-1H-indol-7-yl]oxy}ethyl acetate (0.065 g) in THF (10 mL) was treated with 2N sodium carbonate (2 mL) and 2N sodium hydroxide (2 mL). The reaction mixture was stirred at rt for 60 h and acidified to about pH 4. The organic solvent were slowly evaporated, leaving back a solid, which was filtered, washed and dried to obtain the title compound (0.055 g) as a brownish solid. MS (ISN): m/e 425.3 (M−H)−

Example 48

2-{[3-({[(5-Bromo-1,3-thiazol-2-yl)carbamoyl]amino}sulfonyl)-1-methyl-1H-indol-7-yl]oxy}ethyl acetate The title compound was prepared in analogy to the procedure described in Example 22iii) starting from acetic acid 2-(1-methyl-3-sulfamoyl-1H-indol-7-yloxy)-ethyl ester (cf. example 46d) and 5-bromo-thiazole-2-ylamine (Astatech, CAS: 3024-22-8) to obtain the desired compound as brownish solid. MS (ISN): m/e 514.9, 516.9 (M−H)−

Example 49

N-[(5-Bromo-1,3-thiazol-2-yl)carbamoyl]-7-(2-hydroxyethoxy)-1-methyl-1H-indole-3-sulfonamide The title compound was prepared in analogy to the procedure described in Example 47 starting from 2-{[3-({[(5-bromo-1,3-thiazol-2-yl)carbamoyl]amino}sulfonyl)-1-methyl-1H-indol-7-yl]oxy}ethyl acetate to obtain the desired compound as a brownish solid. MS (ISN): m/e 473.2, 475.2 (M−H)−

Example 50

Ethyl {[3-({[(5-bromo-1,3-thiazol-2-yl)carbamoyl]amino}sulfonyl)-1-methyl-1H-indol-7-yl]oxy}acetate i) (1-Methyl-1H-indol-7-yloxy)-acetic acid ethyl ester

To a solution of 1-methyl-1-H-indol-7-ol (Chemstep, CAS: 47577-334, 2.5 g, 17 mmol) and ethyl iodoacetate (Fluka, CAS: 623-48-3, 4.58 g, 21 mmol) in DMF abs. (25 mL) was added potassium carbonate (4.23 g, 31 mmol). The reaction mixture was stirred at rt for 20 h, quenched with ice/water, and extracted with ethyl acetate. The organics were washed, dried and concentrated, the residue was chromatographed on silica gel using heptane/ethyl acetate as eluent to obtain the desired compound (3.37 g) as a creamy solid. MS (ISP): m/e 234.1 (M+H)+ ii) (3-Chlorosulfonyl-1-methyl-1H-indol-7-yloxy)-acetic acid ethyl ester

This compound was prepared in analogy to the procedure described in Example 6i) starting from 1-methyl-1H-indol-7-yloxy)-acetic acid ethyl ester to obtain the desired compound as a yellowish solid. MS (ISP): m/e 332.2 (M+H)+ iii) (1-Methyl-3-sulfamoyl-1H-indol-7-yloxy)-acetic acid ethyl ester

This compound was prepared in analogy to the procedure described in Example 23ii), starting from (3-chlorosulfonyl-1-methyl-1H-indol-7-yloxy)-acetic acid ethyl ester to obtain the desired compound as a yellowish solid. MS (ISN): m/e 311.3 (M−H)− iv) Ethyl {[3-({[(5-bromo-1,3-thiazol-2-yl)carbamoyl]amino}sulfonyl)-1-methyl-1H-indol-7-yl]oxy}acetate The title compound was prepared in analogy to the procedure described in Example 22iii) starting from (1-Methyl-3-sulfamoyl-1H-indol-7-yloxy)-acetic acid ethyl ester to obtain the desired compound as a creamy solid. MS (ISN): m/e 515.3, 517.2 (M−H)−

Example 51

2-{[3-({[(5-Bromo-1,3-thiazol-2-yl)carbamoyl]amino}sulfonyl)-1-methyl-1H-indol-7-yl]oxy}acetamide A solution of ethyl {[3-({[(5-bromo-1,3-thiazol-2-yl)carbamoyl]amino}sulfonyl)-1-methyl-1H-indol-7-yl]oxy}acetate (0.050 g, 0.09 mmol) in 7N ammonia/methanol, (5 mL) was heated at 40° C. for 5 h. The reaction mixture was concentrated to dryness and dried under high vacuum to obtain the title compound (0.040 g) as a grey amorphous solid. MS (ISN): m/e 486.4, 488.3 (M−H)−

Example 52

7-Methoxy-N-[(5-methoxy-4-methyl-1,3-thiazol-2-yl)carbamoyl]-1-methyl-1H-indole-3-sulfonamide i) 5-Methoxy-4-methyl-thiazol-2-ylamine

5-Bromo-4-methyl-thiazol-2-ylamine (0.5 g, 2.59 mmol) was dissolved in methanol abs. (10 mL). The solution was cooled with an ice-bath, then under stirring was added portionwise sodium methoxide (140 mg, 2.59 mmol) The black reaction mixture was stirred for 30 min. at rt then poured into a mixture of dichloromethane/water. The aqueous layer was extracted with two portions of dichloromethane. The combined, organic extracts were dried over magnesium sulfate, filtered and evaporated under reduced pressure to obtain the crude product which was used without further purification. MS (EI): m/e 144.1.

ii) 7-Methoxy-N-[(5-methoxy-4-methyl-1,3-thiazol-2-yl)carbamoyl]-1-methyl-1H-indole-3-sulfonamide The title compound was prepared in analogy to the procedure described in Example 33 starting from 7-methoxy-1-methyl-1H-indole-3-sulfonic acid amide (145 mg, 0.60 mmol) and 5-methoxy-4-methyl-thiazol-2-ylamine (405 mg, 1.80 mmol) to obtain the desired compound as a light brown amorphous solid: 7 mg, MS (ISN): m/e 409.1 (M−H)−

Example 53

2-{[3-({[(5-Methoxy-4-methyl-1,3-thiazol-2-yl)carbamoyl]amino}sulfonyl)-1-methyl-1H-indol-7-yl]oxy}acetamide i) Ethyl {[3-({[(5-methoxy-4-methyl-1,3-thiazol-2-yl)carbamoyl]amino}sulfonyl)-1-methyl-1H-indol-7-yl]oxy}acetate The title compound was prepared in analogy to the procedure described in Example 22iii) starting from (1-methyl-3-sulfamoyl-1H-indol-7-yloxy)-acetic acid ethyl ester and 5-methoxy-4-methyl-thiazol-2-ylamine to obtain the desired compound as a slightly orange colored solid. MS (ISN): m/e 481.1 (M−H)− ii) 2-{[3-({[(5-Methoxy-4-methyl-1,3-thiazol-2-yl)carbamoyl]amino}sulfonyl)-1-methyl-1H-indol-7-yl]oxy}acetamide The title compound was prepared in analogy to the procedure described in Example 51 starting from ethyl {[3-({[(5-methoxy-4-methyl-1,3-thiazol-2-yl)carbamoyl]amino}sulfonyl)-1-methyl-1H-indol-7-yl]oxy}acetate to obtain the desired compound as a slightly orange colored amorphous solid. MS (ISN): m/e 452.3 (M−H)−

Example 54

5-Methoxy-N-[(5-methoxy-1,3-thiazol-2-yl)carbamoyl]-1-benzothiophene-2-sulfonamide The title compound was prepared in analogy to the procedure described in Example 22iii) starting from 7-methoxy-benzo[b]thiophene-2-sulfonic acid amide (cf. Example 39ii) and 2-amino-5-methoxythiazole (Forlani, Luciano; Medici, Alessandro; Todesco, Paolo E., Tetrahedron Letters 1976, 3, 201-2) to obtain the desired compound as a creamy solid. MS (ISN): m/e 398.1 (M−H)−

Example 55

2-[5-({[(5-methoxy[1,3]thiazolo[5,4-b]pyridin-2-yl)carbamoyl]amino}sulfonyl)-3-methyl-2-thienyl]ethyl acetate i) Acetic acid 2-(3-methyl-thiophen-2-yl)-ethyl ester

A solution of 2-bromo-3-methylthiophene (35.4 g, 200 mmol, ALFA) in diethyl ether (200 mL) was added drop wise to Mg turnings (5.35 g, 220 mmol) over ~30 min at such a rate as to maintain gentle reflux (at the beginning the reaction was initiated with 2 drops of $Br_2$). After refluxing for 1 h, 2.0M ethylene oxide in THF (150 mL, 300 mmol) was added drop wise at 0° C. over 1 h and stirring was continued at rt for 20 h. After cooling to 0° C. acetyl chloride (22.8 mL, 320 mmol) was added drop wise at 0° C. over 15 min an the suspension was stirred at rt for 18 h. The reaction mixture was diluted with diethyl ether (200 mL) and washed with 1M HCl (200 mL) and 10% brine (200 mL). The aqueous layers were extracted with diethyl ether (100 mL) and the combined organic layers were dried ($Na_2SO_4$) and evaporated affording 49 g brownish oil which was purified by distillation affording 32.8 g (89.0%, GC 96.4%) colorless oil, bp ~120° C./10 mbar.

ii) Acetic acid 2-(5-chlorosulfonyl-3-methyl-thiophen-2-yl)-ethyl ester

A solution of the above prepared acetic acid 2-(3-methyl-thiophen-2-yl)-ethyl ester (32.6 g, 177 mmol) in DCM (180 mL) was added to a suspension of $SO_3$-DMF complex (33.5 g, 212.4 mmol) in DCM (330 mL) and the reaction mixture was refluxed for 2 h. Oxalyl chloride (30.0 mL, 354 mmol) was now added over 30 min and the brown solution was refluxed for 3 h. After cooling to rt the reaction mixture washed with 10% brine (2×300 mL), the aqueous layers were extracted with DCM (250 mL) and the combined organic layers were dried ($Na_2SO_4$) and evaporated affording 53, 4 g crude product as a brown oil which was used without further purification in the next step. $^1H$ NMR ($CDCl_3$, 250 MHz) □ 2.09 (s, 3H), 2.25 (s, 3H), 3.14 (t, 2H), 4.29 (t, 2H), 7.61 (s, 1H).

iii) Acetic acid 2-(3-methyl-5-sulfamoyl-thiophen-2-yl)-ethyl ester

To a solution of the above prepared crude acetic acid 2-(5-chlorosulfonyl-3-methyl-thiophen-2-yl)-ethyl ester (53.3 g, ca. 177 mmol) in DCM (180 mL) were added 25% aqueous $NH_3$ (53 mL, ~700 mmol) and the biphasic reaction mixture was vigorously stirred at rt for 18 h. After the addition of DCM (1200 mL) the reaction mixture was washed with 10% brine (2×400 mL) and the aqueous layers were extracted with DCM (600 mL). The combined organic layers were dried ($Na_2SO_4$) and evaporated affording 48.5 g yellow crystalline residue which was crystallized from hot isobutyl acetate (500 mL) affording 34.8 g (74.7%, GC 97.9%) product as a off white powder. ESI-MS (m/z) 286 (M+$Na^+$, 59); 264 (M+$H^+$, 19).

iv) 5-Methoxy-thiazolo[5,4-b]pyridin-2-ylamine

Potassium thiocyanate Fluka 60519 (38.8 g, 400 mmol, 8.0 equiv.) and 5-amino-2-methoxypyridine Aldrich A6, 120-9

(6.2 g, 50 mmol, 1.0 equiv.) were added to 100 mL glacial acetic acid precooled to 5° C. (semi solid) with mechanical stirring. Bromine (23.9 g, 150 mmol, 3.0 equiv.) dissolved in 30 mL glacial acetic acid was added dropwise to the reaction mixture over 1.5 hr at 0° C. The thick slurry was stirred 2 hrs at 0° C. and overnight at RT. Then 30 mL water was added to the orange suspension, which was heated to 85° C. and filtered hot. The residue was treated again with acetic acid, heated and filtered like before. The combined filtrates were cooled and neutralized with $NH_4OH$ at pH 6. The red precipitate was filtered, dissolved in ethyl acetate and washed with $NaHCO_3$ and brine, dried over $Na_2SO_4$, evaporated and crystallized from ethyl acetate-hexane using charcoal to give 5-methoxy-thiazolo[5,4-b]pyridin-2-ylamine m/e 182.0 ($MH^+$).

v) 2-[5-({[(5-Methoxy[1,3]thiazolo[5,4-b]pyridin-2-yl)carbamoyl]amino}sulfonyl)-3-methyl-2-thienyl] ethyl acetate The compound was prepared analogously to the procedure described for Example 45, using acetic acid 2-(3-methyl-5-sulfamoyl-thiophen-2-yl)-ethyl ester and 5-methoxy-thiazolo[5,4-b]pyridin-2-ylamine and purified by chromatography on a HPLC 75×30 mm RP18 5 μm column, with A=0.1% HCOOH and B=MeCN and with a gradient of 20% to 70% B in 10 min. The corresponding fractions were lyophilized to give 2-[5-({[(5-methoxy[1,3]thiazolo[5,4-b]pyridin-2-yl)carbamoyl]amino}sulfonyl)-3-methyl-2-thienyl]ethyl acetate, 80 mg, m/e 469.1 ($MH^-$).

Example 56

5-(2-Hydroxyethyl)-N-[(5-methoxy[1,3]thiazolo[5,4-b]pyridin-2-yl)carbamoyl]-4-methylthiophene-2-sulfonamide 2-[5-({[(5-Methoxy[1,3]thiazolo[5,4-b]pyridin-2-yl)carbamoyl]amino}sulfonyl)-3-methyl-2-thienyl]ethyl acetate (235 mg, 0.5 mmol, 1 equiv.) was saponified by addition of 1N LiOH (1 mL, 1 mmol, 2 equiv.) for 60 min. The solution was purified by chromatography on a HPLC 75×30 mm RP18 5 μm column, with A=0.1% HCOOH and B=MeCN and with a gradient of 20% to 70% B in 10 min. The corresponding fractions were lyophilized to give 5-(2-hydroxyethyl)-N-[(5-methoxy[1,3]thiazolo[5,4-b]pyridin-2-yl)carbamoyl]-4-methylthiophene-2-sulfonamide, 47 mg, m/e 427.0 ($MH^-$).

Example 57

N-[(5-Bromo-4-ethyl-1,3-thiazol-2-yl)carbamoyl]-5-methylthiophene-3-sulfonamide i) 4-Ethyl-thiazol-2-ylamine To a solution of 1-bromo-2-butanone (2.50 g, 15.7 mmol) in 25 mL of ethanol was added thiourea (1.20 g, 1.02 eq.) and the mixture vigorously stirred at 55-60° C. for 15 h. Pouring onto crashed ice/$Na_2CO_3$, twofold extraction with ethyl acetate, washing with water and brine, drying over sodium sulfate, and evaporation of the solvents left 2.10 g of the title product as viscous light yellow oil, sufficiently pure to be used for the next step.
MS (ISP): 129.0 $[M+H]^+$.

ii) 5-Bromo-4-ethyl-thiazol-2-ylamine

The above prepared 4-ethyl-thiazol-2-ylamine (1.125 g, 8.77 mmol) was dissolved in 4.5 mL of 20% aq. sulfuric acid, cooled to 0° C., and treated with $Br_2$ (0.494 mL, 1.1 eq.). After 10 Min., the reaction mixture was carefully poured onto crashed ice/$Na_2CO_3$, twofold extracted with ethyl acetate, washed with water, dried over sodium sulfate, and evaporated to dryness. Thereby, 1.306 g of the title compound was obtained as light brown viscous oil, sufficiently pure to be used for the next step.
MS (ISP): 207.0, 209.1 $[M+H]^+$.

iii) 5-Methyl-thiophene-3-sulfonic acid lithium salt

To a solution of 4-bromo-2-methyl-thiophene (1.594 g, 9.00 mmol) in 5.0 mL of diethyl ether was added dropwise 2.1 mL of tert-butyllithium in pentane (1.7 M, 09 eq.). After stirring for 20 Min. at −78° C., sulfur dioxide (condensed, ca. 4 mL) was added dropwise and the reaction mixture kept for another 30 min at this temperature. The dry ice cooling bath was removed and the reaction mixture diluted with heptane; the precipitated solid was collected, washed with some heptane and dried at high vacuum to yield 1.100 g of the title compound as white solid.
MS (ISP): 161.3 $(M-H)^-$.

iv) 5-Methyl-thiophene-3-sulfonic acid amide

To a solution of the above prepared 5-methyl-thiophene-3-sulfonic acid lithium salt (1.100 g, 6.03 mmol) in 5.0 ml of water was added 0.792 g of sodium acetate (1.6 eq.) and 1.024 g of hydroxylamine-O-sulfonic acid (1.5 eq.), and this mixture was stirred for 2 h at room temperature. HPLC showed complete conversion to the product. The reaction mixture was then partitioned between ethyl acetate and water, the layers were separated, the organic phase was washed with citric acid (10% in water), water and brine, dried over sodium sulfate, and the solvent was evaporated under reduced pressure. The residue was purified by silica column chromatography ($SiO_2$, hexane/ethyl acetate), to yield finally 0.745 g of the title compound as light yellow solid of mp. 105-106.5° C.
MS (ISP): 175.9 $(M-H)^-$.

v) N-[(5-bromo-4-ethyl-1,3-thiazol-2-yl)carbamoyl]-5-methylthiophene-3-sulfonamide 5-Methyl-thiophene-3-sulfonic acid amide (0.0496 g, 0.28 mmol) was dissolved in 1.5 mL of abs. acetonitrile and treated successively with phenyl chloroformate (0.0443 g, 1.01 eq.) and triethylamine (0.097 mL, 2.5 eq.), and the mixture kept at ambient temperature for 1.25 h. The above prepared 5-bromo-4-ethyl-thiazol-2-ylamine (0.061 g, 1.05 eq.), dissolved in a tiny amount of acetonitrile, was then added, and the mixture heated to 55-60° C. over night. Cooling, pouring onto crashed ice/NH4Cl, twofold extraction with ethyl acetate, washing with water, drying over sodium sulfate, and evaporation of the solvents, followed by flash chromatography ($SiO_2$, MeOH/ethyl acetate=1/99), yielded eventually, after precipitation from ethyl acetate/heptane, 0.038 g of the title compound as off-white solid.
MS (ISP): 410.0, 412.0 $[M+H]^+$.

Example 58

N-[(5-Bromo-4-ethyl-1,3-thiazol-2-yl)carbamoyl]-5-(2-methoxyethyl)-4-methylthiophene-2-sulfonamide The title compound was prepared in analogy to Example 57, but using in step 3 5-(2-methoxy-ethyl)-4-methylthiophene-2-sulfonic acid amide instead of 5-methyl-thiophene-3-sulfonic acid amide, as off-white solid.
MS (ISP): 468.0, 470.0 (M+H)+.

Example 59

N-[(5-Bromo-4-ethyl-1,3-thiazol-2-yl)carbamoyl]-4-(2-methoxyethyl)-5-methylthiophene-2-sulfonamide i) 2-(2-Methyl-thiophen-3-yl)-ethanol To a solution of 1.6M BuLi in hexane (98.4 mL, 157.5 mmol) and THF (150 mL) was added at −78° C. a solution of 3-bromo-2-methyl-thiophene (CAS 30319-05-2, 26.6 g, 150 mmol) in THF (50 mL) and stirring at −78° C. was continued for 1 h. 2.0M ethylene oxide in THF (112.5 mL, 225 mmol) and then $BF_3$-$Et_2O$ (20.4 mL, 165 mmol) was added dropwise at −70° C. and the yellow solution was stirred at −78° C. for 1 h. After warming to 0° C. the reaction mixture was quenched with 10% brine (400 mL) and extracted with ethyl acetate (400+200 mL). The organic layers were washed with 10% brine, dried ($Na_2SO_4$) and evaporated affording 18.6 g crude product as a yellow oil. Purification by chromatography over silica with hexane-ethyl acetate 5:1 gave 14.9 g (70%, GC 94.7%) yellow oil.

ii) 3-(2-Methoxy-ethyl)-2-methyl-thiophene

To a suspension of NaOtBu (3.00 g, 31.3 mmol) in THF (25 mL) was added the above prepared 2-(2-methyl-thiophen-3-yl)-ethanol (3.56 g, 25 mmol) and then methyl iodide (2.34 mL, 37.5 mmol). After stirring at rt for 1 h the reaction mixture was diluted with TBME (150 mL) and washed with 0.5M HCl (50 mL), 0.1M $Na_2S_2O_3$ (50 mL) and 10% brine. The aqueous layers were extracted with TBME (50 mL) and the combined organic layers were dried ($Na_2SO_4$) and evaporated affording 3.78 g (96.7%, GC 96.0%) crude product as a yellow oil which was used without purification in the next step.

iii) 4-(2-Methoxy-ethyl)-5-methyl-thiophene-2-sulfonyl chloride

A solution of the above prepared 3-(2-methoxy-ethyl)-2-methyl-thiophene (3.75 g, 24 mmol) in DCM (20 mL) was added to a suspension of $SO_3$-DMF complex (4.41 g, 28.8 mmol) in DCM (50 mL) and the reaction mixture was refluxed for 2 h. Oxalyl chloride (4.06 mL, 48 mmol) was now added over 30 min and the brown solution was refluxed for 1 h. After cooling to rt the reaction mixture was diluted with DCM (75 mL) and washed with $H_2O$ (75 mL) and 10% brine (3×75 mL). The aqueous layers were extracted with DCM (40 mL) and the combined organic layers were dried ($Na_2SO_4$) and evaporated affording 5.74 g crude product as a dark brown oil. Purification by chromatography over silica with heptane-ethyl acetate 12:1 yielded 4.8 g (78.5%, GC 96.2%) yellow oil. ESI-MS (m/z) 272 (M+$NH_4^+$, 100).

iv) 4-(2-Methoxy-ethyl)-5-methyl-thiophene-2-sulfonic acid amide

To a solution of the above prepared 4-(2-methoxy-ethyl)-5-methyl-thiophene-2-sulfonyl chloride (4.59 g, 18 mmol) in DCM (18 mL) were added 25% aqueous $NH_3$ (9 mL, ~120 mmol) and the biphasic reaction mixture was vigorously stirred at rt for 3 h. After the addition of DCM (120 mL) the reaction mixture was washed with $H_2O$ (2×120 mL) and the aqueous layers were extracted with DCM (50 mL). The combined organic layers were dried ($Na_2SO_4$) and evaporated affording 5.0 g crude product as a yellow viscous oil which was purified by chromatography over silica with hexane-ethyl acetate 2:1 providing 3.62 g (85% GC 96.3%) yellow viscous oil. ESI-MS (m/z) 253 (M+$NH_4^+$, 100).

v) N-[(5-Bromo-4-ethyl-1,3-thiazol-2-yl)carbamoyl]-4-(2-methoxyethyl)-5-methylthiophene-2-sulfonamide The title compound was prepared in analogy to Example 57, but using in step 3 4-(2-methoxy-ethyl)-5-methyl-thiophene-2-sulfonic acid amide instead of 5-methyl-thiophene-3-sulfonic acid amide, as off-white solid.
MS (ISP): 465.9, 468.0 (M−H)−.

Example 60

N-[(5-Ethyl-4-methyl-1,3-thiazol-2-yl)carbamoyl]-5-(2-methoxyethyl)-4-methylthiophene-2-sulfonamide i) 5-Iodo-4-methyl-thiazol-2-ylamine 4-Methyl-thiazol-2-ylamine (1.50 g, 13.14 mmol) was dissolved in 30 mL of $CH_2Cl_2$ and 6 mL of acetic acid and treated at 0° C. with iodine monochloride (13.8 mL of 1M in $CH_2Cl_2$, 1.05 eq.) and kept at this temperature for 1 h. Pouring onto crashed ice/$Na_2CO_3$, twofold extraction with ethyl acetate, washing with water and brine, drying over sodium sulfate, and evaporation to dryness afforded 3.10 g of the title compound as brown crystals, sufficiently pure to be used for the next step.
MS (ISP): 241.1 [M+H]+.

ii) (5-Iodo-4-methyl-thiazol-2-yl)-carbamic acid tert-butyl ester

The above prepared 5-iodo-4-methyl-thiazol-2-ylamine (2.768 g, 12 mmol) was dissolved in 30 mL of tBuOH and treated successively with $BOC_2O$ (3.02 g, 1.2 eq.), DMAP (0.141 g, 0.1 eq.), and $NaHCO_3$ (3.39 g, 3.5 eq.). After stirring for 18 h at ambient temperature, the reaction mixture was poured onto icewater/$NH_4Cl$, twofold extracted with ethyl acetate, washed with water and brine, dried over magnesium sulfate, and evaporated to dryness. Ensuing flash chromatography ($SiO_2$, hexane/ethyl acetate=8/2), yielded finally 2.383 g of the title compound as off-white foam.
MS (ISP): 285.0 [M+H−tBu]+, 340.9 [M+H]+.

iii) (4-Methyl-5-trimethylsilanylethynyl-thiazol-2-yl)-carbamic acid tert-butyl ester Under a stream of Ar the above prepared (5-iodo-4-methyl-thiazol-2-yl)-carbamic acid tert-butyl ester (0.913 g, 2.68 mmol) was dissolved in 17 mL of acetonitrile and treated successively with triethylamine (1.12 mL, 3 eq.), CuI (0.051 g, 0.1 eq.), $(Ph_3P)_2PdCl_2$ (0.188 g, 0.1 eq.), and ethynyltrimethylsilane (1.11 mL, 3 eq.). The flask was closed with a septum and allowed to stir for 4 h at 32° C. The reaction mixture was then poured onto icewater/$NH_4Cl$, twofold extracted with ethyl acetate, washed with water and brine, dried over sodium sulfate, and evaporated to dryness. Flash chromatography ($SiO_2$, hexane/ethyl acetate=85/15) gave finally 0.592 g of the title compound as light brown foam.
MS (ISP): 255.3 [M+H−tBu]+.

iv) (5-Ethynyl-4-methyl-thiazol-2-yl)-carbamic acid tert-butyl ester

To the above prepared (4-methyl-5-trimethylsilanylethynyl-thiazol-2-yl)-carbamic acid tert-butyl ester (0.592 g, 1.907 mmol), dissolved in 10 mL of MeOH, was added $K_2CO_3$ (0.395 g, 1.5 eq.)) and the mixture was stirred for 2 h at ambient temperature. Pouring onto crashed ice/$NH_4Cl$, twofold extraction with ethyl acetate, washing with water and brine, drying over sodium sulfate, and evaporation to dryness, followed by flash chromatography ($SiO_2$, hexane/ethyl acetate=4/1), produced 0.391 g of the title compound as light brown foam.

MS (ISP): 183.1 [M+H-tBu]$^+$.

v) (5-Ethyl-4-methyl-thiazol-2-yl)-carbamic acid tert-butyl ester

The above prepared (5-ethynyl-4-methyl-thiazol-2-yl)-carbamic acid tert-butyl ester (0.420 g, 1.76 mmol) was dissolved in 12 mL of ethyl acetate and hydrogenated over 0.200 g of Pd on charcoal (10%) at atmospheric pressure and ambient temperature over night. Filtration over a pad of Celite and evaporation off all solvents yielded 0.396 g of the title product as light brown viscous oil, sufficiently pure for the next step.

MS (ISP): 187.1 [M+H-tBu]$^+$.

vi) 5-Ethyl-4-methyl-thiazol-2-ylamine

The above prepared (5-ethyl-4-methyl-thiazol-2-yl)-carbamic acid tert-butyl ester (0.394 g, 1.626 mmol) was dissolved in 8 mL of $CH_2Cl_2$ and treated with 1.5 mL of TFA. After 2 h at RT all starting material had disappeared. The reaction mixture was then poured onto icewater/$NaHCO_3$, twofold extracted with ethyl acetate, washed with water and brine, dried over sodium sulfate, and evaporated to dryness. Flash chromatography ($SiO_2$, hexane/ethyl acetate=1/1) yielded 0.200 g of the title compound as light brown viscous oil.

MS (ISP): 143.1 [M+H]$^+$.

vii) N-[(5-ethyl-4-methyl-1,3-thiazol-2-yl)carbamoyl]-5-(2-methoxyethyl)-4-methylthiophene-2-sulfonamide 5-(2-Methoxy-ethyl)-4-methyl-thiophene-2-sulfonic acid amide (0.1556 g, 0.661 mmol) was dissolved in 4 mL of abs. acetonitrile and treated successively with phenyl chloroformate (0.103 g, 1.00 eq.) and triethylamine (0.229 mL, 2.5 eq.), and the mixture kept at ambient temperature for 1 h. The above prepared 5-ethyl-4-methyl-thiazol-2-ylamine (0.094 g, 1.00 eq.), dissolved in a tiny amount of acetonitrile, was then added, and the mixture heated to 60° C. over night. Cooling, pouring onto crashed ice/NH4Cl, twofold extraction with ethyl acetate, washing with brine, drying over magnesium sulfate, and evaporation of the solvents, followed by flash chromatography ($SiO_2$, ethyl acetate), yielded eventually 0.089 g of the title compound as light brown solid.

MS (ISP): 402.3 (M–H)$^-$.

Example 61

N-[(4-Ethyl-5-methoxy-1,3-thiazol-2-yl)carbamoyl]-5-methylthiophene-3-sulfonamide i) 4-Ethyl-5-methoxy-thiazol-2-ylamine

Sodium methoxide was freshly prepared by dissolving 0.186 g (8.1 mmol) of sodium metal in 12 mL of abs. MeOH. After cooling to 0° C., 5-bromo-4-ethyl-thiazol-2-ylamine (0.519 g, 2.51 mmol) was added and the cooling bath removed. After 45 min, TLC indicated the absence of starting material. The reaction mixture was poured onto crashed ice, twofold extracted with ethyl acetate, washed with brine, dried over sodium sulfate, and evaporated to dryness. Thereby, 0.298 g of the title compound was obtained as brown, rather unstable oil, sufficiently pure to be used for the next step; it should be stored at –28° C.

MS (ISP): 159.1 [M+H]$^+$.

ii) N-[(4-Ethyl-5-methoxy-1,3-thiazol-2-yl)carbamoyl]-5-methylthiophene-3-sulfonamide The title compound was prepared in analogy to Example 57, but using in step 3 4-ethyl-5-methoxy-thiazol-2-ylamine instead of 5-bromo-4-ethyl-thiazol-2-ylamine, as light brown powder.

MS (ISP): 360.1 (M–H)$^-$.

Example 62

N-[(4,5-Diethyl-1,3-thiazol-2-yl)carbamoyl]-5-methylthiophene-3-sulfonamide i) 4-Ethyl-5-iodo-thiazol-2-ylamine

4-Ethyl-thiazol-2-ylamine (0.960 g, 7.49 mmol) was dissolved in 17 mL of $CH_2Cl_2$ and 3.5 mL of acetic acid and treated at 0° C. with iodine monochloride (7.86 mL of 1M in $CH_2Cl_2$, 1.05 eq.) and kept at this temperature for 1 h. Pouring onto crashed ice/$Na_2CO_3$, twofold extraction with ethyl acetate, washing with water and brine, drying over sodium sulfate, and evaporation to dryness afforded 1.67 g of the title compound as almost black viscous oil, sufficiently pure to be used for the next step.

MS (ISP): 255.1 [M+H]$^+$.

ii) 4-Ethyl-5-trimethylsilanylethynyl-thiazol-2-ylamine

Under a stream of Ar the above prepared 4-ethyl-5-iodo-thiazol-2-ylamine (1.67 g, 6.57 mmol) was dissolved in 40 mL of acetonitrile and treated successively with triethylamine (2.73 mL, 3 eq.), CuI (0.125 g, 0.1 eq.), $(Ph_3P)_2PdCl_2$ (0.46 g, 0.1 eq.) and ethynyltrimethylsilane (2.73 mL, 3 eq.). The flask was closed with a septum and allowed to stir for 15 h at ambient temperature. The reaction mixture was then poured onto icewater/$NH_4Cl$, twofold extracted with ethyl acetate, washed with water and brine, dried over sodium sulfate, and evaporated to dryness. Flash chromatography ($SiO_2$, hexane/AcOEt=7/3) afforded finally 0.598 g of the title compound as brown viscous oil, contaminated with some des-iodo-compound.

MS (ISP): 225.3 [M+H]$^+$.

iii) 4-Ethyl-5-ethynyl-thiazol-2-ylamine

To the above prepared 4-ethyl-5-trimethylsilanylethynyl-thiazol-2-ylamine (0.595 g, 2.651 mmol), dissolved in 9 mL of MeOH, was added $K_2CO_3$ (0.550 g, 1.5 eq.) and the mixture was stirred for 2 h at ambient temperature. Pouring onto crashed ice/$NH_4Cl$, twofold extraction with ethyl acetate, washing with water and brine, drying over sodium sulfate, and evaporation to dryness, followed by flash chromatography ($SiO_2$, hexane/ethyl acetate=7/3), produced 0.256 g of the title compound as light brown solid.

MS (ISP): 153.3 [M+H]$^+$.

iv) 4,5-Diethyl-thiazol-2-ylamine

The above prepared 4-ethyl-5-ethynyl-thiazol-2-ylamine (0.255 g, 1.675 mmol) was dissolved in 8 mL of ethyl acetate and hydrogenated over 0.125 g of Pd on charcoal (10%) at atmospheric pressure and ambient temperature over night. Filtration over a pad of Ceite and evaporation off all solvents, followed by flash chromatography (SiO$_2$, hexane/ethyl acetate=6/4), yielded 0.184 g of the title product as light yellow solid.
MS (ISP): 157.3 [M+H]$^+$.

v) N-[(4,5-Diethyl-1,3-thiazol-2-yl)carbamoyl]-5-methylthiophene-3-sulfonamide The title compound was prepared in analogy to Example 57, but using in step 3 4,5-diethyl-thiazol-2-ylamine instead of 5-bromo-4-ethyl-thiazol-2-ylamine, as off-white solid.
MS (ISP): 358.0 (M−H)$^-$.

Example 63

N-[(4,5-Diethyl-1,3-thiazol-2-yl)carbamoyl]-5-(2-methoxyethyl)-4-methylthiophene-2-sulfonamide The title compound was prepared in analogy to Example 62, but using in the last step 5-(2-methoxy-ethyl)-4-methyl-thiophene-2-sulfonic acid amide instead of 5-methyl-thiophene-3-sulfonic acid amide, as off-white solid.
MS (ISP): 416.1 (M−H)$^-$.

Example 64

2-[5-({[(5-Bromo-4-methyl-1,3-thiazol-2-yl)carbamoyl]amino}sulfonyl)-3-methyl-2-thienyl]ethyl acetate i) 5-Bromo-4-methyl-thiazol-2-ylamine

4-Methyl-thiazol-2-ylamine (4.00 g, 35.0 mmol) was dissolved in 17.5 mL of 20% aq. sulfuric acid, cooled to 0° C., and treated drop wise with Br$_2$ (1.97 mL, 1.1 eq.). After 10 Min. at 0° C. and 60 Min. at RT, the reaction mixture was carefully poured onto crashed ice/Na$_2$CO$_3$, twofold extracted with AcOEt, washed with water, dried over sodium sulfate, and evaporated to dryness. Thereby, 5.20 g of the title compound was isolated as light brown solid, sufficiently pure to be used for the next step.
MS (ISP): 193.1, 195.1 [M+H]$^+$.

ii) 2-[5-({[(5-Bromo-4-methyl-1,3-thiazol-2-yl)carbamoyl]amino}sulfonyl)-3-methyl-2-thienyl]ethyl acetate Acetic acid 2-(3-methyl-5-sulfamoyl-thiophen-2-yl)-ethyl ester (0.120 g, 0.456 mmol) was dissolved in 4.5 mL of abs. acetonitrile and treated successively with phenyl chloroformate (0.057 g, 1.00 eq.) and triethylamine (0.159 mL, 2.5 eq.), and the mixture kept at ambient temperature for 1 h. 5-Bromo-4-methyl-thiazol-2-ylamine (0.088 g, 1.00 eq.), dissolved in a tiny amount of acetonitrile, was then added, and the mixture heated to 60° C. over night. Cooling, pouring onto crashed ice/NH4Cl, twofold extraction with ethyl acetate, washing with brine, drying over sodium sulfate, and evaporation of the solvents, followed by flash chromatography (SiO$_2$, ethyl acetate/5% MeOH), followed by crystallization from ethyl acetate/heptane, yielded finally 0.089 g of the title compound as light brown solid.
MS (ISP): 479.8, 481.9 (M−H)$^-$.

Example 65

5-Methyl-N-[(5-methyl-4-phenyl-1,3-thiazol-2-yl)carbamoyl]thiophene-3-sulfonamide i) 5-Methyl-4-phenyl-thiazol-2-ylamine

To a solution of 2-bromo-1-phenyl-propan-1-one (3.64 g, 17.1 mmol) in 30 mL of ethanol was added thiourea (1.30 g, 1.00 eq.) and the mixture vigorously stirred at 55-60° C. for 4 h. Pouring onto crashed ice/Na$_2$CO$_3$, twofold extraction with ethyl acetate, washing with water and brine, drying over sodium sulfate, and evaporation of the solvents, followed by crystallization from ethyl acetate/hexane, left 2.87 g of the title product as off-white crystals.
MS (ISP): 191.1 [M+H]$^+$.

ii) 5-Methyl-N-[(5-methyl-4-phenyl-1,3-thiazol-2-yl)carbamoyl]thiophene-3-sulfonamide The title compound was prepared in analogy to Example 57, but using in the last step 5-methyl-4-phenyl-thiazol-2-ylamine instead of 5-bromo-4-ethyl-thiazol-2-ylamine, as white crystals.
MS (ISP): 392.0 (M−H)$^-$.

Example 66

5-(2-Methoxyethyl)-4-methyl-N-[(5-methyl-4-phenyl-1,3-thiazol-2-) carbamoyl]thiophene-2-sulfonamide The title compound was prepared in analogy to Example 65, but using in the last step 5-(2-methoxy-ethyl)-4-methyl-thiophene-2-sulfonic acid amide instead of 5-methyl-thiophene-3-sulfonic acid amide, as off-white crystals.
MS (ISP): 450.1 (M−H)$^-$.

Example 67

2-[5-({[(4,5-Diethyl-1,3-thiazol-2-yl)carbamoyl]amino}sulfonyl)-3-methyl-2-thienyl]ethyl acetate The title compound was prepared in analogy to Example 63, but using in the last step acetic acid 2-(3-methyl-5-sulfamoyl-thiophen-2-yl)-ethyl ester instead of 5-(2-methoxy-ethyl)-4-methyl-thiophene-2-sulfonic acid amide, as light yellow solid.
MS (ISP): 444.0 (M−H)$^-$.

Example 68

2-[5-({[(5-Ethyl-4-methyl-1,3-thiazol-2-yl)carbamoyl]amino}sulfonyl)-3-methyl-2-thienyl]ethyl acetate The title compound was prepared in analogy to Example 60, but using in the last step acetic acid 2-(3-methyl-5-sulfamoyl-thiophen-2-yl)-ethyl ester instead of 5-(2-methoxy-ethyl)-4-methyl-thiophene-2-sulfonic acid amide, as yellow solid.
MS (ISP): 430.1 (M−H)$^-$.

Example 69

N-[(4,5-Diethyl-1,3-thiazol-2-yl)carbamoyl]-5-(2-hydroxyethyl)-4-methylthiophene-2-sulfonamide Example 63 (0.097 g, 0.218 mmol) was dissolved in 1 mL of MeOH, cooled to 0° C., and treated with NaOMe-solution (0.089 mL, 5.4 M in MeOH, 2.2 eq.). After 30 Min. at 0° C., TLC indicated the absence of starting material; the reaction mixture was poured onto crashed ice/$NH_4Cl$, twofold extracted with AcOEt, washed with water, dried over sodium sulfate, and evaporated to dryness. Triturating from heptane afforded 0.080 g of the title product as yellow solid.

MS (ISP): 402.1 (M−H)⁻.

Example 70

N-[(5-Ethyl-4-methyl-1,3-thiazol-2-yl)carbamoyl]-5-(2-hydroxyethyl)-4-methylthiophene-2-sulfonamide The title compound was prepared in analogy to Example 69, but hydrolysing in the last step Example 68 to yield a yellow solid.

MS (ISP): 388.1 (M−H)⁻.

Example 71

N-[(5-Ethyl-4-phenyl-1,3-thiazol-2-yl)carbamoyl]-5-methylthiophene-3-sulfonamide i) 5-Iodo-4-phenyl-thiazol-2-ylamine

4-Phenyl-thiazol-2-ylamine (0.881 g, 5.00 mmol) was dissolved in 10 mL of $CH_2Cl_2$ and 2 mL of acetic acid and treated at 0° C. with iodine monochloride (5.25 mL of 1M in $CH_2Cl_2$, 1.05 eq.) and kept at this temperature for 0.5 h. Pouring onto crashed ice/$Na_2CO_3$, twofold extraction with ethyl acetate, washing with water and brine, drying over sodium sulfate, and evaporation to dryness produced 1.60 g of the title compound as dark brown gum, sufficiently pure to be used for the next step.

MS (ISP): 302.9 [M+H]⁺.

ii) 4-Phenyl-5-trimethylsilanylethynyl-thiazol-2-ylamine

Under a stream of Ar the above prepared 5-iodo-4-phenyl-thiazol-2-ylamine (1.60 g, 5.29 mmol) was dissolved in 30 mL of acetonitrile and treated successively with triethylamine (2.09 mL, 3 eq.), CuI (0.096 g, 0.1 eq.), $(Ph_3P)_2PdCl_2$ (0.353 g, 0.1 eq. and ethynyltrimethylsilane (2.09 mL, 3 eq.). The flask was closed with a septum and allowed to stir for 15 h at ambient temperature. The reaction mixture was then poured onto icewater/$NH_4Cl$, twofold extracted with ethyl acetate, washed with water and brine, dried over sodium sulfate, and evaporated to dryness. Flash chromatography ($SiO_2$, hexane/ethyl acetate=8/2) yielded finally 1.075 g of the title compound as brown foam. MS (ISP): 273.3 [M+H]⁺.

iii) 5-Ethynyl-4-phenyl-thiazol-2-ylamine

To the above prepared 4-phenyl-5-trimethylsilanylethynyl-thiazol-2-ylamine (1.070 g, 3.927 mmol), dissolved in 14 mL of MeOH, was added $K_2CO_3$ (0.814 g, 1.5 eq.)) and the mixture was stirred for 2 h at ambient temperature. Pouring onto crashed ice/$NH_4Cl$, twofold extraction with ethyl acetate, washing with water and brine, drying over sodium sulfate, and evaporation to dryness, followed by flash chromatography ($SiO_2$, hexane/ethyl acetate=7/3), gave 0.667 g of the title compound as dark brown viscous oil.

MS (ISP): 201.1 [M+H]⁺.

iv) 5-Ethyl-4-phenyl-thiazol-2-ylamine

The above prepared 5-ethynyl-4-phenyl-thiazol-2-ylamine (0.665 g, 3.321 mmol) was dissolved in 12 mL of ethyl acetate and hydrogenated over 0.330 g of Pd on charcoal (10%) at atmospheric pressure and ambient temperature over night. Filtration over a pad of Celite and evaporation off all solvents, followed by flash chromatography ($SiO_2$, hexane/ethyl acetate=65/35), yielded 0.505 g of the title product as yellow viscous oil.

MS (ISP): 205.3 [M+H]⁺.

v) N-[(5-ethyl-4-phenyl-1,3-thiazol-2-yl)carbamoyl]-5-methylthiophene-3-sulfonamide 5-Methyl-thiophene-3-sulfonic acid amide (0.0789 g, 0.445 mmol) was dissolved in 4 mL of abs. acetonitrile and treated successively with phenyl chloroformate (0.0697 g, 1.00 eq.) and triethylamine (0.154 mL, 2.5 eq.), and the mixture kept at ambient temperature for 1. h. The above prepared 5-ethyl-4-phenyl-thiazol-2-ylamine (0.0910 g, 1.00 eq.), dissolved in a tiny amount of acetonitrile, was then added, and the mixture heated to 55-60° C. over night. Cooling, pouring onto crashed ice/NH4Cl, twofold extraction with ethyl acetate, washing with brine, drying over magnesium sulfate, and evaporation of the solvents, followed by flash chromatography ($SiO_2$, hexane/ethyl acetate=1/1), yielded 0.081 g of the title compound as off-white crystals.

MS (ISP): 406.2 (M−H)⁻.

Example 72

N-[(5-Ethyl-4-phenyl-1,3-thiazol-2-yl)carbamoyl]-5-(2-methoxyethyl)-4-methylthiophene-2-sulfonamide The title compound was prepared in analogy to Example 71, but using in the last step 5-(2-methoxy-ethyl)-4-methyl-thiophene-2-sulfonic acid amide instead of 5-methyl-thiophene-3-sulfonic acid amide, as off-white crystals.

MS (ISP): 464.1 (M−H)⁻.

Example 73

2-[3-Methyl-5-({[(5-methyl-4-phenyl-1,3-thiazol-2-yl)carbamoyl]amino}sulfonyl)-2-thienyl]ethyl acetate The title compound was prepared in analogy to Example 65, but using in the last step acetic acid 2-(3-methyl-5-sulfamoyl-thiophen-2-yl)-ethyl ester instead of 5-methyl-thiophene-3-sulfonic acid amide, as off-white solid.

MS (ISP): 478.0 (M−H)⁻.

Example 74

2-[5-({[(5-Methoxy-4-methyl-1,3-thiazol-2-yl)carbamoyl]amino}sulfonyl)-3-methyl-2-thienyl]ethyl acetate i) 5-Methoxy-4-methyl-thiazol-2-ylamine

Sodium methoxide was freshly prepared by dissolving 0.408 g (17.7 mmol) of sodium metal in 25 mL of abs. MeOH.

After cooling to 0° C., 5-bromo-4-methyl-thiazol-2-ylamine (1.00 g, 5.18 mmol) was added and the cooling bath removed. After 15 Min., TLC indicated the absence of starting material. The reaction mixture was poured onto crashed ice/NH$_4$Cl, twofold extracted with ethyl acetate, washed with water, dried over sodium sulfate, and evaporated to dryness. Flash chromatography (SiO$_2$, hexane/ethyl acetate=1/1), yielded 0.441 g of the title compound as brown oil; it should be stored at −28° C.

MS (ISP): 145.1 [M+H]$^+$.

ii) 2-[5-({[(5-Methoxy-4-methyl-1,3-thiazol-2-yl)carbamoyl]amino}sulfonyl)-3-methyl-2-thienyl]ethyl acetate The title compound was prepared in analogy to Example 64, but using in the last step 5-methoxy-4-methyl-thiazol-2-ylamine instead of 5-bromo-4-methyl-thiazol-2-ylamine, as brown solid.

MS (ISP): 432.1 (M−H)$^−$.

Example 75

2-[5-({[(5-Ethyl-4-isopropyl-1,3-thiazol-2-yl)carbamoyl]amino}sulfonyl)-3-methyl-2-thienyl]ethyl acetate i) Trimethyl-(2-methyl-1-methylene-propoxy)-silane To freshly prepared LDA-solution in THF/hexane (1.05 eq.) was added slowly at −78° C. chloro-trimethyl-silane 7.59 mL, 60 mmol, 1.2 eq.), followed by 3-methyl-butan-2-one 5.32 mL, 50 mmol). The reaction vessel was kept for 30 Min. at −78° C. and then allowed to reach RT. The reaction mixture was diluted with 200 mL of pentane and filtered. All volatile solvents were then evaporated from the filtrate and the residue distilled in vacuo (50 mbar, bp. 40-45° C.) to give 4.38 g of regioisomerically pure title compound as colorless liquid.

ii) 1-Bromo-3-methyl-butan-2-one

The above prepared trimethyl-(2-methyl-1-methylene-propoxy)-silane (4.30 g, 27.2 mmol) was dissolved in 120 mL of pentane and treated via dropping funnel at −78° C. with a solution of bromine in pentane (9.05 mL, 3M) The reaction mixture was kept for 30 Min. at −78° C. and then allowed to reach RT. Pouring onto crashed ice, twofold extraction with pentane, washing with water, drying over sodium sulfate, and evaporation of all volatile solvents left 3.58 g of the title product as colorless liquid.

iii) 4-Isopropyl-thiazol-2-ylamine

To a solution of the above prepared 1-bromo-3-methyl-butan-2-one (3.58 g, 21.6 mmol) in 40 mL of ethanol was added thiourea (1.64 g, 1.00 eq.) and the mixture vigorously stirred at 55-60° C. for 3 h. Pouring onto crashed ice/Na$_2$CO$_3$, twofold extraction with ethyl acetate, washing with water and brine, drying over sodium sulfate, and evaporation of the solvents, followed by flash chromatography (SiO$_2$, hexane/ethyl acetate=6/4), left 2.996 g of the title product as colorless oil.

MS (ISP): 143.1 [M+H]$^+$.

iv) 5-Iodo-4-isopropyl-thiazol-2-ylamine

The above prepared 4-isopropyl-thiazol-2-ylamine (1.020 g, 7.17 mmol) was dissolved in 14 mL of CH$_2$Cl$_2$ and 2.8 mL of acetic acid and treated at 0° C. with iodine monochloride (7.53 mL of 1M in CH$_2$Cl$_2$, 1.05 eq.) and kept at this temperature for 0.5 h. Pouring onto crashed ice/Na$_2$CO$_3$, twofold extraction with ethyl acetate, washing with water and brine, drying over sodium sulfate, and evaporation to dryness yielded 1.922 g of the title compound as dark brown viscous oil, sufficiently pure to be used for the next step.

MS (ISP): 269.0 [M+H]$^+$.

v) 2-[5-({[(5-Ethyl-4-isopropyl-1,3-thiazol-2-yl)carbamoyl]amino}sulfonyl)-3-methyl-2-thienyl]ethyl acetate The title compound was prepared in analogy to example 67, but starting the reaction sequence with 5-iodo-4-isopropyl-thiazol-2-ylamine instead of 4-ethyl-5-iodo-thiazol-2-ylamine, as light yellow crystals.

MS (ISP): 458.2 (M−H)$^−$.

Example 76

5-(2-Hydroxyethyl)-4-methyl-N-[(5-methyl-4-phenyl-1,3-thiazol-2-yl)carbamoyl]thiophene-2-sulfonamide The title compound was prepared from Example 73 with NaOMe as described in Example 68 as white crystals.

MS (ISP): 436.1 (M−H)$^−$.

Example 77

N-[(5-Ethyl-4-isopropyl-1,3-thiazol-2-yl)carbamoyl]-5-(2-methoxyethyl)-4-methylthiophene-2-sulfonamide The title compound was prepared in analogy to Example 75, but using in the last step 5-(2-methoxy-ethyl)-4-methyl-thiophene-2-sulfonic acid amide instead of acetic acid 2-(3-methyl-5-sulfamoyl-thiophen-2-yl)-ethyl ester, as off-white crystals.

MS (ISP): 430.3 (M−H)$^−$.

Example 78

N-[(5-Ethyl-4-isopropyl-1,3-thiazol-2-yl)carbamoyl]-5-methylthiophene-3-sulfonamide The title compound was prepared in analogy to Example 75, but using in the last step 5-methyl-thiophene-3-sulfonic acid amide instead of acetic acid 2-(3-methyl-5-sulfamoyl-thiophen-2-yl)-ethyl ester, as off-white crystals.

MS (ISP): 372.1 (M−H)$^−$.

Example 79

N-[(5-Ethyl-4-isopropyl-1,3-thiazol-2-yl)carbamoyl]-5-(2-hydroxyethyl)-4-methylthiophene-2-sulfonamide The title compound was prepared from Example 75 with NaOMe as described in Example 69 as white crystals.

MS (ISP): 416.2 (M−H)$^−$.

Example 80

2-[5-({[(5-Ethyl-4-phenyl-1,3-thiazol-2-yl)carbamoyl]amino}sulfonyl)-3-methyl-2-thienyl]ethyl acetate The title compound was prepared in analogy to Example 71, but using in the last step acetic acid 2-(3-methyl-5-sulfamoyl-thiophen-2-yl)-ethyl ester instead of 5-methyl-thiophene-3-sulfonic acid amide, as light brown crystals.
MS (ISP): 492.0 (M−H)⁻.

Example 81

N-[(5-Ethyl-4-phenyl-1,3-thiazol-2-yl)carbamoyl]-5-(2-hydroxyethyl)-4-methylthiophene-2-sulfonamide The title compound was prepared from Example 80 with NaOMe as described in Example 69 as white crystals.
MS (ISP): 450.1 (M−H)⁻.

Example 82

N-{[4-Ethyl-5-(methylthio)-1,3-thiazol-2-yl]carbamoyl}-5-(2-methoxyethyl)-4-methylthiophene-2-sulfonamide i) (4-Ethyl-thiazol-2-yl)-carbamic acid tert-butyl ester The above prepared 4-ethyl-thiazol-2-ylamine (1.50 g, 11.7 mmol) was dissolved in 23 mL of tBuOH and treated successively with DMAP (0.143 g, 0.1 eq.), NaHCO₃ (2.46 g, 2.5 eq.) and BOC₂O (2.81 g, 1.1 eq.). After stirring for 0.5 h at 40° C., the reaction mixture was poured onto icewater/NH₄Cl, twofold extracted with ethyl acetate, washed with water, dried over sodium sulfate, and evaporated to dryness. Ensuing flash chromatography (SiO₂, heptane/ethyl acetate=85/15), yielded finally 2.04 g of the title compound as yellow solid.
MS (ISP): 173.3 [M+H−tBu]⁺, 229.1 [M+H]⁺.

ii) (4-Ethyl-5-methylsulfanyl-thiazol-2-yl)-carbamic acid tert-butyl ester

The above prepared (4-ethyl-thiazol-2-yl)-carbamic acid tert-butyl ester (1.12 g, 4.90 mmol) was dissolved in 12 mL of abs. THF and treated at −78° C. with a solution of nBuLi in hexane (6.53 mL, 1.5M, 2 eq.). The reaction mixture was kept for 15 Min. at −78° C. and then allowed to reach RT. After recooling to −78° C., methyldisulfanylmethane (0.870 mL, 2 eq.) was added and the mixture kept for 30 Min. at this temperature and then slowly warmed to RT. Pouring onto crashed ice/NH₄Cl, twofold extraction with ethyl acetate washing with water, drying over sodium sulfate, and evaporation of the solvents, followed by flash chromatography (SiO₂, hexane/ethyl acetate=85/15), afforded 1.067 g of the title product as off-white solid.
MS (ISP): 219.1 [M+H−tBu]⁺.

iii) 4-Ethyl-5-methylsulfanyl-thiazol-2-ylamine

The above prepared (4-ethyl-5-methylsulfanyl-thiazol-2-yl)-carbamic acid tert-butyl ester (1.067 g, 3.888 mmol) was treated with 20 mL of HCl (4 M in dioxane). After 48 h at RT the reaction mixture was evaporated to dryness and, since still some starting material was present, the procedure repeated, but this time the temperature was raised to 30° C. Careful evaporation and drying left 0.814 g of the title compound as hydrochloride.
MS (ISP): 175.3 (M+H)⁺.

iv) N-{[4-ethyl-5-(methylthio)-1,3-thiazol-2-yl]carbamoyl}-5-(2-methoxyethyl)-4-methylthiophene-2-sulfonamide 5-(2-Methoxy-ethyl)-4-methyl-thiophene-2-sulfonic acid amide (0.235 g, 1.00 mmol) was dissolved in 6 mL of abs. acetonitrile and treated successively with phenyl chloroformate (0.157 g, 1.00 eq.) and triethylamine (0.348 mL, 2.5 eq.), and the mixture kept at ambient temperature for 1. h. The above prepared 4-ethyl-5-methylsulfanyl-thiazol-2-ylamine (0.211 g, 1.00 eq. as hydrochloride) was then added, and the mixture heated to 60° C. over night. Cooling, pouring onto crashed ice, twofold extraction with ethyl acetate, washing with brine, drying over sodium sulfate, and evaporation of the solvents, followed by flash chromatography (SiO₂, ethyl acetate/MeOH=95/5) and trituration over heptane yielded 0.296 g of the title compound as light brown solid.
MS (ISP): 434.0 (M−H)⁻.

Example 83

2-{5-[({[4-Ethyl-5-(methylthio)-1,3-thiazol-2-yl]carbamoyl}amino)sulfonyl]-3-methyl-2-thienyl}ethyl acetate The title compound was prepared in analogy to Example 82, but using in the last step acetic acid 2-(3-methyl-5-sulfamoyl-thiophen-2-yl)-ethyl ester instead of 5-(2-methoxyethyl)-4-methyl-thiophene-2-sulfonic acid amide, as light brown solid.
MS (ISP): 462.0 (M−H)⁻.

Example 84

N-{[4-Ethyl-5-(methylthio)-1,3-thiazol-2-yl]carbamoyl}-5-(2-hydroxyethyl)-4-methylthiophene-2-sulfonamide The title compound was prepared from Example 83 with NaOMe as described in Example 69 as white crystals.
MS (ISP): 420.0 (M−H)⁻.

Example 85

2-{3-Methyl-5-[({[4-methyl-5-(methylthio)-1,3-thiazol-2-yl]carbamoyl}amino)sulfonyl]-2-thienyl}ethyl acetate i) 4-Methyl-5-methylsulfanyl-thiazol-2-ylamine 5-Bromo-4-methyl-thiazol-2-ylamine (1.35 g, 7 mmol,) was dissolved in methanol abs. (13.5 mL) and sodium methanethiolate (0.6 g, 7.7 mmol) 1.1 equiv.) was added portionwise at rt. After stirring overnight, the dark colored mixture was concentrated under reduced pressure and purified over a 50 g silica cartridge (NH2-modified) with ethyl acetate as eluent. The desired fractions were evaporated to give the title compound as a light yellow solid: 180 mg, MS (ISP): m/e 161.1 (M+H)⁺ ii) 2-{3-Methyl-5-[({[4-methyl-5-(methylthio)-1,3-thiazol-2-yl]carbamoyl}amino)sulfonyl]-2-thienyl}ethyl acetate The title compound was prepared in analogy to the procedure described in Example 55, starting from 4-methyl-5-methylsulfanyl-thiazol-2-ylamine and acetic acid 2-(3-methyl-5-sulfamoyl-thiophen-2-yl)-ethyl ester to obtain the desired compound as a white, amorphous solid. MS (ISN): m/e 448.2 (M−H)⁻

Example 86

5-(2-Hydroxyethyl)-4-methyl-N-{[4-methyl-5-(methylthio)-1,3-thiazol-2-yl]carbamoyl}thiophene-2-sulfonamide The title compound was prepared in analogy to the procedure described in Example 56, starting from 2-{3-methyl-5-[({[4-methyl-5-(methylthio)-1,3-thiazol-2-yl]carbamoyl}amino)sulfonyl]-2-thienyl}ethyl acetate to obtain the desired compound as a white, amorphous solid. MS (ISN): m/e 406.4 (M−H)⁻

Example 87

2-{5-[({[4-(Methoxymethyl)-5-(methylthio)-1,3-thiazol-2-yl]carbamoyl}amino)sulfonyl]-3-methyl-2-thienyl}ethyl acetate i) 4-Methoxymethyl-thiazol-2-ylamine 1,3-Dibromo-propan-2-one (9 g, 42 mmol) was dissolved in methanol. (90 mL) followed by the addition of thiourea (3.2 g, 42.5 mmol) and the dark colored mixture was refluxed overnight. The solvent was then removed under reduced pressure and the remaining oil was dissolved in an ethyl acetate/water. The mixture was acidified with 1N HCl to pH 1 and extracted with three portions of ethyl acetate. The aqueous layer was then treated with solid sodium carbonate to pH 8 and again extracted with three portions of ethyl acetate. The combined, organic extracts were washed with water and brine, dried over magnesium sulfate, filtered and concentrated under reduced pressure to give the crude product. After purification on silica gel (NH2-modified) with ethyl acetate/n-hepatane as eluents, the desired fractions were combined and concentrated under reduced pressure to yield a solid which was stirred in diethyl ether, filtered and dried to give the title compound as a light brown solid. (0.53 g, 9% yield) MS (ISP): m/e 145.1 (M−H)⁺ ii) (4-Methoxymethyl-thiazol-2-yl)-carbamic acid tert-butyl ester 4-methoxymethyl-thiazol-2-ylamine (16.7 g, 116 mmol, ca. 1.0 equiv. crude) was dissolved in THF and filtered over a pad of dicalite. The filtrate was cooled with an ice-bath, and di-tert.-butyl-dicarbonate (30.3 g, 139 mmol, 1.2 equiv.) was added portionwise followed by 4-dimethylaminopyridine. (1.4 g, 11.1 mol). The mixture was then stirred at rt overnight and then concentrated under reduced pressure. After an extractive workup in ethyl acetate with potassium hydrogen sulfate solution 5% and sodium carbonate solution half saturated, the organic fraction was dried over magnesium sulfate, filtered and concentrated under reduced pressure. The crude product was then purified on silica gel with tert. butyl methyl ether and n-heptane as eluents to give the title compound as a light orange solid. (1.0 g, 3.7%) MS (ISN): m/e 243.1 (M−H)⁻ iii) (4-Methoxymethyl-5-methylsulfanyl-thiazol-2-yl)-carbamic acid tert-butyl ester (4-Methoxymethyl-thiazol-2-yl)-carbamic acid tert-butyl ester (840 mg, 3.4 mmol) was dissolved in dry THF (21 mL). At ~−75° C. was added dropwise n-butyllithium solution 1.6 M in hexanes. (8.6 ml, 13.7 mmol). The dark-red mixture was stirred at ~−75° C. for 30 min. At ~−70° C. was then added dropwise methyl disulfide (970 mg, 10.3 mmol). The resultant yellow colored mixture was slowly warmed to rt and further stirred overnight. After quenching the reaction with saturated ammonium chloride solution, the organic layer was washed with brine, dried over magnesium sulfate, filtered and concentrated under reduced pressure. After purification on silica gel with ethyl acetate and n-heptaene as eluents the title compound was obtained as a light yellow solid. (630 mg, 59%) MS (ISP): m/e 291.3 (M−H)⁺ iv) 4-Methoxymethyl-5-methylsulfanyl-thiazol-2-ylamine (4-Methoxymethyl-5-methylsulfanyl-thiazol-2-yl)-carbamic acid tert-butyl ester (380 mg, 1.3 mmol) was dissolved in 4 M HCl/1,4-dioxane (7.2 mL, 28.8 mmol) and stirred at 50° C. for 4 hours. The reaction was concentrated under reduced pressure and the residue was dissolved in ethyl acetate and extracted with a half saturated sodium hydrogen carbonate solution. The organic layer was dried over magnesium sulfate, filtered and concentrated under reduced pressure to give the title compound as a yellow solid. (238 mg, 86%)

v) 2-{5-[({[4-(Methoxymethyl)-5-(methylthio)-1,3-thiazol-2-yl]carbamoyl}amino)sulfonyl]-3-methyl-2-thienyl}ethyl acetate The title compound was prepared in analogy to the procedure described in Example 55, starting from 4-methoxymethyl-5-methylsulfanyl-thiazol-2-ylamine and acetic acid 2-(3-methyl-5-sulfamoyl-thiophen-2-yl)-ethyl ester to obtain the desired compound as a white solid. MS (ISN): m/e 477.9 (M−H)⁻

Example 88

5-(2-Hydroxyethyl)-N-{[4-(methoxymethyl)-5-(methylthio)-1,3-thiazol-2-yl]carbamoyl}-4-methylthiophene-2-sulfonamide The title compound was prepared in analogy to the procedure described in Example 56, starting from 2-{5-[({[4-(methoxymethyl)-5-(methylthio)-1,3-thiazol-2-yl]carbamoyl}amino)sulfonyl]-3-methyl-2-thienyl}ethyl acetate to obtain the desired compound as a white solid. MS (ISN): m/e 436.0 (M−H)⁻

Example 89

N-[(4-Methoxy-1,3-benzothiazol-2-yl)carbamoyl]-5-(2-methoxyethyl)-4-methylthiophene-2-sulfonamide The title compound was prepared in analogy to the procedure described in Example 45, starting from 5-(2-methoxyethyl)-4-methyl-thiophene-2-sulfonic acid amide and 4-methoxy-benzo[b]thiophen-2-ylamine to obtain the desired compound as a white solid. MS (ISN): m/e 440.2 (M−H)⁻

Example 90

5-(2-Methoxyethyl)-N-[(5-methoxy[1,3]thiazolo[5,4-b]pyridin-2-yl)carbamoyl]-4-methylthiophene-2-sulfonamide The title compound was prepared in analogy to the procedure described in Example 45, starting from 5-(2-methoxyethyl)-4-methyl-thiophene-2-sulfonic acid amide and 5-methoxy-thiazolo[5,4-b]pyridin-2-ylamine to obtain the desired compound as a white solid. MS (ISN): m/e 441.3 (M−H)⁻

Example 91

5-(2-Methoxyethyl)-4-methyl-N-[(4-methyl-1,3-benzothiazol-2-yl)carbamoyl]thiophene-2-sulfonamide The title compound was prepared in analogy to the procedure described in Example 45 starting from 5-(2-methoxyethyl)-4-methyl-thiophene-2-sulfonic acid amide and 4-methyl-benzothiazol-2-ylamine to obtain the desired compound as a white solid. MS (ISN): m/e 424.3 (M−H)⁺

Example 92

N-[(7-Chloro-4-methoxy-1,3-benzothiazol-2-yl)carbamoyl]-5-(2-hydroxyethyl)-4-methylthiophene-2-sulfonamide The title compound was prepared in analogy to the procedure described in Example 55 starting from acetic acid 3-methyl-5-sulfamoyl-thiophen-2-ylmethyl ester (89 mg, 0.34 mmol) and 7-chloro-4-methoxy-benzothiazol-2-ylamine (79.8 mg, 0.37 mmol) to obtain the crude acetate intermediate. This intermediate was then converted in analogy to the procedure described in Example 56 to obtain the title compound as a white solid. MS (ISN): m/e 460.4 (M−H)⁻

Example 93

5-(2-Hydroxyethyl)-N-[(4-methoxy-1,3-benzothiazol-2-yl)carbamoyl]-4-methylthiophene-2-sulfonamide The title compound was prepared in analogy to the procedure described in Example 55 starting from acetic acid 3-methyl-5-sulfamoyl-thiophen-2-ylmethyl ester (112 mg, 0.43 mmol) and 4-methoxy-benzothiazol-2-ylamine (115 mg, 0.64 mmol) to obtain the crude acetate intermediate. This intermediate was then converted in analogy to the procedure described in Example 56 to obtain the title compound as a white solid.
MS (ISN): m/e 426.2 (M−H)⁻

Example 94

5-(2-Hydroxyethyl)-4-methyl-N-[(4-methyl-1,3-benzothiazol-2-yl)carbamoyl]thiophene-2-sulfonamide The title compound was prepared in analogy to the procedure described in Example 55 starting from acetic acid 3-methyl-5-sulfamoyl-thiophen-2-ylmethyl ester (131 mg, 0.5 mmol) and 4-methyl-benzothiazol-2-ylamine (123 mg, 0.75 mmol) to obtain the crude intermediate. This intermediate was then converted in analogy to the procedure described in Example 56 to obtain the title compound as a white solid. MS (ISN): m/e 410.0 (M−H)⁻

Example 95

N-[(5-Methoxy-4-methyl-1,3-thiazol-2-yl)carbamoyl]-5-methylthiophene-3-sulfonamide The title compound was prepared in analogy to the procedure described in Example 52 starting from 5-methyl-thiophene-3-sulfonic acid amide and 5-methoxy-4-methyl-thiazol-2-ylamine to obtain the desired compound as a light brown solid. MS (ISN): m/e 346.0 (M−H)⁻

Example 96

5-(2-Methoxyethyl)-N-[(5-methoxy-4-methyl-1,3-thiazol-2-yl)carbamoyl]-4-methylthiophene-2-sulfonamide The title compound was prepared in analogy to the procedure described in Example 52 starting from 5-(2-methoxyethyl)-4-methyl-thiophene-2-sulfonic acid amide and 5-methoxy-4-methyl-thiazol-2-ylamine to obtain the desired compound as a white solid. MS (ISN): m/e 404.2 (M−H)⁻

Example 97

5-(2-Methoxyethyl)-N-[(5-methoxy-1,3-thiazol-2-yl)carbamoyl]-4-methylthiophene-2-sulfonamide The title compound was prepared in analogy to the procedure described in Example 54 starting from 5-(2-methoxyethyl)-4-methyl-thiophene-2-sulfonic acid amide and 2-amino-5-methoxythiazole to obtain the desired compound as a white solid. MS (ISN): m/e 390.0 (M−H)⁻

Example 98

6-(2-Hydroxyethyl)-4-methyl-N-({4-methyl-5-[(trifluoromethyl)thio]-1,3-thiazol-2-yl}carbamoyl)thiophene-2-sulfonamide i) 4-Methyl-5-trifluoromethylsulfanyl-thiazol-2-ylamine The title compound was prepared in analogy to the procedure described in Example 87iii) starting from 4-methyl-thiazol-2-ylamine and trifluoro-trifluoromethyldisulfanyl-methane.

ii) 5-(2-Hydroxyethyl)-4-methyl-N-({4-methyl-5-[(trifluoromethyl)thio]-1,3-thiazol-2-yl}carbamoyl)thiophene-2-sulfonamide The title compound was prepared in analogy to the procedure described in Example 55 starting from acetic acid 3-methyl-5-sulfamoyl-thiophen-2-ylmethyl ester (36.8 mg, 0.14 mmol) and 4-methyl-5-trifluoromethylsulfanyl-thiazol-2-ylamine (30 mg, 0.14 mmol) to obtain the crude acetate intermediate. This intermediate was then converted in analogy to the procedure described in Example 56 to obtain the title compound as a white solid. MS (ISN): m/e 460.3 (M−H)⁻.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound selected from:
N-[(5-Bromo-1,3-thiazol-2-yl)carbamoyl]-5-methyl-1-benzothiophene-2-sulfonamide;
N-[(5-Bromo-1,3-thiazol-2-yl)carbamoyl]-1-benzothiophene-2-sulfonamide;
N-[(5-Bromo-1,3-thiazol-2-yl)carbamoyl]-5-fluoro-3-methyl-1-benzothiophene-2-sulfonamide;
N-[(5-Bromo-1,3-thiazol-2-yl)carbamoyl]-1-benzothiophene-3-sulfonamide;
5-Bromo-N-[(5-bromo-1,3-thiazol-2-yl)carbamoyl]-3-methyl-1-benzothiophene-2-sulfonamide;
N-[(5-Bromo-1,3-thiazol-2-yl)carbamoyl]-6,7-dihydro-4H-thieno[3,2-c]pyran-2-sulfonamide;
N-[(5-Bromo-1,3-thiazol-2-yl)carbamoyl]-5-methoxy-1-benzothiophene-3-sulfonamide;
N-[(5-Bromo-1,3-thiazol-2-yl)carbamoyl]-1-methyl-1H-indole-2-sulfonamide;
N-[(5-Bromo-1,3-thiazol-2-yl)carbamoyl]-6-methoxy-1-benzothiophene-2-sulfonamide;
Methyl-3-({[(5-bromo-1,3-thiazol-2yl)carbamoyl]amino}sulfonyl)-1-benzothiophene-5-carboxylate;
N-[(5-Bromo-1,3-thiazol-2-yl)carbamoyl]-5-methyl-1-benzothiophene-3-sulfonamide;
N-[(5-Bromo-1,3-thiazol-2-yl)carbamoyl]-5-chloro-1-benzothiophene-3-sulfonamide;
N-[(5-Bromo-1,3-thiazol-2-yl)carbamoyl]-5-chloro-1-benzothiophene-2-sulfonamide;
N-[(5-Bromo-1,3-thiazol-2-yl)carbamoyl]-7-methyl-1-benzothiophene-2-sulfonamide;
7-Bromo-N-[(5-bromo-1,3-thiazol-2-yl)carbamoyl]-6-methoxy-1-benzothiophene-2-sulfonamide;
N-[(5-bromo-1,3-thiazol-2-yl)carbamoyl]-5-(3,5-dimethylisoxazol-4-yl)-1-benzothiophene-2-sulfonamide;
N-[(5-Bromo-1,3-thiazol-2-yl)carbamoyl]-5-methoxy-1-benzothiophene-2-sulfonamide;
N-[(5-Bromo-1,3-thiazol-2-yl)carbamoyl]-7-chloro-1-benzothiophene-3-sulfonamide;
N-[(5-Bromo-1,3-thiazol-2-yl)carbamoyl]-7-chloro-1-benzothiophene-2-sulfonamide;
N-[(5-Bromo-1,3-thiazol-2-yl)carbamoyl]-1H-indole-2-sulfonamide; and
N-[(5-Bromo-1,3-thiazol-2-yl)carbamoyl]-7-(3,5-dimethylisoxazol-4-yl)-1-benzothiophene-2-sulfonamide.

2. A compound, selected from:
N-[(5-Bromo-1,3-thiazol-2-yl)carbamoyl]-7-pyridin-4-yl-1-benzothiophene-2-sulfonamide;
N-[(5-Bromo-1,3-thiazol-2-yl)carbamoyl]-1-methyl-1H-1-indole-3-sulfonamide;
5-(Benzyloxy)-N-[(5-bromo-1,3-thiazol-2-yl)carbamoyl]-1-methyl-1H-indole-3-sulfonamide;
Methyl 3-({[(5-bromo-1,3-thiazol-2-yl)carbamoyl]amino}sulfonyl)-1-methyl-1H-indole-5-carboxylate;
N-[(5-Bromo-1,3-thiazol-2-yl)carbamoyl]-5-fluoro-1-methyl-1H-indole-3-sulfonamide;
Methyl 3-({[(5-bromo-1,3-thiazol-2-yl)carbamoyl]amino}sulfonyl)-1-methyl-1H-indole-6-carboxylate;
6-(Benzyloxy)-N-[(5-bromo-1,3-thiazol-2-yl)carbamoyl]-1-methyl-1H-indole-3-sulfonamide;
N-[(5-Bromo-1,3-thiazol-2-yl)carbamoyl]-6-cyano-1-methyl-1H-indole-3-sulfonamide;
N-[(5-Bromo-1,3-thiazol-2-yl)carbamoyl]-1-methyl-6-(methylsulfonyl)-1H-indole-3-sulfonamide;
N-[(5-Bromo-1,3-thiazol-2-yl)carbamoyl]-1-(2-methoxyethyl)-1H-indole-3-sulfonamide;
Methyl 3-({[(5-bromo-1,3-thiazol-2-yl)carbamoyl]amino}sulfonyl)-1-methyl-1H-indole-7-carboxylate;
N-[(5-Bromo-1,3-thiazol-2-yl)carbamoyl]-7-methoxy-1-methyl-1H-indole-3-sulfonamide;
7-Bromo-N-[(5-bromo-1,3-thiazol-2-yl)carbamoyl]-1-methyl-1H-indole-3-sulfonamide;
N-[(5-Bromo-4-methyl-1,3-thiazol-2-yl)carbamoyl]-5-(methoxymethyl)-4-methylfuran-2-sulfonamide;
N-[(5-Bromo-1,3-thiazol-2-yl)carbamoyl]-5-(methoxymethyl)-4-methylfuran-2-sulfonamide;
7-(Benzyloxy)-N-[(5-bromo-1,3-thiazol-2-yl)carbamoyl]-1-benzothiophene-2-sulfonamide;
N-[(5-bromo-1,3-thiazol-2-yl)carbamoyl]-7-(2-methoxyethoxy)-1-benzothiophene-2-sulfonamide;
N-[(5-Bromo-1,3-thiazol-2-yl)carbamoyl]-7-methoxy-1-benzothiophene-2-sulfonamide;
N-[(5-Bromo-1,3-thiazol-2-yl)carbamoyl]-7-methoxy-1-methyl-1H-indole-2-sulfonamide;
7-(Benzyloxy)-N-[(5-bromo-1,3-thiazol-2-yl)carbamoyl]-1-methyl-1H-indole-3-sulfonamide; and
N-[(5-bromo-1,3-thiazol-2-yl)carbamoyl]-7-(2-methoxyethoxy)-1-methyl-1H-indole-3-sulfonamide.

3. A compound, selected from:
N-[(5-bromo-1,3-thiazol-2-yl)carbamoyl]-7-methoxy-1H-indole-3-sulfonamide;
7-Methoxy-N-[(5-methoxy-1,3-thiazol-2-yl)carbamoyl]-1-methyl-1H-indole-3-sulfonamide;
N-[(5-Methoxy-1,3-benzothiazol-2-yl)carbamoyl]-5-(2-methoxyethyl)-4-methylthiophene-2-sulfonamide;

2-{[3-({[(5-Methoxy-1,3-thiazol-2-yl)carbamoyl]amino}sulfonyl)-1-methyl-1H-indol-7-yl]oxy}ethyl acetate;

7-(2-Hydroxyethoxy)-N-[(5-methoxy-1,3-thiazol-2-yl)carbamoyl]-1-methyl-1H-indole-3-sulfonamide;

2-{[3-({[(5-Bromo-1,3-thiazol-2-yl)carbamoyl]amino}sulfonyl)-1-methyl-1H-indol-7-yl]oxy}ethyl acetate;

N-[(5-Bromo-1,3-thiazol-2-yl)carbamoyl]-7-(2-hydroxyethoxy)-1-methyl-1H-indole-3-sulfonamide;

Ethyl {[3-({[(5-bromo-1,3-thiazol-2-yl)carbamoyl]amino}sulfonyl)-1-methyl-1H-indol-7-yl]oxy}acetate;

2-{[3-({[(5-Bromo-1,3-thiazol-2-yl)carbamoyl]amino}sulfonyl)-1-methyl-1H-indol-7-yl]oxy}acetamide;

7-Methoxy-N-[(5-methoxy-4-methyl-1,3-thiazol-2-yl)carbamoyl]-1-methyl-1H-indole-3-sulfonamide;

2-{[3-{[(5-Methoxy-4-methyl-1,3-thiazol-2-yl)carbamoyl]amino}sulfonyl)-1-methyl-1H-indol-7-yl]oxy}acetamide;

5-Methoxy-N-[(5-methoxy-1,3-thiazol-2-yl)carbamoyl]-1-benzothiophene-2-sulfonamide;

2-[5-({[(5-methoxy[1,3]thiazolo[5,4-b]pyridin-2-yl)carbamoyl]amino}sulfonyl)-3-methyl-2-thienyl]ethyl acetate;

5-(2-Hydroxyethyl)-N-[(5-methoxy[1,3]thiazolo[5,4-b]pyridin-2-yl)carbamoyl]-4-methylthiophene-2-sulfonamide;

N-[(5-Bromo-4-ethyl-1,3-thiazol-2-yl)carbamoyl]-5-methylthiophene-3-sulfonamide;

N-[(5-Bromo-4-ethyl-1,3-thiazol-2-yl)carbamoyl]-5-(2-methoxyethyl)-4-methylthiophene-2-sulfonamide; and N-[(5-Bromo-4-ethyl-1,3-thiazol-2-yl)carbamoyl]-4-(2-methoxyethyl)-5-methylthiophene-2-sulfonamide.

4. A compound selected from:

N-[(5-Ethyl-4-methyl-1,3-thiazol-2-yl)carbamoyl]-5-(2-methoxyethyl)-4-methylthiophene-2-sulfonamide;

N-[(4-Ethyl-5-methoxy-1,3-thiazol-2-yl)carbamoyl]-5-methylthiophene-3-sulfonamide;

N-[(4,5-Diethyl-1,3-thiazol-2-yl)carbamoyl]-5-methylthiophene-3-sulfonamide;

N-[(4,5-Diethyl-1,3-thiazol-2-yl)carbamoyl]-5-(2-methoxyethyl)-4-methylthiophene-2-sulfonamide;

2-[5-({[(5-Bromo-4-methyl-1,3-thiazol-2-yl)carbamoyl]amino}sulfonyl)-3-methyl-2-thienyl]ethyl acetate;

5-Methyl-N-[(5-methyl-4-phenyl-1,3-thiazol-2-yl)carbamoyl]thiophene-3-sulfonamide;

5-(2-Methoxyethyl)-4-methyl-N-[(5-methyl-4-phenyl-1,3-thiazol-2-)carbamoyl]thiophene-2-sulfonamide;

2-[5-({[(4,5-Diethyl-1,3-thiazol-2-yl)carbamoyl]amino}sulfonyl)-3-methyl-2-thienyl]ethyl acetate;

2-[5-({[(5-Ethyl-4-methyl-1,3-thiazol-2-yl)carbamoyl]amino}sulfonyl)-3-methyl-2-thienyl]ethyl acetate;

N-[(4,5-Diethyl-1,3-thiazol-2-yl)carbamoyl]-5-(2-hydroxyethyl)-4-methylthiophene-2-sulfonamide;

N-[(5-Ethyl-4-methyl-1,3-thiazol-2-yl)carbamoyl]-5-(2-hydroxyethyl)-4-methylthiophene-2-sulfonamide;

N-[(5-Ethyl-4-phenyl-1,3-thiazol-2-yl)carbamoyl]-5-methylthiophene-3-sulfonamide;

N-[(5-Ethyl-4-phenyl-1,3-thiazol-2-yl)carbamoyl]-5-(2-methoxyethyl)-4-methylthiophene-2-sulfonamide;

2-[3-Methyl-5-({[(5-methyl-4-phenyl-1,3-thiazol-2-yl)carbamoyl]amino}sulfonyl)-2-thienyl]ethyl acetate;

2-[5-({[(5-Methoxy-4-methyl-1,3-thiazol-2-yl)carbamoyl]amino}sulfonyl)-3-methyl-2-thienyl]ethyl acetate;

2-[5-({[(5-Ethyl-4-isopropyl-1,3-thiazol-2-yl)carbamoyl]amino}sulfonyl)-3-methyl-2-thienyl]ethyl acetate;

5-(2-Hydroxyethyl)-4-methyl-N-[(5-methyl-4-phenyl-1,3-thiazol-2-yl)carbamoyl]thiophene-2-sulfonamide; and N-[(5-Ethyl-4-isopropyl-1,3-thiazol-2-yl)carbamoyl]-5-(2-methoxyethyl)-4-methylthiophene-2-sulfonamide.

5. A compound, selected from the group consisting of:

N-[(5-Ethyl-4-isopropyl-1,3-thiazol-2-yl)carbamoyl]-5-methylthiophene-3-sulfonamide;

N-[(5-Ethyl-4-isopropyl-1,3-thiazol-2-yl)carbamoyl]-5-(2-hydroxyethyl)-4-methylthiophene-2-sulfonamide;

2-{5-({[(5-Ethyl-4-phenyl-1,3-thiazol-2-yl)carbamoyl}amino]sulfonyl)-3-methyl-2-thienyl}ethyl acetate;

N-[(5-Ethyl-4-phenyl-1,3-thiazol-2-yl)carbamoyl]-5-(2-hydroxyethyl)-4-methylthiophene-2-sulfonamide;

N-{[4-Ethyl-5-(methylthio)-1,3-thiazol-2-yl]carbamoyl}-5-(2-methoxyethyl)-4-methylthiophene-2-sulfonamide;

2-{5-[({[4-Ethyl-5-(methylthio)-1,3-thiazol-2-yl]carbamoyl}amino)sulfonyl]-3-methyl-2-thienyl}ethyl acetate;

N-{[4-Ethyl-5-(methylthio)-1,3-thiazol-2-yl]carbamoyl}-5-(2-hydroxyethyl)-4-methylthiophene-2-sulfonamide;

2-{3-Methyl-5-[({[4-methyl-5-(methylthio)-1,3-thiazol-2-yl]carbamoyl}amino)sulfonyl]-2-thienyl}ethyl acetate;

5-(2-Hydroxyethyl)-4-methyl-N-{[4-methyl-5-(methylthio)-1,3-thiazol-2-yl]carbamoyl}thiophene-2-sulfonamide;

2-{5[({[4-(Methoxymethyl)-5-(methylthio)-1,3-thiazol-2-yl]carbamoyl}amino)sulfonyl]-3-methyl-2-thienyl}ethyl acetate;

5-(2-Hydroxyethyl)-N-{[4-(methoxymethyl)-5-(methylthio)-1,3-thiazol-2-yl]carbamoyl}-4-methylthiophene-2-sulfonamide;

N-[(4-Methoxy-1,3-benzothiazol-2-yl)carbamoyl]-5-(2-methoxyethyl)-4-methylthiophene-2-sulfonamide;

5-(2-Methoxyethyl)-N-[(5-methoxy[1,3]thiazolo[5,4-b]pyridin-2-yl)carbamoyl]-4-methylthiophene-2-sulfonamide;

5-(2-Methoxyethyl)-4-methyl-N-[(4-methyl-1,3-benzothiazol-2-yl)carbamoyl]thiophene-2-sulfonamide;

N-[(7-Chloro-4-methoxy-1,3-benzothiazol-2-yl)carbamoyl]-5-(2-hydroxyethyl)-4-methylthiophene-2-sulfonamide;

5-(2-Hydroxyethyl)-N-[(4-methoxy-1,3-benzothiazol-2-yl)carbamoyl]-4-methylthiophene-2-sulfonamide;

5-(2-Hydroxyethyl)-4-methyl-N-[(4-methyl-1,3-benzothiazol-2-yl)carbamoyl]thiophene-2-sulfonamide;

N-[(5-Methoxy-4-methyl-1,3-thiazol-2-yl)carbamoyl]-5-methylthiophene-3-sulfonamide;

5-(2-Methoxyethyl)-N-[(5-methoxy-4-methyl-1,3-thiazol-2-yl)carbamoyl]-4-methylthiophene-2-sulfonamide;

5-(2-Methoxyethyl)-N-[(5-methoxy-1,3-thiazol-2-yl)carbamoyl]-4-methylthiophene-2-sulfonamide; and 5-(2-Hydroxyethyl)-4-methyl-N-({4-methyl-5-[(trifluoromethyl)thio]-1,3-thiazol-2-yl}carbamoyl)thiophene-2-sulfonamide;

N-[(5-bromo-1,3-thiazol-2-yl)carbamoyl]-7-methoxy-1-methyl-1H-indole-3-sulfonamide;

N-[(5-bromo-1,3-thiazol-2-yl)carbamoyl]-5-(methoxymethyl)-4-methylfuran-2-sulfonamide;

N-[(5-bromo-1,3-thiazol-2-yl)carbamoyl]-7-methoxy-1-benzothiophene-2-sulfonamide;

7-methoxy-N-[(5-methoxy-1,3-thiazol-2-yl)carbamoyl]-1-methyl-1H-indole-3-sulfonamide;

2-{[3-({[(5-Bromo-1,3-thiazol-2-yl)carbamoyl]amino}sulfonyl)-1-methyl-1H-indol-7-yl]oxy}acetamide;

7-methoxy-N-[(5-methoxy-4-methyl-1,3-thiazol-2-yl)carbamoyl]-1-methyl-1H-indole-3-sulfonamide;

2-{[3-({[(5-methoxy-4-methyl-1,3-thiazol-2-yl)carbamoyl]amino}sulfonyl)-1-methyl-1H-indol-7-yl]oxy}acetamide;

5-(2-Hydroxyethyl)-N-[(5-methoxy[1,3]thiazolo[5,4-b]pyridin-2-yl)carbamoyl]-4-methylthiophene-2-sulfonamide;

N-[(5-ethyl-4-methyl-1,3-thiazol-2-yl)carbamoyl]-5-(2-methoxyethyl)-4-methylthiophene-2-sulfonamide;

N-[(4,5-diethyl-1,3-thiazol-2-yl)carbamoyl]-5-methylthiophene-3-sulfonamide;

N-[(5-ethyl-4-methyl-1,3-thiazol-2-yl)carbamoyl]-5-(2-hydroxyethyl)-4-methylthiophene-2-sulfonamide;

N-[(5-ethyl-4-isopropyl-1,3-thiazol-2-yl)carbamoyl]-5-methylthiophene-3-sulfonamide;

N-[(5-ethyl-4-phenyl-1,3-thiazol-2-yl)carbamoyl]-5-(2-hydroxyethyl)-4-methylthiophene-2-sulfonamide;

N-{-[4-ethyl-5-(methylthio)-1,3-thiazol-2-yl]carbamoyl}-5-(2-hydroxyethyl)-4-methylthiophene-2-sulfonamide;

5-(2-hydroxyethyl)-4-methyl-N-{[4-methyl-5-(methylthio)-1,3-thiazol-2-yl]carbamoyl}thiophene-2-sulfonamide;

5-(2-hydroxyethyl)-N-{[4-(methoxymethyl)-5-(methylthio)-1,3-thiazol-2-yl]carbamoyl}-4-methylthiophene-2-sulfonamide;

5-(2-Methoxyethyl)-N-[(5-methoxy[1,3]thiazolo[5,4-b]pyridin-2-yl)carbamoyl]-4-methylthiophene-2-sulfonamide;

N-[(7-Chloro-4-methoxy-1,3-benzothiazol-2-yl)carbamoyl]-5-(2-hydroxyethyl)-4-methylthiophene-2-sulfonamide;

5-(2-Hydroxyethyl)-4-methyl-N-[(4-methyl-1,3-benzothiazol-2-yl)carbamoyl]thiophene-2-sulfonamide; and N-[(5-Methoxy-4-methyl-1,3-thiazol-2-yl)carbamoyl]-5-methylthiophene-3-sulfonamide; and 5-(2-hydroxyethyl)-4-methyl-N-({4-methyl-5[(trifluoromethyl)thio]-1,3-thiazol-2-yl}carbamoyl)thiophene-2-sulfonamide.

6. A pharmaceutical composition, comprising a therapeutically effective amount of a compound according to claim 5 and a therapeutically inert carrier.

\* \* \* \* \*